United States Patent [19]

Artz

[11] Patent Number: 4,678,498

[45] Date of Patent: Jul. 7, 1987

[54] HERBICIDAL SULFONAMIDES

[75] Inventor: Steven P. Artz, Kennett Square, Pa.

[73] Assignee: E. I. Du Pont de Nemours and Company, Wilmington, Del.

[21] Appl. No.: 860,229

[22] Filed: May 12, 1986

Related U.S. Application Data

[63] Continuation-in-part of Ser. No. 743,955, Jun. 12, 1985, abandoned.

[51] Int. Cl.$^4$ .................. A01N 43/54; C07D 239/69; C07D 401/12; C07D 413/12

[52] U.S. Cl. .......................................... 71/87; 71/86; 71/90; 71/92; 71/93; 544/243; 544/296; 544/321; 544/324; 544/323; 544/331; 544/332; 544/229; 544/211; 544/212; 544/206; 544/207; 544/208; 544/209

[58] Field of Search .................. 71/92, 90, 86, 87; 544/243, 296, 321, 324, 323, 331, 332, 229

[56] References Cited

U.S. PATENT DOCUMENTS 4,511,392  4/1985  Rorer ..................................... 71/90

*Primary Examiner*—John M. Ford

[57] ABSTRACT

Novel compounds of Formula I are useful as herbicides and plant growth regulants.

24 Claims, No Drawings

HERBICIDAL SULFONAMIDES

RELATED APPLICATION

This is a continuation-in-part of application U.S. Ser. No. 743,955 filed June 12, 1985, now abandoned.

BACKGROUND OF THE INVENTION

No. EP-A-44,209 discloses herbicidal sulfonamides of formula

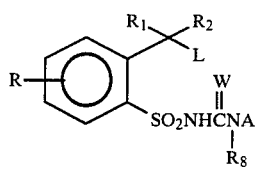

wherein

R is H, F, Cl, Br, $NO_2$, $CF_3$, $C_1$–$C_3$ alkyl or $C_1$–$C_3$ alkoxy;

$R_1$ is H, Cl or $C_1$–$C_4$ alkyl;

$R_2$ is H or $CH_3$; and

L is, among other values, $CO_2R_{10}$, $CONR_3R_4$, CN, Cl, Br, $NR_3R_4$, $S(O)_nR_7$, $SO_2NR_3R_4$ and $OR_9$.

No. EP-A-112,803 discloses, in part, herbicidal sulfonamides of formula

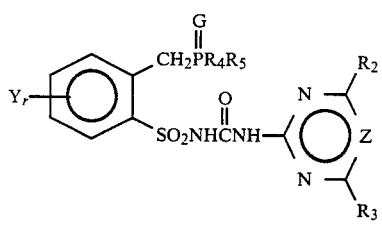

South African Patent Application No. 84/2722 discloses herbicidal sulfonamides of formula

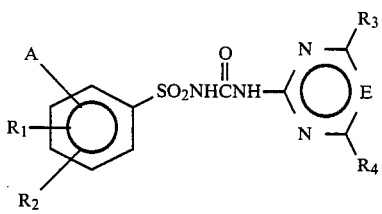

wherein

A is $CR_6R_7XR_8$, $CR_9R_{10}R_{11}$ or $CHR_7SCQR_{21}$;

$R_9$ and $R_{10}$ are, among other values, H or $CH_3$; and $R_{11}$ is $COR_{24}$ or a $C_1$–$C_4$ alkyl group substituted with, among other values, CN, $NO_2$, OH, $C_1$–$C_4$ alkoxy, $C_1$–$C_4$ alkylthio, $C_1$–$C_4$ alkylsulfinyl, $C_1$–$C_4$ alkylsulfonyl, $C_1$–$C_4$ haloalkoxy, $NR_{12}R_{13}$ and $SO_2NR_{15}R_{16}$.

No. EP-A-162,723 discloses 2,5-substituted herbicidal sulfonamides of formula

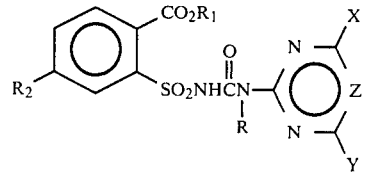

wherein

R is H or CH;

$R_1$ is $C_1$–$C_3$ alkyl; and $R_2$ is $C_2$–$C_6$ alkoxy, $C_1$–$C_6$ alkylthio, $C_3$–$C_6$ alkenyl, $C_3$–$C_6$ alkynyloxy, $C_3$–$C_6$ alkenylthio, $C_3$–$C_6$ alkynylthio, $OCH_2CH_2OCH_3$, $OCH_2CH_2SCH_3$, $CH_2F$, $CHF_2$, $OCF_2H$, $OCH_2CH_2F$, $OCH_2CHF_2$, $OCH_2CF_3$, $OCH_2CH_2Cl$, $C_2$–$C_6$ alkyl substituted with 1–3 atoms of F or Cl or $C_1$–$C_4$ alkyl substituted with $C_1$–$C_2$ alkoxy or $C_1$–$C_2$ alkylthio.

SUMMARY OF THE INVENTION

This application pertains to novel compounds of Formula I, agriculturally suitable compositions containing them and their method-of-use as preemergent and/or postemergent herbicides or plant growth regulants.

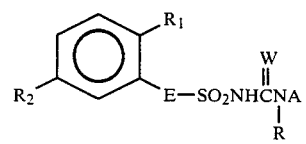

wherein

E is $CH_2$ or a single bond;

W is O or S;

R is H or $CH_3$;

$R_1$ is F, Cl, Br, $NO_2$, $C_1$–$C_4$ alkyl, $C_2$–$C_4$ alkenyl, $C_2$–$C_4$ haloalkenyl, $C_2$–$C_4$ alkynyl, $C_1$–$C_4$ haloalkyl, $C_1$–$C_4$ alkoxy, $OCH_2CH_2OCH_3$, $C_1$–$C_4$ haloalkoxy, $C_3$–$C_4$ alkenyloxy, $C_2$–$C_4$ haloalkenyloxy, $C_3$–$C_4$ alkynyloxy, $CO_2R_3$, $CONR_4R_5$, $SO_2NR_4R_5$, $SO_2N(OCH_3)CH_3$, $S(O)_nR_6$, $OSO_2R_7$, $C_1$–$C_2$ alkyl substituted with $C_1$–$C_2$ alkoxy, OH or $C_1$–$C_2$ alkylthio, $CH_2CN$, $C_6H_5$,

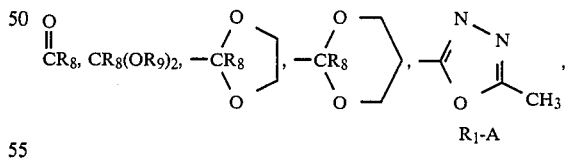

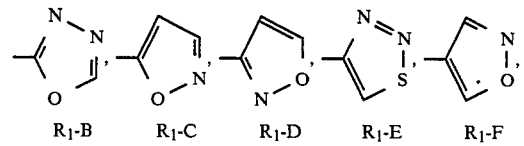

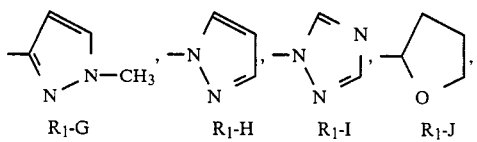

-continued

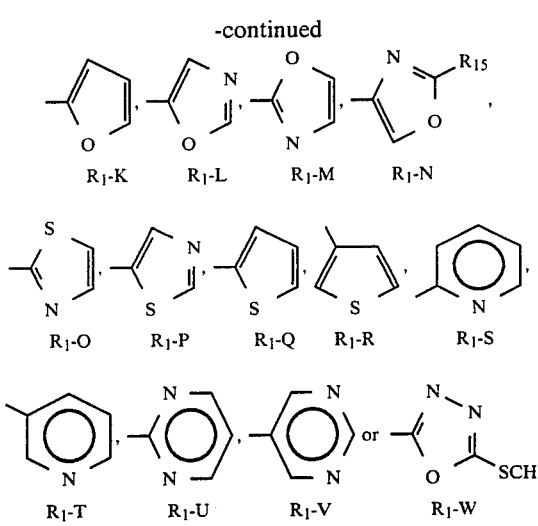

R$_2$ is

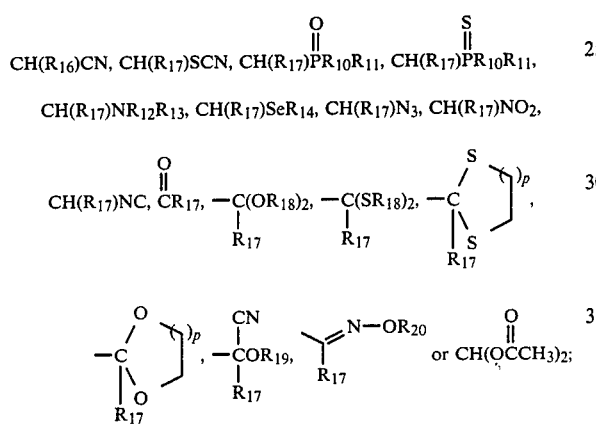

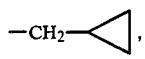

R$_3$ is C$_1$–C$_4$ alkyl, C$_3$–C$_4$ alkenyl, C$_3$–C$_4$ alkynyl,

−CH$_2$−△,

CH$_2$CH$_2$Cl, CH$_2$CH$_2$F, or C$_1$–C$_2$ alkyl substituted with OCH$_3$ or SCH$_3$;
R$_4$ is C$_1$–C$_3$ alkyl;
R$_5$ is H or C$_1$–C$_3$ alkyl;
R$_4$ and R$_5$ may be taken together to form (CH$_2$)$_3$ or (CH$_2$)$_4$;
R$_6$ is C$_1$–C$_3$ alkyl, CH$_2$CH=CH$_2$ or CH$_2$C≡CH;
R$_7$ is C$_1$–C$_3$ alkyl or N(CH$_3$)$_2$;
R$_8$ is H, C$_1$–C$_4$ alkyl, C$_3$–C$_4$ alkenyl, C$_3$–C$_4$ alkynyl, CH$_2$CH$_2$Cl, CH$_2$CH$_2$F, C$_1$–C$_2$ alkyl substituted with OCH$_3$ or SCH$_3$ or C$_3$–C$_6$ cycloalkyl;
R$_9$ is C$_1$–C$_2$ alkyl;
R$_{10}$ and R$_{11}$ are independently C$_1$–C$_2$ alkyl, C$_1$–C$_2$ alkoxy, C$_1$–C$_2$ alkylthio, NHCH$_3$ or N(CH$_3$)$_2$;
R$_{12}$ and R$_{13}$ are independently H or C$_1$–C$_2$ alkyl;
R$_{14}$ is C$_1$–C$_3$ alkyl;
R$_{15}$ is H or CH$_3$;
R$_{16}$ is H, C$_1$–C$_2$ alkyl or F;
R$_{17}$ is H or C$_1$–C$_2$ alkyl;
R$_{18}$ is C$_1$–C$_2$ alkyl;
R$_{19}$ is H, Si(CH$_3$)$_3$ or C$_1$–C$_2$ alkyl;
R$_{20}$ is H or C$_1$–C$_2$ alkyl;

p is 1 or 2;
n is 0, 1, or 2;
A is

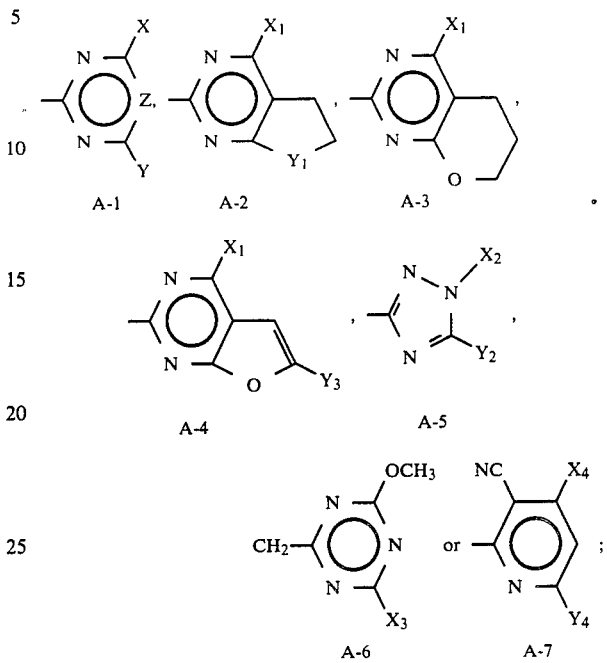

X is H, C$_1$–C$_4$ alkyl, C$_1$–C$_4$ alkoxy, C$_1$–C$_4$ haloalkoxy, C$_1$–C$_4$ haloalkyl, C$_1$–C$_4$ haloalkylthio, C$_1$–C$_4$ alkylthio, halogen, C$_2$–C$_5$ alkoxyalkyl, C$_2$–C$_5$ alkoxyalkoxy, amino, C$_1$–C$_3$ alkylamino or di(C$_1$–C$_3$ alkyl)amino;
Y is H, C$_1$–C$_4$ alkyl, C$_1$–C$_4$ alkoxy, C$_1$–C$_4$ haloalkoxy, C$_1$–C$_4$ haloalkylthio, C$_1$–C$_4$ alkylthio, C$_2$–C$_5$ alkoxyalkyl, C$_2$–C$_5$ alkoxyalkoxy, amino, C$_1$–C$_3$ alkylamino, di(C$_1$–C$_3$ alkyl)amino, C$_3$–C$_4$ alkenyloxy, C$_3$–C$_4$ alkynyloxy, C$_2$–C$_5$ alkylthioalkyl, C$_2$–C$_5$ alkylsulfinylalkyl, C$_2$–C$_5$ alkylsulfonylalkyl, C$_1$–C$_4$ haloalkyl, C$_2$–C$_4$ alkynyl, C$_3$–C$_5$ cycloalkyl, azido, cyano,

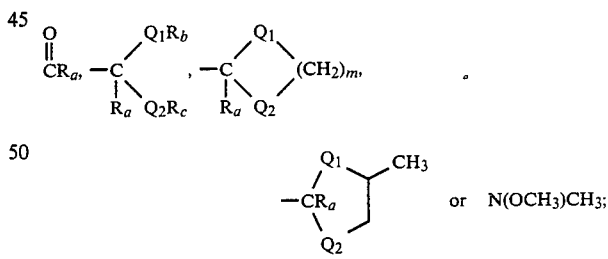

m is 2 or 3;
Q$_1$ and Q$_2$ are independently O or S;
R$_a$ is H or C$_1$–C$_3$ alkyl;
R$_b$ and R$_c$ are independently C$_1$–C$_3$ alkyl;
Z is CH, N, CCH$_3$, CC$_2$H$_5$, CCl or CBr;
Y$_1$ is O or CH$_2$;
X$_1$ is CH$_3$, OCH$_3$, OC$_2$H$_5$ or OCF$_2$H;
X$_2$ is CH$_3$, C$_2$H$_5$ or CH$_2$CF$_3$;
Y$_2$ is OCH$_3$, OCH$_2$H$_5$, SCH$_3$, SC$_2$H$_5$, CH$_3$ or CH$_2$CH$_3$;
X$_3$ is CH$_3$ or OCH$_3$;
Y$_3$ is H or CH$_3$;
X$_4$ is CH$_3$, OCH$_3$, OC$_2$H$_5$, CH$_2$OCH$_3$ or Cl;

$Y_4$ is $CH_3$, $OCH_3$, $OC_2H_5$ or Cl;

and their agriculturally suitable salts; provided that (1) when X is halogen, then Z is CH and Y is $OCH_3$, $OC_2H_5$, $NH_2$, $NHCH_3$, $N(CH_3)_2$, $OCF_2H$ or $N(OCH_3)CH_3$;

(2) when X or Y is $C_1$ haloalkoxy, then Z is CH;

(3) when W is S, then R is H, A is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$,

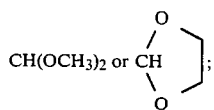

(4) when the total number of carbon atoms of X and Y is greater than four, then the combined number of carbons of $R_1$ and $R_2$ is less than or equal to six;

(5) when $R_2$ is $C(O)R_{17}$, then $R_1$ is other than $C_1$-$C_4$ haloalkyl or $C_2$ alkyl substituted with $C_1$-$C_2$ alkoxy or $C_1$-$C_2$ alkylthio, and Y is other than cyclopropyl;

(6) when Y is $C_2$-$C_5$ alkylthioalkyl, $C_2$-$C_5$ alkylsulfinylalkyl or $C_2$-$C_5$ alkylsulfonylalkyl, then $R_2$ is other than $CH(R_{17})NO_2$; and (7) $X_4$ and $Y_4$ are not simultaneously Cl.

In the above definitions, the term "alkyl", used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be monohalogenated or fully substituted with halogen atoms, which may be the same or different. Examples of haloalkyl include $CH_2CH_2F$, $CF_2CF_3$ and $CH_2CHFCl$.

The total number of carbon atoms in a substituent group is indicated by the $C_i$-$C_j$ prefix where i and j are numbers from 1 to 5. For example, $C_1$-$C_3$ alkylsulfonyl would designate methylsulfonyl through propylsulfonyl, $C_2$ alkoxyalkoxy would designate $OCH_2OCH_3$; $C_4$ alkoxyalkoxy would designate the various isomers of an alkoxy group substituted with a second alkoxy group containing a total of 4 carbon atoms, examples including $OCH_2OCH_2CH_2CH_3$ and $OCH_2CH_2OCH_2CH_3$; as a further example, $C_2$ cyanoalkyl would designate $CH_2CN$ and $C_3$ cyanoalkyl would designate $CH_2CH_2CN$ and $CH(CN)CH_3$.

Preferred for reasons of increased ease of synthesis and/or greater herbicidal efficacy are:

1. Compounds of Formula I where
   W is O; and
   R is H;

2. Compounds of Preferred 1 where
   E is a single bond;
   X is $C_1$-$C_2$ alkyl, $C_1$-$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
   Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

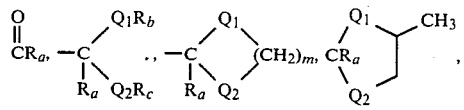

$OCF_2H$, $SCF_2H$, cyclopropyl, $C\equiv CH$ or $C\equiv CCH_3$;

Z is CH or N;

3. Compounds of Preferred 2 where $R_2$ is $CH_2CN$, $CH_2N_3$,

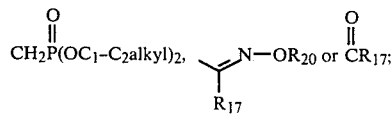

4. Compounds of Preferred 3 where A is A-1.

5. Compounds of Preferred 4 where $R_1$ is F, Cl, Br, $NO_2$, $C_1$-$C_3$ alkyl, $C_1$-$C_2$ alkyl substituted with 1-3 F or Cl or 1 Br, $C_2$-$C_3$ alkenyl, $C_2$-$C_3$ alkenyl substituted with 1-3 F or Cl, $C_1$-$C_2$ alkoxy, $C_1$-$C_2$ alkoxy substituted with 1-3 F or Cl or 1-Br, allyloxy, propargyloxy, $OC(Cl)=CHCl$, $CO_2CH_3$, $CO_2C_2H_5$, $CO_2CH_2CH=CH_2$, $CO_2CH_2CH_2CL$, $CO_2CH_2CH_2OCH_3$, $CONH(C_1$-$C_2$ alkyl), $CONCH_3(C_1$-$C_2$ alkyl), $SO_2N(OCH_3)CH_3$, $SO_2NH(C_1$-$C_2$ alkyl), $SO_2n(C_1$-$C2$ alkyl$)_2$, $S(O)_nC_1$-$C_3$alkyl, $OSO_2$-$C_1$-$C_3$ alkyl, $C_1$-$C_2$ alkyl substituted with $OCH_3$ or $SCH_3$, $C_6H_5$ and $R_1$-A, $R_1$-B, $R_1$-C, $R_1$-D, $R_1$-E, $R_1$-F, $R_1$-G, $R_1$-H, $R_1$-I, $R_1$-J, $R_1$-K, $R_1$-L, $R_1$-M, $R_1$-N, $R_1$-O, $R_1$-P, $R_1$-Q $R_1$-R, $R_1$-S, $R_1$-T, $R_1$-U, $R_1$-V or $R_1$-W;

6. Compounds of Preferred 5 where
   X is $CH_3$, $OCH_3$, $OCH_2CH_3$, Cl, $OCF_2H$ or $OCH_2CF_3$; and
   Y is $CH_3$, $OCH_3$, $C_2H_5$, $CH_2OCH_3$, $NHCH_3$ or $CH(OCH_3)_2$.

7. Compounds of Preferred 6 where $R_1$ is F, Cl, Br, $NO_2$, $CH_3$, $CF_3$ $C_1$-$C_2$ alkoxy, allyloxy, $OC(Cl)=CHCl$, $CO_2CH_3$, $CO_2C_2H_5$, $CO_2NHCH_3$, $CO_2N(CH_3)_2$, $SO_2NHCH_3$ $SO_2N(CH_3)_2$, $SO_2CH_3$, $SO_2C_2H_5$, $OSO_2CH_3$, $OSO_2C_2H_5$, $R_1$-A, $R_1$-B or $R_1$-C.

Specifically preferred for reasons of greatest ease of synthesis and/or greatest herbicidal efficacy are:

4-(cyanomethyl)-2-[[4,6-dimethoxypyrimidin-2-yl)aminocarbonyl]aminosulfonyl]benzoic acid, methyl ester, m.p. 177°–179° C.; and 4-(cyanomethyl)-2-[[(4-methoxy-6-methyl-1,3,5-triazin-2-yl)aminocarbonyl]aminosulfonyl]benzoic acid, methyl ester, m.p. 160°–163° C.

DETAILED DESCRIPTION OF THE INVENTION

Synthesis

The compounds of Formula I can be prepared from sulfonamides of Formula II and heterocyclic amines of Formula III by one or more methods described in the literature.

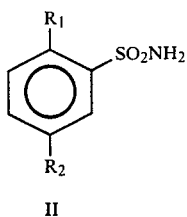   

II  III

Several representative routes are described below.

U.S. Pat. No. 4,394,506 (issued 7/19/83) teaches the conversion of sulfonamides to sulfonyl isocyanates and sulfonyl isothiocyanates, and their subsequent coupling with heterocyclic amines of Formula III to give sulfonylureas.

U.S. Pat. No. 4,398,939 (issued 8/16/83) teaches the formation of n-butylsulfonylureas from sulfonamides followed by phosgenation to give the sulfonyl isocyanates. Alternatively, the sulfonamides can be treated with thionyl chloride followed by phosgenation to afford the sulfonyl isocyanates. Additionally, methylcarbamate derivatives of compounds of Formula III react with sulfonamides in the presence of trimethylaluminum to give sulfonylureas.

U.S. Pat. No. 4,443,245 (issued 4/17/84) teaches two methods for the synthesis of sulfonylureas. Either a phenyl carbamate of a sulfonamide and a heterocyclic amine, or a sulfonamide and a phenyl carbamate of a heterocyclic amine couple to give a sulfonylurea in an inert solvent with base.

The preparation of sulfonamides from sulfonyl chlorides is widely reported in the literature; for reviews see: F. Hawking and J. S. Lawrence. "The Sulfonamides," H. K. Lewis and Co., London, 1950 and E. H. Northey, "The Sulfonamides and Allied Compounds," Reinhold Publishing Corp., New York, 1948.

Additionally, primary sulfonamides, such as those of Formula II, can be formed by removal of an N-t-butyl protecting group from the corresponding secondary sulfonamide with trifluoroacetic acid (J. D. Catt and W. L. Matier, J. Org. Chem., 39, 566 (1974)) or polyphosphoric acid (J. G. Lombardino, J. Org. Chem., 36 (1971), 1843).

The requisite sulfonyl chlorides may be synthesized by known methods or with slight modifications thereof, by one skilled in the art. Several representative teachings are listed below.

Aromatic nitro groups may be transformed into sulfonyl chlorides by reduction, diazotization and coupling with sulfur dioxide/cupric chloride as taught in U.S. Pat. No. 4,310,346 (issued 1/12/82).

European Publication No. 94,821 (published 11/23/83) describes the displacement of aromatic halides with thiolate anions and subsequent oxidative chlorination to yield sulfonyl chlorides.

Halogen-metal exchange of aromatic halides or proton-metal exchange of aromatics followed by quenching with sulfur dioxide gives sulfinate salts. These salts yield sulfonyl chlorides upon reaction with N-chlorosuccinimide as taught in U.S. Pat. No. 4,481,029 (issued 11/6/84). Directed proton-metal exchange of aromatic compounds has been reviewed by Gschwend and Rodriguez, Org. Reactions, 26 (1979), 1. Directed lithiation of aryl-N-t-butylsulfonamides is described by J. G. Lombardino, J. Org. Chem., 36 (1971), 1843. Also, aryllithiums may be converted directly to arylsulfonyl chlorides with sulfuryl chloride as described in S. N. Bhattacharya, et. al., J. Chem. Soc. C, (1968), 1265.

Electrophilic chlorsulfonation of an aromatic ring to give a sulfonyl chloride is well known in the literature. This technique works best for alkyl aryl ethers and alkyl aromatics. Its application is described by E. H. Huntress and F. H. Carten, J. Am. Chem. Soc., 62 (1940), 511-14 and 603-4.

Transformation of phenols to sulfonyl chlorides can be accomplished by the formation of a thiocarbamate, rearrangement, hydrolysis and oxidative chlorination as described by M. S. Newman and H. A. Karnes, J. Org. Chem., 31 (1966), 3980.

Compounds of Formula II can be prepared by a variety of methods known in the literature. The most universal scheme, where benzyl halides of Formula IV are reacted with the appropriate reagent, is shown below.

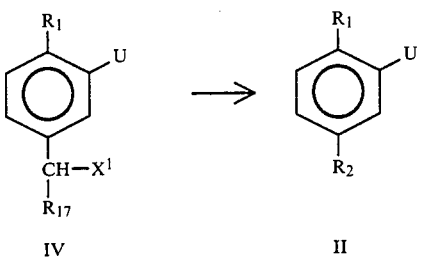

IV  II wherein U is $SO_2NH_2$ or a previously described sulfonamide precursor, and $X^1$ is Cl, Br or I and $R_2$ is of the structure $—CH(R_{17})—$. Some specific methods are listed below.

NITRILES ($R_2=CH(R_{17})CN$)

Nitriles can be prepared by nucleophilic displacement of benzyl halides, usually benzyl chlorides or bromides, with potassium or sodium cyanide. Many solvents are applicable, but frequently dimethylsulfoxide is used. Thus, a benzyl bromide of formula IV can be contacted with potassium cyanide in dimethylsulfoxide for 0.5 h to 24 h at 20° to 140° C. For a review of this reaction, refer to Friedrich and Wallenfels, in Rappoport, "The Chemistry of the Cyano Group", pp. 77–86, Interscience Publishers, New York, 1970.

ISONITRILES ($R_2=CH(R_{17})NC$)

Heavy metal cyanides and benzylhalides react to give isonitriles. The reaction is best carried out in the dark using silver cyanide and a benzyl iodide. Typical procedures are given by A. Gautier, Ann. Chem., 142 (1867), 28 and H. L. Jackson and B. C. McKusick, Org. Syn., Col. Vol. IV, 438.

AZIDES ($R_2=CH(R_{17})N_3$)

Compounds of Formula II may be prepared by reacting an azide anion with a benzyl halide. Typically sodium azide in alcohol or wet acetone is mixed with a benzyl bromide at 20°-100° C. This nucleophilic displacement is reviewed in Biffin, Miller and Paul, in Patai, "The Chemistry of the Azido Group," pp. 57-119, Interscience Pub., New York, 1971.

PHOSPHONATES ($R_2=CH(R_{17})P(O)R_{10}R_{11}$)

Alkyl phosphites are heated with benzylic halides to give phosphonates. The reaction is known as the Arbuzov reaction and it is reviewed by Arbuzov, *Pure Appl. Chem.*, 9 (1964), 307-335.

AMINES ($R_2=CH(R_{17})NR_{12}R_{13}$)

Tertiary amines are prepared by alkylation of a secondary amine with a benzylic halide. The reaction is well documented in the literature.

Primary amines can be prepared by reduction of compounds of Formula II where $R_2$ is azide. Generally lithium aluminum hydride or hydrogen and palladium catalyst are used.

NITRO ($R_2=CH(R_{17})NO_2$)

Nitrites react with benzylic halides to give benzylic nitro compounds. The reaction is usually carried out with sodium nitrite on a benzylic bromide in dimethylformamide or dimethylsulfoxide. When silver nitrite is used, diethyl ether at 0°-25° C. are the preferred reaction conditions. The reaction is exhaustively discussed by N. Kornblum, *Org. Reactions*, 12 (1962), 101.

SELENO ETHERS ($R_2=CH(R_{17})SeR_{14}$)

Alkali alkylselenides can be prepared by in situ combination of an alkali metal t-butoxide with the selenol $HSeR_{14}$ in the solvent to be used for the displacement reaction. The selenols, $HSeR_{14}$, can be prepared by a variety of methods reviewed by D. L. Klayman, "Selenols and their Derivatives" in *Organic Selenium Compounds: Their Chemistry and Biology*, D. L. Klayman, W. H. H. Gunther ed., New York, 1973, and K. J. Irgolic and M. V. Kudchadker, "Organic Chemistry of Selenium" in *Selenium*, R. A. Zingaro, W. C. Cooper ed., Van Nostrand Reinhold, New York, 1974.

Benzyl halides may be formed through a variety of methods described in the literature. Several are listed below.

BENZYLIC CHLORIDES ($X^1=Cl$)

Treatment of alkyl benzene derivatives with N-chlorosuccinimide, NCS, in a suitable solvent, such as carbon tetrachloride or dichloromethane, and catalyzed by light or a free radical initiator, such as azoisobutyronitrile or benzoyl peroxide, gives the benzylic chloride.

Treatment of a benzylic alcohol with thionyl chloride, either neat or in the presence of a base such as pyridine, gives the benzylic chloride. For typical examples, see H. Gilman and J. E. Kirby, *J. Am. Chem., Soc.*, 51, 3475 (1929) and M. S. Newman, *J. Am. Chem. Soc.*, 62, 2295 (1940).

BENZYLIC BROMIDES ($X^1=Br$)

Treatment of alkyl benzene derivatives with N-bromosuccinimide by a method analogous to the case of N-chlorosuccinimide gives the benzylic bromide. Benzylic alcohols in an inert solvent such as benzene or dichloromethane react with phosphorus tribromide to give benzylic bromides.

BENZYLIC IODIDES ($X^1=I$)

Treatment of a benzylic chloride or benzylic bromide with sodium iodide gives the benzylic iodide. The reaction, known as the Finkelstein reaction, works well in refluxing acetone.

Benzylic alcohols may be treated with iodine and phosphorus (red) or phosphorus (red) and phosphorus (yellow) to give the benzylic iodide.

Compounds of Formua II, where $R_2$ contains an oxygen functionality, such as an aldehyde or ketone, may be prepared by a variety of methods known to one skilled in the art. Two such routes are shown below.

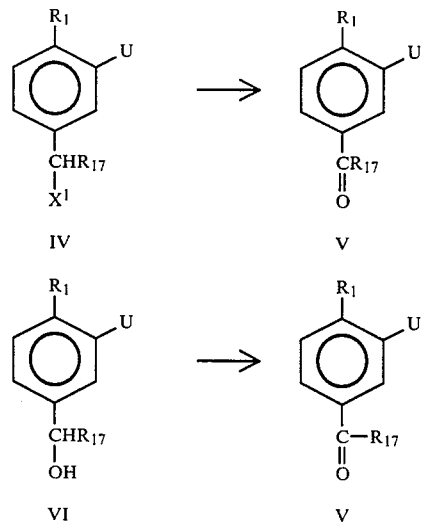

Primary and secondary benzylic halides may be oxidized to aldehydes and ketones, respectively using dimethylsulfoxide. For reviews of this reaction see Durst, *Adv. Org. Chem.*, 285-388 (1969) pp. 343-356 and W. Epstein and F. Sweat, *Chem. Rev.*, 67 (1967), 247-60.

Primary benzylic alochols may be oxidized to aldehydes and secondary benzylic alcohols may be oxidized to ketones by one skilled in the art. One or more of a variety of methods, such as an oxidizing agent, catalytic dehydrogenation, Oppenauer oxidation or halosuccinimide oxidation may be used.

Acetals, thioacetals, ketals and thioketals are easily prepared by one skilled in the art from compounds of Formula V.

Oximes, and oxime ethers of Formula Va are easily prepared by one skilled in the art from compounds of Formula V and hydroxylamine or o-alkyl-hydroxylamine with or without an appropriate base.

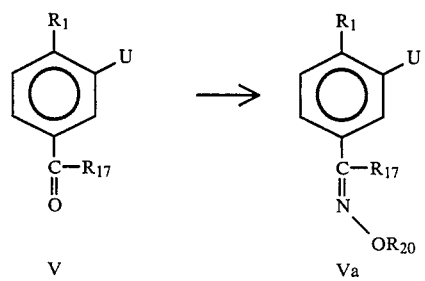

Benzylic alcohols and alkyl benzene derivatives are either known or may be prepared by one skilled in the art.

The heterocyclic amines A-1 to A-7 are either known, disclosed in this application or can be prepared by methods obvious to one skilled in the art.

For a review of the synthesis and reactions of 2-aminopyrimidines (A-1, Z=CH) see *The Chemistry of Heterocyclic Compounds,* Vol 16, Wiley-Interscience, New York (1962). For a review of the synthesis and reactions of 2-amino-1,3,5-triazines (A-1, Z=N) see *The Chemistry of Heterocyclic Compounds,* Vol. 13, Wiley-Interscience, New York (1959), F. C. Schaefer, U.S. Pat. No. 3,154,537 and F. C. Schaefer and K. R. Huffman *J. Org. Chem.,* 28 (1963), 1812.

The synthesis of bicyclic amines A-2 and A-3 is taught in U.S. Pat. No. 4,339,267.

The synthesis of amino furo[2,3-d]pyrimidines, A-4, is taught in U.S. Pat. No. 4,487,626.

The synthesis of aminotriazoles, A-5, is taught in U.S. Pat. No. 4,421,550.

The synthesis of aminomethylheterocycles, A-6, is taught in U.S. Pat. No. 4,496,392.

The synthesis of aminocyano heterocycles, A-7, is taught in European Publication No. 125,864 (published 11/21/84).

Agriculturally suitable salts of compounds of Formula I are also useful herbicides and can be prepared in a number of ways known to the art. For example, metal salts can be made by contacting copounds of Formula I with a solution of an alkali or alkaline earth metal salt having a sufficiently basic anion (e.g. hydroxide, alkoxide, carbonate or hydride). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following examples.

EXAMPLE 1

5-Bromomethyl-N-(1,1-dimethylethyl)-2-methoxybenzenesulfonamide

A mixture of 27 g of N-(1,1-dimethylethyl)-2-methoxy-5-methylbenzenesulfonamide (E. H. Huntress and F. H. Carten, *J. Am. Chem. Soc.,* 62 (1940), 603), 19.6 g NBS and 0.3 g azobisisobutyronitrile in 200 ml $CH_2Cl_2$ was refluxed and illuminated with a sun lamp. After 8 hours the lamp was turned off and the reaction was refluxed for another 24 hr. The reaction was allowed to cool. The reaction mixture was washed with 200 ml of a 1:1:1:1 mixture of brine:sodium sulfite:sodium bicarbonate:water. The organic layer was dried ($MgSO_4$), treated with charcoal and filtered through a 5 g plug of silica gel. The plug was washed with 100 ml of chloroform. The combined organic fractions were evaporated to give 34 g of solid, m.p. 137°–142° C.

NMR ($CDCl_3$, 200 MHz)δ: 1.15 (s, $CH_3$, 9H), 4.0 (s, $OCH_3$, 3H), 4.45 (s, $CH_2$, 2H), 4.95 (bs, NH, 1H), 7.0–8.6 (m, ArH, 3H).

EXAMPLE 2

5-Cyanomethyl-N-(1,1-dimethylethyl)-2-methoxybenzenesulfonamide

A mixture of 1.63 g potassium cyanide and 8 g of the compound from Example 1 in 50 ml of DMSO was stirred at room temperature overnight. The solution became darker in color with time, going from orange to purple to black. After being stirred overnight the reaction mixture was partitioned between ethyl acetate and water. The organic layer was washed with brine, dried ($MgSO_4$), filtered and the solvent evaporated. The residual red oil was eluted through a dry silica column with 20% ethyl acetate-80% dichloromethane. The product band was isolated to give 3.0 g solid m.p. 146°–147° C.

NMR ($CDCl_3$, 90 MHz): 1.1 (s, $CH_3$, 9H), 3.7 (s, $CH_2CN$, 2H), 4.0 (s, $OCH_3$, 3H), 5.0 (s, NH, 1H), 6.9–8.0 (m, ArH, 3H).

EXAMPLE 3

5-Cyanomethyl-2-methoxybenzenesulfonamide

A suspension of 3.0 g of the compound from Example 2 and 0.1 g p-toluenesulfonic acid in 100 ml of dry toluene was refluxed in a flask equipped with a Dean-Stark apparatus. After being refluxed overnight the solution was concentrated and allowed to cool. The precipitate was filtered off to give 0.5 g light brown solid. The mother liquor was chromatographed over silica gel with 20:73:2:5, ethyl acetate:methylene chloride:methanol:THF to give additional product, m.p. 173°–177° C.

NMR ($DMSO-d_6$, 90 MHz)δ: 3.9 (s, $OCH_3$, 3H), 4.0 (s, $CH_2CN$, 2H), 7.1 (bs, $NH_2$, 2H), 7.2–7.8 (m, ArH, 3H).

EXAMPLE 4

5-(Cyanomethyl)-N-((4,6-dimethoxy-pyrimidin-2-yl)aminocarbonyl)-2-methoxybenzenesulfonamide To a suspension of 0.3 g of the compound from Example 3 and 0.37 g 4,6-dimethoxy-2-pyrimidinylcarbamic acid, phenyl ester in 15 ml of dry acetonitrile was added 0.198 ml DBU. After being stirred overnight the clear solution was diluted with 50 ml of water, acidified with 1N HCl and the precipitate was filtered off. The residue was washed with water and triturated with ether to give 0.44 g solid, m.p. 168°–171° C. (dec.).

IR (nujol) 1711 cm$^{-1}$. NMR (200 MHz, DMSO-d$_6$)δ: 3.76 (s, OCH$_3$, 3H), 3.91 (s, OCH$_3$, 6H), 4.10 (s, CH$_2$, 2H) 6.02 (s, Het-H, 1H), 7.2–7.9 (m, ArH, 3H), 10.5+12.8 (S, NH, 2×1H).

EXAMPLE 5

5-(Bromomethyl)-2-carboxymethylbenzenesulfonamide

A solution of 3.5 g (0.0153 mole) of 5-methyl-2-carboxymethylbenzenesulfonamide, 2.86 g N-bromosuccinimide, 0.05 g azobisisobutyronitrile in 50 ml of carbon tetrachloride and 50 ml dichloromethane was prepared under a nitrogen atmosphere. The solution was refluxed and irradiated with a sun lamp for 4 h. Then 0.6 g N-bromosuccinimide was added. After three hours of further irradiation the reaction was cooled and filtered to give 4.7 g of a white solid. The solid was washed with 200 ml of dichloromethane to leave 1.0 g of product. The mother liquor was eluted through a dry silica gel column with 5% diethyl ether/95% dichloromethane to give an additional 2.3 g of product, m.p. 171°–173° C.

NMR (CDCl$_3$, 200 MHz)δ: 4.0 (s, OCH$_3$, 3H), 4.52 (s, CH$_2$Br, 2H) 5.76 (s, NH$_2$, 2H), 7.6–8.2 (m, ArH, 3H).

EXAMPLE 6

5-(Cyanomethyl)-2-carboxymethylbenzenesulfonamide

To a solution of 0.31 g potassium cyanide in 20 ml of dry dimethylsulfoxide was added 1.4 g (4.55 mmol) of the compound from Example 5. After being stirred for 6 h, the reaction mixture was partitioned between ethyl acetate and water. The water layer was neutralized to pH 7, the layers separated and the organic layer was dried (MgSO$_4$). This solution was placed on a dry silica gel column and eluted with 40% ethyl acetate/60% hexane followed by 60% ethyl acetate/40% hexane. The product band (R$_f$0.5, 60% ethyl acetate/40% hexane) was extracted with ethyl acetate, concentrated and the residue triturated with diethyl ether to give 0.26 g of a solid, m.p. 125°–129° C.

MS (m/e) 254 (M+). IR (Nujol) 1711 cm$^{-1}$.

NMR (200 MHz, DMSO-d$_6$)δ: 3.82 (s, OCH$_3$), 4.24 (s, CH$_2$CN), 7.36 (s, NH$_2$), 7.65 (dd, ArH, 2H), 7.95 (s, ArH, 1H).

EXAMPLE 7

4-(Cyanomethyl)-2-[((4,6-dimethoxypyrimidin-2-yl)aminocarbonyl)aminosulfonyl]benzoic acid, methyl ester To a suspension of 0.12 g of the compound from Example 6 and 0.143 g of 4,6-dimethoxy-2-pyrimidinylcarbamic acid, phenyl ester in 15 ml of dry acetonitrile was added 72.7 μl of 1,8-diazabicyclo[5.4.0]undec-7-ene (DBU). After being stirred at room temperature for one hour, the reaction mixture was diluted with 50 ml of water, acidified with 1N hydrochloric acid to pH 2 and extracted with ethyl acetate. The organic solution was dried (MgSO$_4$), filtered and concentrated to an oil. Trituration of the residue with 3:1 (ethyl ether:acetonitrile) gave 0.16 g of a white solid, m.p. 177°–179° C.

IR (nujol) 1725 cm$^{-1}$.

NMR (DMSO-d$_6$, 200 MHz)δ: 3.78 (s, OCH$_3$, 3H), 3.92 (s, OCH$_3$, 6H), 4.31 (s, CH$_2$, 2H), 6.01 (S, Het-H, 1H), 7.7–8.2 (m, ArH, 3H), 10.6 and 12.7 (two s, NH, 2×1H).

EXAMPLE 8

5-Acetyl-2-ethoxybenzenesulfonamide

To a solution of 30.6 g of 4-ethoxyacetophenone in 100 ml of chloroform was added 40 ml of chlorosulfonic acid dropwise. The reaction was then reluxed for five hours after which it was poured into 800 ml of ice water. The reaction mixture was extracted with 400 ml of chloroform. The organic layer was washed with brine, dried (MgSO$_4$) and filtered through charcoal. The filtrate was concentrated under reduced essure to give 12.3 g of an oil. The oil was dissolved in 200 ml tetrahydrofuran. The solution was cooled to 5° C. followed by dropwise addition of 10 ml of concentrated ammonium hydroxide. After stirring overnight at room temperature, the reaction was partitioned between water and ethyl acetate. The organic layer was washed with 1N hydrochloric acid, brine, dried (MgSO$_4$), filtered and stripped. The residue was crystallized from acetonitrile/diethyl ether. The solid was washed with methanol and dried to give 2.3 g of solid, m.p. 148°–151° C.

NMR (90 MHz, CDCl$_3$)δ: 1.5 (m, CH$_3$, 3H), 2.55 (s, CH$_3$, 3H), 4.35 (q, CH$_2$O, 2H), 5.1 (bs, NH$_2$), 7.0–8.6 (m, ArH, 3H).

EXAMPLE 9

5-Acetyl-N-((4,6-dimethoxypyrimidin-2-yl)aminocarbonyl)-2-ethoxybenzenesulfonamide To a stirred suspension of 0.2 g of the compound from Example 8, 0.23 g of 4,6-dimethoxy-2-pyrimidinylcarbamic acid, phenyl ester in 10 ml of dry acetonitrile was added 127 μl of DBU. After being stirred for 1 hr, the mixture was treated with 40 ml of water and 1N HCl in a dropwise manner until the pH was 3. The precipitate was filtered off and washed with water and ether/hexane (1/1), to give 0.27 g of a solid, m.p. 192°–193° C.

IR (nujol) 1680 and 1705 cm$^{-1}$.

NMR (200 MHz, DMSO-d$_6$)δ: 1.1 (t, CH$_3$, 3H), 2.58 (s, CH$_3$, 3H), 3.91 (s, OCH$_3$, 6H), 4.27 (q, CH$_2$, 2H), 6.03 (s, Het-H, 1H), 7.2–8.4 (m, ArH, 3H), 10.6 and 12.7 (s, NH, 2×1H).

The invention is further exemplified, but not limited to the compounds in Tables I–VII. The compounds depicted in these tables may be prepared by methods described in Examples 1–9, or by modifications thereof apparent to those skilled in the art.

General Structures

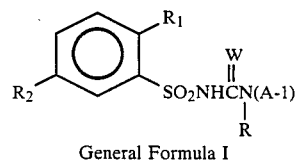

General Formula I

-continued
General Structures

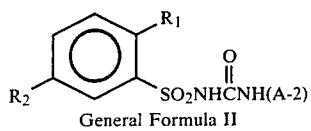
General Formula II

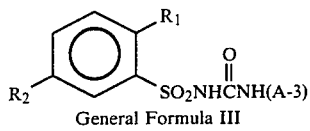
General Formula III

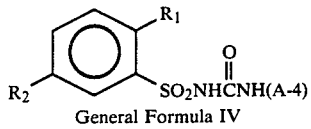
General Formula IV

-continued
General Structures

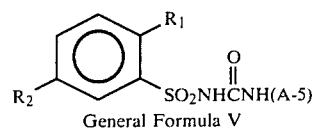
General Formula V

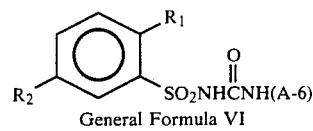
General Formula VI

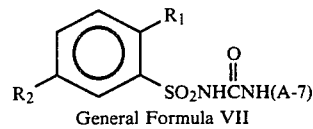
General Formula VII

TABLE I

General Formula I

| $R_1$ | $R_2$ | W | R | X | Y | Z | m.p. (°C.) |
|---|---|---|---|---|---|---|---|
| F | $CH_2CN$ | O | H | $OCH_3$ | H | CH | |
| F | $CH_2CN$ | O | $CH_3$ | $OCH_3$ | $CH_3$ | CH | |
| F | $CH_2CN$ | O | H | $CH_3$ | $OCH_3$ | N | |
| F | $CH_2SCN$ | O | H | $OCH_3$ | $OCH_3$ | CH | |
| F | $CH_2SCN$ | O | H | $OCH_3$ | $CH_2CH_3$ | CH | |
| F | $CH_2SCN$ | O | H | $CH_2CH_3$ | $OCH_3$ | N | |
| F | $CH_2P(O)(OCH_3)_2$ | O | H | $OCH_3$ | $CH_2OCH_3$ | CH | |
| F | $CH_2P(O)(OCH_3)_2$ | O | H | $OCH_3$ | $OCH_3$ | CH | |
| F | $CH_2P(O)(OCH_3)_2$ | O | H | $OCH_2CH_3$ | $CH_3$ | CH | |
| F | $CH_2P(O)(CH_3)_2$ | O | H | $OCH_3$ | $CH_3$ | N | |
| Cl | $CH_2CN$ | O | H | $OCH_3$ | $CH_2CH_2OCH(CH_3)_2$ | CH | |
| Cl | $CH_2CN$ | O | H | Cl | $OCH_3$ | CH | |
| Cl | $CH_2CN$ | O | H | $OCH_3$ | $CH(CH_3)(CH_2OCH_3)$ | CH | |
| Cl | $CH_2SCN$ | O | H | CH | $CH_3$ | $CH_3$ | 143–153 |
| Cl | $CH_2SCN$ | O | H | $OCH_3$ | $CH_3$ | N | 100–106 |
| Cl | $CH_2SCN$ | O | H | $OCH_3$ | $CH_3$ | CH | 174–180 |
| Cl | $CH_2SCN$ | O | H | Cl | $OCH_3$ | CH | oil |
| Cl | $CH_2SCN$ | O | H | $OCH_3$ | $OCH_3$ | N | oil |
| Cl | $CH_2SCN$ | O | H | $OCH_3$ | $(CH_2)_4CH_2OCH_2CH_3$ | CH | |
| Cl | $CH_2P(O)(OCH_3)_2$ | O | H | $OCH_3$ | $CH_3$ | N | |
| Cl | $CH_2P(O)(OCH_3)_2$ | O | H | $OCF_2H$ | $CH_3$ | CH | |
| Cl | $CH_2P(O)(OCH_3)_2$ | O | H | $OCH_3$ | $NH_2$ | CH | |
| Cl | $CH_2P(O)(OCH_2CH_3)_2$ | O | H | $OCH_3$ | $NHCH_3$ | N | |
| Br | $CH_2CN$ | O | H | $CH_3$ | $NHCH_2CH_3$ | CH | |
| Br | $CH_2CN$ | O | H | $OCH_3$ | $OCH_3$ | CH | |
| Br | $CH_2CN$ | S | H | $OCH_3$ | $CH_3$ | N | |
| Br | $CH_2SCN$ | O | H | $CH_2F$ | $OCH_3$ | CH | |
| Br | $CH_2SCN$ | O | H | $OCH_3$ | $NHCH(CH_3)_2$ | CH | |
| Br | $CH_2SCN$ | O | H | $OCH_3$ | $CH_3$ | N | |
| Br | $CH_2P(O)(OCH_3)_2$ | O | H | $OCH_2CH_2F$ | $OCH_3$ | CH | |
| Br | $CH_2P(O)(OCH_3)_2$ | O | H | $OCH_3$ | $N(CH_3)_2$ | CH | |
| Br | $CH_2P(O)(SCH_3)_2$ | O | H | $OCH_3$ | $OCH_3$ | N | |
| $NO_2$ | $CH_2CN$ | O | H | $OCH_3$ | $OCH_3$ | CH | |
| $NO_2$ | $CH_2CN$ | O | H | $OCH_3$ | $CH_3$ | CH | |
| $NO_2$ | $CH_2CN$ | O | H | $CH_3$ | $OCH_3$ | CH | |
| $NO_2$ | $CH_2SCN$ | O | H | $OCH_3$ | $CH_2CH_2CH_2CH_3$ | N | |
| $NO_2$ | $CH_2SCN$ | O | H | $CH_2CH_3$ | $OCH_3$ | CH | |
| $NO_2$ | $CH_2SCN$ | O | H | $OCH_3$ | $OCH_2CH_2CH_2Cl$ | CH | |
| $NO_2$ | $CH_2P(O)(OCH_3)_2$ | O | H | $OCH_3$ | $OCH_3$ | N | |
| $NO_2$ | $CH_2P(O)(OCH_3)_2$ | O | H | $CH_2CH_2CH_2CH_3$ | $OCH_3$ | CH | |
| $NO_2$ | $CH_2P(O)(OCH_3)_2$ | O | H | $OCH_3$ | $SCH_2CH_2F$ | CH | |
| $NO_2$ | $CH_2P(S)(SCH_3)_2$ | O | H | $OCH_3$ | $OCH_3$ | N | |
| $CH_3$ | $CH_2CN$ | O | H | $CH_3$ | $SCH_3$ | CH | |
| $CH_3$ | $CH_2CN$ | O | H | $OCH_3$ | $OCH_3$ | CH | |
| $CH_3$ | $CH_2SCN$ | O | H | $OCH_3$ | $SCH(CH_3)_2$ | N | |
| $CH_3$ | $CH_2SCN$ | O | H | $OCH_2CH(CH_3)_2$ | $OCH_3$ | CH | |
| $CH_3$ | $CH_2P(O)(OCH_3)_2$ | O | H | Br | $OCH_3$ | CH | |
| $CH_3$ | $CH_2P(O)(N(CH_3)_2)_2$ | O | H | $OCH_3$ | $OCH_3$ | N | |
| $CH_2CH_3$ | $CH_2CN$ | O | H | $CH_2CH_2OCH_2CH_2CH_3$ | $OCH_3$ | CH | |
| $CH_2CH_3$ | $CH_2SCN$ | O | H | $OCH_3$ | $OCH_2CH_2OCH_3$ | CH | |
| $n$-$C_4H_9$ | $CH_2P(O)(OCH_3)_2$ | O | H | $OCH_3$ | $OCH_3$ | N | |
| $CH=CH_2$ | $CH_2CN$ | O | H | F | $OCH_3$ | CH | |

TABLE I-continued
General Formula I

| R₁ | R₂ | W | R | X | Y | Z | m.p. (°C.) |
|---|---|---|---|---|---|---|---|
| CH=CHCH₃ | CH₂CN | O | H | OCH₃ | OCH₃ | CH | |
| CH₂CH=CH₂ | CH₂SCN | O | H | CH₃ | OCH₃ | N | |
| CCl=CCl₂ | CH₂SCN | O | H | OCH₂CH₂OCH(CH₃)₂ | OCH₃ | CH | |
| C≡CCH₃ | CH₂P(O)(OCH₃)₂ | O | H | CH₃ | OCH₃ | CH | |
| CH₂C≡CH | CH₂CN | O | H | OCH₃ | CH₂CH₃ | N | |
| CH₂Cl | CH₂CN | O | H | N(CH₂CH₃)₂ | OCH₃ | CH | |
| CH₂Cl | CH₂SCN | O | H | Cl | OCH₃ | CH | |
| CH₂Br | CH₂P(O)(OCH₃)₂ | O | H | OCH₃ | OCH₃ | N | |
| CH₂Br | CH₂CN | O | H | CH₃ | OCH₃ | CH | |
| CF₃ | CH₂CN | O | H | OCH₃ | CH₃ | N | |
| CF₃ | CH₂CN | O | H | OCH₃ | OCH₃ | CH | |
| CF₃ | CH₂SCN | O | H | Br | OCH₃ | CH | |
| CF₃ | CH₂SCN | O | H | OCH₃ | CH₂CH₂ | N | |
| CF₃ | CH₂P(O)(OCH₃)₂ | O | H | OCH₃ | OCH₃ | CH | |
| CF₃ | CH₂P(O)(OCH₃)₂ | O | H | OCH₂CH₃ | CH₃ | CH | |
| CF₃ | CH₂NH₂ | O | H | OCH₃ | H | CH | |
| CH₂CHClCH₂Cl | CH₂CN | O | H | CH₃ | OCH₃ | N | |
| CH₂CF₃ | CH₂CN | O | H | I | OCH₃ | CH | |
| OCH₃ | CH₂CN | O | H | OCH₃ | CH₂OCH₃ | CH | |
| OCH₃ | CH₂CN | O | H | CH₃ | OCH₃ | CH | |
| OCH₃ | CH₂CN | O | H | CH₃ | OCH₃ | N | 166–170° |
| OCH₃ | CH₂CN | O | H | OCH₃ | NHCH₃ | CH | |
| OCH₃ | CH₂CN | O | H | OCH₃ | OCH₃ | N | |
| OCH₃ | CH₂CN | O | H | OCH₂CF₂H | OCH₃ | CH | |
| OCH₃ | CH₂CN | O | H | OCH₃ | OCH₃ | CH | 168–171° |
| OCH₃ | CH₂CN | O | H | CH₃ | CH₃ | N | |
| OCH₃ | CH₂SCN | O | H | CH₂Br | OCH₃ | CH | |
| OCH₃ | CH₂SCN | O | H | CH₃ | OCH₃ | CH | |
| OCH₃ | CH₂SCN | O | H | OCH₃ | N(CH₃)₂ | N | |
| OCH₃ | CH₂SCN | O | H | OCH₃ | OCH₃ | CH | |
| OCH₃ | CH₂SCN | O | H | CH₃ | OCH₃ | CH | |
| OCH₃ | CH₂SCN | O | H | OCH₃ | SCH₃ | N | |
| OCH₃ | CH₂P(O)(OCH₃)₂ | O | H | OCH₂CF₃ | CH₃ | CH | |
| OCH₃ | CH₂P(O)(OCH₃)₂ | O | H | OCH₃ | CF₃ | CH | |
| OCH₃ | CH₂P(O)(OCH₃)₂ | O | H | OCH₃ | OCH₃ | N | |
| OCH₃ | CH₂P(O)(OCH₃)₂ | O | H | CH₂Cl | CH₃ | CH | |
| OCH₃ | CH₂P(O)(OCH₃)₂ | O | H | OCH₃ | OCH₃ | CH | |
| OCH₃ | CH₂P(O)(OCH₃)₂ | O | H | OCH₃ | CH₃ | CH | |
| OCH₃ | CH₂P(O)(OCH₃)₂ | O | H | OCH₃ | CH₃ | CH | |
| OCH₃ | CH₂P(O)(OCH₃)₂ | O | H | Cl | OCH₃ | CH | |
| OCH₃ | CH₂N(CH₃)₂ | O | H | OCH₃ | OCH₃ | CH | |
| OCH₃ | CH₂N(CH₃)₂ | O | H | OCH₃ | CH₃ | CH | |
| OCH₃ | CH₂N(CH₃)₂ | O | H | CH₃ | CH₃ | CH | |
| OCH₃ | CH₂N(CH₃)₂ | O | H | Cl | OCH₃ | CH | |
| OCH₃ | CH₂N(CH₃)₂ | O | H | OCH₃ | OCH₃ | N | |
| OCH₃ | CH₂N(CH₃)₂ | O | H | OCH₃ | CH₃ | N | |
| OCH₃ | CH₂SeCH₃ | O | H | OCH₃ | OCH₃ | CH | 135–138 |
| OCH₃ | CH₂SeCH₃ | O | H | OCH₃ | CH₃ | CH | 101–110 |
| OCH₃ | CH₂SeCH₃ | O | H | Cl | OCH₃ | CH | |
| OCH₃ | CH₂SeCH₃ | O | H | CH₃ | CH₃ | CH | 101–103 |
| OCH₃ | CH₂SeCH₃ | O | H | OCH₃ | OCH₃ | N | 101–105 |
| OCH₃ | CH₂SeCH₃ | O | H | OCH₃ | CH₃ | N | 120–127 |
| OCH₃ | CH₂SeCH₃ | O | H | OCH₂CH₃ | NHCH₃ | N | |
| OCH₃ | CH₂N₃ | O | H | OCH₃ | OCH₃ | CH | 142–144 |
| OCH₃ | CH₂N₃ | O | H | OCH₃ | CH₃ | CH | 129–132 |
| OCH₃ | CH₂N₃ | O | H | Cl | OCH₃ | CH | 144–146 |
| OCH₃ | CH₂N₃ | O | H | CH₃ | CH₃ | CH | 137–142 |
| OCH₃ | CH₂N₃ | O | H | OCH₃ | OCH₃ | N | 137–142 |
| OCH₃ | CH₂N₃ | O | H | OCH₃ | CH₃ | N | 96–101 |
| OCH₃ | CH₂NO₂ | O | H | OCH₃ | OCH₃ | CH | |
| OCH₃ | CH₂NO₂ | O | H | OCH₃ | CH₃ | CH | |
| OCH₃ | CH₂NO₂ | O | H | Cl | OCH₃ | CH | |
| OCH₃ | CH₂NO₂ | O | H | CH₃ | CH₃ | CH | |
| OCH₃ | CH₂NO₂ | O | H | OCH₃ | OCH₃ | N | |
| OCH₃ | CH₂NO₂ | O | H | OCH₃ | CH₃ | N | |
| OCH₃ | CH₂NC | O | H | OCH₃ | OCH₃ | CH | |
| OCH₃ | CH₂NC | O | H | OCH₃ | CH₃ | CH | |
| OCH₂CH₃ | CH₂CN | O | H | OCH₃ | OCH₃ | CH | |
| OCH₂CH₃ | CH₂SCN | O | H | OCH₃ | SCH₃ | CH | |
| OCH₂CH₃ | CH₂SCN | O | H | OCH₃ | OCH₃ | CH | |
| OCH₂CH₃ | CH₂P(O)(OCH₃)₂ | O | H | OCH₃ | OCH₃ | N | |
| OCH₂CH₃ | CH₂P(O)(OCH₃)₂ | O | H | CH₃ | OCH₂CH=CH₂ | N | |
| OCH₂CH₃ | CH₂N₃ | O | H | OCH₃ | OCH₃ | CH | |
| OCH₂CH₃ | CH₂NO₂ | O | H | OCH₃ | OCH₃ | CH | |
| OCH₂CH₃ | CH₂N(CH₃)₂ | O | H | OCH₃ | CH₃ | N | |
| OCH(CH₃)₂ | CH₂CN | O | H | CH₃ | OCH₃ | CH | |
| o-n-C₄H₉ | CH₂CN | O | H | OCH₃ | OCH₃ | CH | |
| OCH₂CH₂OCH₃ | CH₂CN | O | H | OCH₃ | OCH₂C≡CH | N | |
| OCH₂CH₂OCH₃ | CH₂CN | O | H | OCH₃ | CH₃ | CH | |

TABLE I-continued

General Formula 1

| R₁ | R₂ | W | R | X | Y | Z | m.p. (°C.) |
|---|---|---|---|---|---|---|---|
| OCH₂CH₂OCH₃ | CH₂SCN | O | H | OCH₃ | OCH₃ | CH | |
| OCH₂CH₂OCH₃ | CH₂SCN | O | H | OCH₃ | OCH₃ | N | |
| OCH₂CH₂OCH₃ | CH₂SCN | O | H | CH₃ | OCH₂CH₂OCH₃ | CH | |
| OCH₂CH₂OCH₃ | CH₂P(O)(OCH₃)₂ | O | H | OCH₃ | CH₃ | CH | |
| OCH₂CH₂OCH₃ | CH₂P(O)(OCH₃)₂ | O | H | OCH₃ | OCH₃ | N | |
| OCH₂CH₂OCH₃ | CH₂NH(CH₂CH₂CH₃) | O | H | OCH₃ | OCH₃ | CH | |
| OCF₂H | CH₂CN | O | H | OCH₃ | CH₃ | CH | |
| OCF₂H | CH₂CN | O | H | CH₃ | OCH₃ | N | |
| OCF₂H | CH₂SCN | O | H | OCH₃ | CH₂SCH₃ | CH | |
| OCF₂H | CH₂SCN | O | H | OCH₃ | CH₃ | N | |
| OCF₂H | CH₂P(O)(OCH₃)₂ | O | H | OCH₃ | CH₃ | CH | |
| OCF₂H | CH₂P(O)(OCH₃)₂ | O | H | OCH₃ | OCH₃ | CH | |
| OCF₂H | CH₂N(CH₂CH₃)₂ | O | H | OCH₃ | OCH₃ | N | |
| OCF₂H | CH₂N(CH₃)₂ | O | H | CH₃ | CH₃ | CH | |
| OCH₂CH₂F | CH₂CN | O | H | OCH₃ | OCH₃ | CH | |
| OCH₂CH₂F | CH₂CN | O | H | OCH₃ | OCH₃ | N | |
| OCH₂CF₃ | CH₂CN | O | H | OCH₃ | CH₃ | CH | |
| OCH₂CH₂Cl | CH₂CN | O | H | OCH₃ | OCH₃ | CH | |
| OCH₂CH₂Cl | CH₂CN | O | H | OCH₃ | CH₃ | CH | |
| OCH₂CH₂Cl | CH₂SCN | O | H | CH₃ | OCH₃ | CH | |
| OCH₂CH₂Cl | CH₂SCN | O | H | OCH₃ | CH₂CH₂OCH₂CH₃ | N | |
| OCH₂CH₂Cl | CH₂SCN | O | H | CH₂CH₃ | OCH₃ | CH | |
| OCH₂CH₂Cl | CH₂P(O)(OCH₃)₂ | O | H | I | OCH₃ | CH | |
| OCH₂CH₂Cl | CH₂P(O)(OCH₃)₂ | O | H | OCH₃ | OCH₃ | N | |
| OCH₂CH₂Cl | CH₂SeCH₃ | O | H | CH₃ | OCH₃ | CH | |
| OCH₂CH=CH₂ | CH₂CN | O | H | OCH₃ | NH₂ | CH | |
| OCH₂CH=CH₂ | CH₂CN | O | H | OCH₃ | OCH₃ | N | |
| OCH₂CH=CH₂ | CH₂CN | O | H | CH₃ | NHCH₂CH₂CH₃ | CH | |
| OCH₂CH=CH₂ | CH₂CN | O | H | OCH₃ | OCH₃ | CH | |
| OCH₂CH=CH₂ | CH₂SCN | O | H | OCH₃ | OCH₃ | N | |
| OCH₂CH=CH₂ | CH₂SCN | O | H | CH₃ | OCH₃ | CH | |
| OCH₂CH=CH₂ | CH₂P(O)(OCH₃)₂ | O | H | OCH₃ | OCH₂C≡CH | CH | |
| OCH₂CH=CH₂ | CH₂SeCH₂CH₃ | O | H | OCH₃ | OCH₃ | N | |
| OCH₂C≡CH | CH₂CN | O | H | CH₂C₃ | OCH₃ | CH | |
| OCH₂C≡CH | CH₂CN | O | H | OCH₃ | OCH₂CH₂CH₂=CH₃ | CH | |
| OCH₂C≡CH | CH₂CN | O | H | OCH₃ | OCH₃ | N | |
| OCH₂C≡CH | CH₂SCN | O | H | CH₃ | CH₂SCH₃ | CH | |
| OCH₂C≡CH | CH₂SCN | O | H | OCH₃ | OCH₃ | CH | |
| OCH₂C≡CH | CH₂SCN | O | H | CH₃ | OCH₃ | N | |
| OCH₂C≡CH | CH₂P(O)(OCH₃)₂ | O | H | OCH₃ | CH₂SCH₂CH₂CH₂ | CH | |
| OCH₂C≡CH | CH₂P(O)(OCH₃)₂ | O | H | CH₃ | OCH₃ | CH | |
| OC(Cl)=CHCl | CH₂CN | O | H | OCH₃ | CH₂CH₂F | N | |
| OC(Cl)=CHCl | CH₂CN | O | H | I | OCH₃ | CH | |
| OC(Cl)=CHCl | CH₂SCN | O | H | OCH₃ | OCH₂C≡CH | CH | |
| OC(Cl)=CHCl | CH₂P(O)(OCH₃)₂ | O | H | OCH₃ | C≡CH | N | |
| OC(Cl)=CHCl | CH₂P(O)(OCH₃)₂ | O | H | CH₃ | OCH₃ | CH | |
| CO₂CH₃ | CH₂CN | O | H | OCH₃ | OCH₃ | CH | 177–179 |
| CO₂CH₃ | CH₂CN | O | H | OCH₃ | CH₃ | CH | 172–175 |
| CO₂CH | CH₂CN | O | H | CH₃ | CH₃ | CH | 174–177 |
| CO₂CH₃ | CH₂CN | O | H | CH₂CH₃ | OCH₃ | CH | |
| CO₂CH₃ | CH₂CN | O | H | OCH₃ | CH₃ | N | 160–163 |
| CO₂CH₃ | CH₂CN | O | H | CH₂CH₂ | OCH₃ | CH | |
| CO₂CH₃ | CH₂CN | O | H | Cl | OCH₃ | CH | 181–185 |
| CO₂CH₃ | CH₂CN | O | H | OCH₃ | OCH₃ | N | 126–132 |
| CO₂CH₃ | CH₂SCN | O | H | CH₃ | OCH₃ | CH | |
| CO₂CH₃ | CH₂SCN | O | H | Cl | OCH₃ | CH | |
| CO₂CH₃ | CH₂SCN | O | H | OCH₃ | OCH₃ | N | |
| CO₂CH₃ | CH₂SCN | O | H | CH₃ | CH₃ | CH | |
| CO₂CH₃ | CH₂SCN | O | H | OCH₃ | OCH₃ | CH | 126 |
| CO₂CH₃ | CH₂SCN | O | H | OCH₃ | CH₃ | N | |
| CO₂CH₃ | CH₂SCN | O | H | NHCH₃ | OCH₃ | CH | |
| CO₂CH₃ | CH₂SCN | O | H | OCH₃ | CH(OCH₃)₂ | CH | |
| CO₂CH₃ | CH₂P(O)(OCH₃)₂ | O | H | OCH₃ | OCH₃ | N | oil |
| CO₂CH₃ | CH₂P(O)(OCH₃)₂ | O | H | CH₃ | OCH₃ | CH | oil |
| CO₂CH₃ | CH₂P(O)(OCH₃)₂ | O | H | CH₃ | CH₃ | CH | oil |
| CO₂CH₃ | CH₂P(O)(OCH₃)₂ | O | H | OCH₃ | CH₃ | N | oil |
| CO₂CH₃ | CH₂P(O)(OCH₃)₂ | O | H | cyclopropyl | OCH₃ | CH | |
| CO₂CH₃ | CH₂P(O)(OCH₃)₂ | O | H | OCH₃ | OCH₃ | CH | oil |
| CO₂CH₃ | CH₂P(O)(OCH₃)₂ | O | H | CH₃ | OCH₂CF₃ | N | |
| CO₂CH₃ | CH₂P(O)(OCH₃)₂ | O | H | CH₃ | CH₃ | CH | |
| CO₂CH₃ | CH₂P(S)(SCH₃)₂ | O | H | CH₃ | OCH₃ | CH | |
| CO₂CH₃ | CH₂P(O)(SCH₃)₂ | O | H | OCH₃ | OCH₃ | N | |
| CO₂CH₃ | CH₂NH₂ | O | H | cyclopropyl | OCH₃ | CH | |
| CO₂CH₃ | CH₂NH₂ | O | H | Cl | OCH₃ | CH | |
| CO₂CH₃ | CH₂NH₂ | O | H | OCH₃ | OCH₃ | N | |
| CO₂CH₃ | CH₂NH₂ | O | H | CH₃ | OCH₃ | CH | |
| CO₂CH₃ | CH₂N(CH₃)₂ | O | H | OCH₃ | OCH₃ | CH | |

TABLE I-continued

General Formula I

| R₁ | R₂ | W | R | X | Y | Z | m.p. (°C.) |
|---|---|---|---|---|---|---|---|
| CO₂CH₃ | CH₂N(CH₃)₂ | O | H | OCH₃ | CH₃ | CH | |
| CO₂CH₃ | CH₂N(CH₃)₂ | O | H | CH₃ | OCH₃ | N | |
| CO₂CH₃ | CH₂N(CH₃)₂ | O | H | OCH₃ | OCH₃ | N | |
| CO₂CH₃ | CH₂N(CH₃)₂ | O | H | CH₂CH₃ | OCH₃ | CH | |
| CO₂CH₃ | CH₂N(CH₃)₂ | O | H | Cl | OCH₃ | CH | |
| CO₂CH₃ | CH₂N(CH₃)(CH₂CH₃) | O | H | OCH₃ | OCH₃ | N | |
| CO₂CH₃ | CH₂NH(CH(CH₃)₂) | O | H | CH₃ | OCH₃ | CH | |
| CO₂CH₃ | CH₂SeCH₃ | O | H | OCH₃ | CH₃ | CH | |
| CO₂CH₃ | CH₂SeCH₃ | O | H | OCH₃ | OCH₃ | N | |
| CO₂CH₃ | CH₂SeCH₃ | O | H | CH₃ | CH₃ | CH | |
| CO₂CH₃ | CH₂SeCH₃ | O | H | OCH₃ | OCH₃ | CH | |
| CO₂CH₃ | CH₂SeCH₃ | O | H | OCH₃ | CH₃ | N | |
| CO₂CH₃ | CH₂SeCH₃ | O | H | Cl | OCH₃ | CH | |
| CO₂CH₃ | CH₂N₃ | O | H | OCH₃ | CH₃ | CH | |
| CO₂CH₃ | CH₂N₃ | O | H | OCH₃ | OCH₃ | N | |
| CO₂CH₃ | CH₂N₃ | O | H | Cl | OCH₃ | CH | 136–141 |
| CO₂CH₃ | CH₂N₃ | O | H | OCH₂CH₃ | NHCH₃ | CH | |
| CO₂CH₃ | CH₂N₃ | O | H | OCH₃ | CH₃ | N | 117–118 |
| CO₂CH₃ | CH₂N₃ | O | H | CH₃ | CH₃ | CH | 174–176 |
| CO₂CH₃ | CH₂N₃ | O | H | OCH₃ | OCH₃ | CH | 159–160 |
| CO₂CH₃ | CH₂NO₂ | O | H | CH₃ | OCH₃ | N | |
| CO₂CH₃ | CH₂NO₂ | O | H | CH₃ | CH₃ | CH | |
| CO₂CH₃ | CH₂NO₂ | O | H | CH₃ | OCH₃ | CH | |
| CO₂CH₃ | CH₂NO₂ | O | H | OCH₃ | OCH₃ | N | |
| CO₂CH₃ | CH₂NO₂ | O | H | OCH₃ | OCH₃ | CH | |
| CO₂CH₃ | CH₂NO₂ | O | H | Cl | OCH₃ | CH | |
| CO₂CH₃ | CH₂NC | O | H | OCH₃ | OCH₃ | N | |
| CO₂CH₃ | CH₂NC | O | H | OCH₃ | OCH₃ | N | |
| CO₂CH₂CH₃ | CH₂CN | O | H | OCH₃ | OCH₃ | CH | 132–136 |
| CO₂CH₂CH₃ | CH₂CN | O | H | OCH₃ | CH₃ | CH | |
| CO₂CH₂CH₃ | CH₂CN | O | H | CH₃ | OCH₃ | N | |
| CO₂CH₂CH₃ | CH₂CN | O | H | OCH₃ | N(OCH₃)CH₃ | N | |
| CO₂CH₂CH₃ | CH₂SCN | O | H | CH₂CH₃ | OCH₃ | CH | |
| CO₂CH₂CH₃ | CH₂SCN | O | H | OCH₃ | OCH₃ | CH | |
| CO₂CH₂CH₃ | CH₂SCN | O | H | OCH₃ | OCH₃ | N | |
| CO₂CH₂CH₃ | CH₂SCN | O | H | CH₃ | OCH₃ | CH | |
| CO₂CH₂CH₃ | CH₂P(O)(OCH₃)₂ | O | H | OCH₃ | CH₃ | CH | |
| CO₂CH₂CH₃ | CH₂P(O)(OCH₃)₂ | O | H | OCH₃ | OCH₃ | N | |
| CO₂CH₂CH₃ | CH₂P(O)(OCH₃)₂ | O | H | CH₃ | OCH₃ | CH | |
| CO₂CH₂CH₃ | CH₂N₃ | O | H | OCH₃ | OCH₃ | CH | 160–164 |
| CO₂CH₂CH₃ | CH₂N₃ | O | H | OCH₃ | CH₃ | N | 106–109 |
| CO₂CH(CH₃)₂ | CH₂CN | O | H | OCH₃ | OCH₃ | CH | |
| CO₂CH(CH₃)₂ | CH₂CN | O | H | OCH₃ | CH₃ | CH | |
| CO₂CH₂CH=CH₂ | CH₂CN | O | H | OCH₃ | OCH₃ | N | |
| CO₂CH₂CH=CH₂ | CH₂SCN | O | H | OCH₃ | OCH₃ | CH | |
| CO₂CH₂CH=CH₂ | CH₂SCN | O | H | OCH₃ | CN | CH | |
| CO₂CH₂C≡CH | CH₂P(O)(OCH₃)₂ | O | H | OCH₃ | OCH₃ | N | |
| CO₂CH₂CH₂Cl | CH₂P(O)(OCH₃)₂ | O | H | CH₃ | OCH₃ | CH | |
| CO₂CH₂CH₂Cl | CH₂CN | O | H | OCH₃ | OCH₃ | CH | |
| CO₂CH₂CH₂F | CH₂CN | O | H | CH₃ | OCH₃ | CH | |
| CO₂CH₂CH₂F | CH₂SCN | O | H | CH₃ | CHO | CH | |
| CO₂CH₂CF₃ | CH₂SCN | O | H | CH₃ | OCH₃ | CH | |
| CO₂CH₂CH₂OCH₃ | CH₂P(O)(OCH₃)₂ | O | H | OCH₃ | OCH₃ | N | |
| CO₂CH₂CH₂OCH₃ | CH₂P(O)(OCH₃)₂ | O | H | OCH₃ | OCH₃ | CH | |
| CO₂CH₂CH₂SCH₃ | CH₂CN | O | H | OCH₃ | N₃ | CH | |
| CO₂CH₂CH₂SCH₃ | CH₂SCN | O | H | OCH₃ | CH₃ | N | |
| C(O)NHCH₃ | CH₂CN | O | H | OCH₃ | OCH₃ | CH | |
| C(O)NHCH₃ | CH₂SCN | O | H | OCH₃ | CH₃ | CH | |
| C(O)NHCH₃ | CH₂SCN | O | H | OCH₃ | OCH₃ | CH | |
| C(O)NHCH₃ | CH₂P(O)(OCH₃)₂ | O | H | OCH₃ | OCH₃ | N | |
| C(O)N(CH₃)₂ | CH₂CN | O | H | CH₂CH₃ | OCH₃ | CH | |
| C(O)N(CH₃)₂ | CH₂CN | O | H | OCH₃ | CH₃ | CH | |
| C(O)N(CH₃)₂ | CH₂CN | O | H | OCH₃ | OCH₃ | N | |
| C(O)N(CH₃)₂ | CH₂CN | O | H | OCH₃ | OCH₃ | CH | |
| C(O)(CH₃)₂ | CH₂SCN | O | H | Cl | OCH₃ | CH | |
| C(O)N(CH₃)₂ | CH₂SCN | O | H | OCH₃ | OCH₃ | N | |
| C(O)N(CH₃)₂ | CH₂SCN | O | H | CH₃ | OCH₃ | CH | |
| C(O)N(CH₃)₂ | CH₂P(O)(OCH₃)₂ | O | H | OCH₃ | OCH₃ | CH | |
| C(O)N(CH₃)₂ | CH₂P(O)(OCH₃)₂ | O | H | OCH₃ | OCH₃ | N | |
| C(O)N(CH₃)₂ | CH₂SeCH₂CH₂CH₃ | O | H | OCH₃ | OCH₃ | CH | |
| C(O)N(CH₃)₂ | CHN(CH₃)₂ | O | H | OCH₃ | CH(OCH₃)₂ | CH | |
| SO₂NHCH₃ | CH₂CN | O | H | OCH₃ | OCH₃ | N | |
| SO₂NHCH₃ | CH₂CN | O | H | OCH₃ | OCH₃ | CH | |
| SO₂NHCH₃ | CH₂CN | O | H | OCH₃ | CH₃ | CH | |
| SO₂NHCH₃ | CH₂CN | O | H | OCH₃ | OCH₃ | N | |
| SO₂NHCH₃ | CH₂SCN | O | H | OCH₃ | CH₃ | CH | |
| SO₂NHCH₃ | CH₂SCN | O | H | OCH₃ | OCH₃ | CH | |
| SO₂NHCH₃ | CH₂SCN | O | H | CH₃ | OCH₃ | N | |
| SO₂NHCH₃ | CH₂SCN | O | H | Cl | OCH₃ | CH | |

TABLE I-continued

General Formula I

| R₁ | R₂ | W | R | X | Y | Z | m.p. (°C.) |
|---|---|---|---|---|---|---|---|
| SO$_2$NHCH$_3$ | CH$_2$P(O)(OCH$_3$)$_2$ | O | H | CH$_3$ | OCH$_3$ | CH | |
| SO$_2$NHCH$_3$ | CH$_2$P(O)(OCH$_3$)$_2$ | O | H | OCH$_3$ | OCH$_3$ | N | |
| SO$_2$NHCH$_2$CH$_3$ | CH$_2$CN | O | H | OCH$_3$ | OCH$_3$ | CH | |
| SO$_2$NHCH$_2$CH$_3$ | CH$_2$CN | O | H | OCH$_3$ | CH$_3$ | CH | |
| SO$_2$NHCH$_2$CH$_3$ | CH$_2$SCN | O | H | OCH$_3$ | OCH$_3$ | N | |
| SO$_2$NHCH$_2$CH$_3$ | CH$_2$P(O)(OCH$_3$)$_2$ | O | H | CH$_3$ | OCH$_3$ | CH | |
| SO$_2$N(CH$_3$)(CH$_2$CH$_3$) | CH$_2$CN | O | H | OCH$_3$ | OCH$_3$ | CH | |
| SO$_2$NHCH$_2$CH$_2$CH$_3$ | CH$_2$CN | O | H | OCH$_3$ | CH$_3$ | CH | |
| SO$_2$N(CH$_2$CH$_3$)$_2$ | CH$_2$SCN | O | H | Cl | OCH$_3$ | CH | |
| SO$_2$N(CH$_3$)(CH(CH$_3$)$_2$) | CH$_2$SCN | O | H | OCH$_3$ | OCH$_3$ | N | |
| SO$_2$N(CH$_3$)(OCH$_3$) | CH$_2$P(O)(OCH$_3$)$_2$ | O | H | OCH$_3$ | OCH$_3$ | CH | |
| SO$_2$N(CH$_3$)(OCH$_3$) | CH$_2$P(O)(OCH$_3$)$_2$ | O | H | OCH$_3$ | CH$_3$ | CH | |
| SO$_2$N(CH$_3$)(OCH$_3$) | CH$_2$CN | O | H | OCH$_3$ | OCH$_3$ | CH | |
| SO$_2$N(CH$_3$)(OCH$_3$) | CH$_2$CN | O | H | OCH$_3$ | OCH$_3$ | N | |
| SO$_2$N(CH$_3$)$_2$ | CH$_2$CN | O | H | OCH$_3$ | OCH$_3$ | CH | |
| SO$_2$N(CH$_3$)$_2$ | CH$_2$CN | O | H | OCH$_3$ | CH$_3$ | CH | |
| SO$_2$N(CH$_3$)$_2$ | CH$_2$CN | O | H | CH$_3$ | OCH$_2$CH=CH$_2$ | CH | |
| SO$_2$N(CH$_3$)$_2$ | CH$_2$CN | O | H | OCH$_3$ | CH$_3$ | N | |
| SO$_2$N(CH$_3$)$_2$ | CH$_2$SCN | O | H | CH$_2$CH$_3$ | OCH$_3$ | CH | |
| SO$_2$N(CH$_3$)$_2$ | CH$_2$SCN | O | H | OCH$_3$ | N(CH$_3$)(CH(CH$_3$)$_2$) | CH | |
| SO$_2$N(CH$_3$)$_2$ | CH$_2$SCN | O | H | OCH$_3$ | OCH$_3$ | N | |
| SO$_2$N(CH$_3$)$_2$ | CH$_2$SCN | O | H | OCH$_3$ | OCH$_3$ | CH | |
| SO$_2$N(CH$_3$)$_2$ | CH$_2$P(O)(OCH$_3$)$_2$ | O | H | OCH$_3$ | CH$_3$ | CH | |
| SO$_2$N(CH$_3$)$_2$ | CH$_2$P(O)(OCH$_3$)$_2$ | O | H | OCH$_3$ | OCH$_3$ | N | |
| SO$_2$N(CH$_3$)$_2$ | CH$_2$P(O)(OCH$_3$)$_2$ | O | H | CH$_3$ | OCH$_2$C(CH$_3$)=CH$_2$ | CH | |
| SO$_2$N(CH$_3$)$_2$ | CH$_2$P(O)(OCH$_3$)$_2$ | O | H | OCH$_3$ | OCH$_3$ | CH | |
| SO$_2$N(CH$_3$)$_2$ | CH$_2$NO$_2$ | O | H | OCH$_3$ | CH$_2$S(CH$_2$)$_3$CH$_3$ | N | |
| SO$_2$CH$_3$ | CH$_2$CN | O | H | OCH$_3$ | OCH$_3$ | CH | |
| SO$_2$CH$_3$ | CH$_2$CN | O | H | OCH$_3$ | (CH$_2$)$_4$CH$_2$SCH$_2$CH$_3$ | CH | |
| SO$_2$CH$_3$ | CH$_2$CN | O | H | OCH$_3$ | OCH$_3$ | N | |
| SO$_2$CH$_3$ | CH$_2$CN | O | H | CH$_3$ | OCH$_3$ | CH | |
| SO$_2$CH$_3$ | CH$_2$SCN | O | H | OCH$_3$ | CH$_3$ | CH | |
| SO$_2$CH$_3$ | C(O)H | O | H | OCH$_3$ | OCH$_3$ | CH | 166–168 |
| SO$_2$CH$_3$ | CH$_2$N$_3$ | O | H | OCH$_3$ | OCH$_3$ | CH | 177–175 |
| SO$_2$CH$_3$ | CH$_2$SCN | O | H | OCH$_3$ | OCH$_3$ | N | |
| SO$_2$CH$_3$ | CH$_2$SCN | O | H | OCH$_3$ | cyclopropyl | CH | |
| SO$_2$CH$_3$ | CH$_2$SCN | O | H | OCH$_3$ | OCH$_3$ | CH | |
| SO$_2$CH$_3$ | CH$_2$P(O)(OCH$_3$)$_2$ | O | H | CH$_3$ | OCH$_3$ | N | |
| SO$_2$CH$_3$ | CH$_2$P(O)(OCH$_3$)$_2$ | O | H | OCH$_3$ | OCH$_3$ | CH | |
| SO$_2$CH$_3$ | CH$_2$P(O)(OCH$_3$)$_2$ | O | H | CH$_3$ | OCH$_3$ | CH | |
| SO$_2$CH$_2$CH$_3$ | CH$_2$CN | O | H | OCH$_3$ | OCH$_3$ | N | |
| SO$_2$CH$_2$CH$_3$ | CH$_2$CN | O | H | OCH$_3$ | OCH$_3$ | CH | |
| SO$_2$CH$_2$CH$_3$ | CH$_2$CN | O | H | OCH$_3$ | 2-methylcyclopropyl | CH | |
| SO$_2$CH$_2$CH$_3$ | CH$_2$CN | O | H | OCH$_3$ | CH$_3$ | N | |
| SO$_2$CH$_2$CH$_3$ | CH$_2$CN | O | H | CH$_3$ | OCH$_3$ | CH | |
| SO$_2$CH$_2$CH$_3$ | CH$_2$SCN | O | H | OCH$_3$ | OCH$_3$ | CH | |
| SO$_2$CH$_2$CH$_3$ | CH$_2$SCN | O | H | OCH$_3$ | CH$_3$ | CH | |
| SO$_2$CH$_2$CH$_3$ | CH$_2$SCN | O | H | CH$_3$ | C≡CH | CH | |
| SO$_2$CH$_2$CH$_3$ | CH$_2$SCN | O | H | OCH$_3$ | cyclopentyl | N | |
| SO$_2$CH$_2$CH$_3$ | CH$_2$SCN | O | H | CH$_2$CH$_3$ | OCH$_3$ | CH | |
| SO$_2$CH$_2$CH$_3$ | CH$_2$P(O)(OCH$_3$)$_2$ | O | H | OCH$_3$ | CH$_3$ | CH | |
| SO$_2$CH$_2$CH$_3$ | CH$_2$P(O)(OCH$_3$)$_2$ | O | H | OCH$_3$ | OCH$_3$ | N | |
| SO$_2$CH$_2$CH$_3$ | CH$_2$P(O)(OCH$_3$)$_2$ | O | H | OCH$_3$ | OCH$_3$ | CH | |
| SO$_2$CH$_2$CH$_2$CH$_3$ | CH$_2$CN | O | H | OCH$_3$ | OCH$_3$ | CH | 157–158 |
| SO$_2$CH$_2$CH$_2$CH$_3$ | CH$_2$CN | O | H | OCH$_3$ | CH$_3$ | CH | 151–156 |
| SO$_2$CH$_2$CH$_2$CH$_3$ | CH$_2$CN | O | H | CH$_3$ | CH$_3$ | CH | 160–162 |
| SO$_2$CH$_2$CH$_2$CH$_3$ | CH$_2$CN | O | H | Cl | OCH$_3$ | CH | 151–160 |
| SO$_2$CH$_2$CH$_2$CH$_3$ | CH$_2$CN | O | H | OCH$_3$ | OCH$_3$ | N | 157–167 |
| SO$_2$CH$_2$CH$_2$CH$_3$ | CH$_2$CN | O | H | OCH$_3$ | CH$_3$ | N | 206–208 |
| SO$_2$CH$_2$CH$_2$CH$_3$ | CH$_2$N$_3$ | O | H | OCH$_3$ | OCH$_3$ | CH | 164–168 |
| SO$_2$CH$_2$CH$_2$CH$_3$ | CH$_2$N$_3$ | O | H | OCH$_3$ | CH$_3$ | CH | 157–159 |
| SO$_2$CH$_2$CH$_2$CH$_3$ | CH$_2$N$_3$ | O | H | CH$_3$ | CH$_3$ | CH | 163–166 |
| SO$_2$CH$_2$CH$_2$CH$_3$ | CH$_2$N$_3$ | O | H | Cl | OCH$_3$ | CH | 182–184 |
| SO$_2$CH$_2$CH$_2$CH$_3$ | CH$_2$N$_3$ | O | H | OCH$_3$ | OCH$_3$ | N | 176–178 |
| SO$_2$CH$_2$CH$_2$CH$_3$ | CH$_2$N$_3$ | O | H | OCH$_3$ | CH$_3$ | N | 179–181 |
| SCH$_3$ | CH$_2$CN | O | H | OCH$_3$ | OCH$_3$ | CH | |
| SCH$_2$CH$_2$CH$_3$ | CH$_2$CN | O | H | OCH$_3$ | OCH$_3$ | N | |
| S(O)CH$_2$CH$_3$ | CH$_2$SCN | O | H | CH$_3$ | OCH$_3$ | CH | |
| S(O)CH$_2$CH$_2$CH$_3$ | CH$_2$P(O)(OCH$_3$)$_2$ | O | H | OCH$_3$ | OCH$_3$ | CH | |
| OSO$_2$CH$_3$ | CH$_2$CN | O | H | OCH$_3$ | CH$_3$ | N | |
| OSO$_2$CH$_3$ | CH$_2$CN | O | H | CH$_3$ | OCH$_3$ | CH | |
| OSO$_2$CH$_3$ | CH$_2$CN | O | H | OCH$_3$ | CHO | CH | |
| OSO$_2$CH$_3$ | CH$_2$CN | O | H | OCH$_3$ | OCH$_3$ | N | |
| OSO$_2$CH$_3$ | CH$_2$CN | O | H | OCH$_3$ | OCH$_3$ | CH | |
| OSO$_2$CH$_3$ | CH$_2$SCN | O | H | OCH$_3$ | C≡CCH$_3$ | CH | |
| OSO$_2$CH$_3$ | CH$_2$SCN | O | H | OCH$_3$ | OCH$_3$ | N | |
| OSO$_2$CH$_3$ | CH$_2$SCN | O | H | OCH$_3$ | CH$_3$ | CH | |
| OSO$_2$CH$_3$ | CH$_2$SCN | O | H | OCH$_3$ | OCH$_3$ | CH | |

TABLE I-continued

General Formula I

| R₁ | R₂ | W | R | X | Y | Z | m.p. (°C.) |
|---|---|---|---|---|---|---|---|
| OSO₂CH₃ | CH₂P(O)(OCH₃)₂ | O | H | CH₃ | OCH₃ | N | |
| OSO₂CH₃ | CH₂P(O)(OCH₃)₂ | O | H | OCH₃ | COCH₃ | CH | |
| OSO₂CH₂CH₃ | CH₂CN | O | H | CH₃ | OCH₃ | CH | |
| OSO₂CH₂CH₃ | CH₂CN | O | H | OCH₃ | OCH₃ | N | |
| OSO₂CH₂CH₃ | CH₂CN | O | H | OCH₃ | OCH₃ | CH | |
| OSO₂CH₂CH₃ | CH₂CN | O | H | OCH₃ | CH(OCH₃)₂ | CH | |
| OSO₂CH₂CH₃ | CH₂CN | O | H | OCH₃ | CH₃ | N | |
| OSO₂CH₂CH₃ | CH₂SCN | O | H | CH₃ | OCH₃ | CH | |
| OSO₂CH₂CH₃ | CH₂SCN | O | H | OCH₃ | OCH₃ | CH | |
| OSO₂CH₂CH₃ | CH₂SCN | O | H | OCH₃ | CH₃ | CH | |
| OSO₂CH₂CH₃ | CH₂P(O)(OCH₃)₂ | O | H | CH₃ | OCH₃ | CH | |
| OSO₂CH₂CH₃ | CH₂P(O)(OCH₃)₂ | O | H | OCH₃ | CH₃ | N | |
| OSO₂CH₂CH₃ | CH₂P(O)(OCH₃)₂ | O | H | CH₂CH₃ | OCH₃ | CH | |
| OSO₂CH₂CH₂CH₃ | CH₂CN | O | H | OCH₃ | CH(SCH₃)(OCH₂CH₃) | CH | |
| OSO₂CH₂CH₂CH₃ | CH₂CN | O | H | OCH₃ | OCH₃ | N | |
| OSO₂CH₂CH₂CH₃ | CH₂CN | O | H | OCH₃ | OCH₃ | CH | |
| OSO₂CH₂CH₂CH₃ | CH₂CN | O | H | OCH₃ | CH₃ | CH | |
| CH₂OCH₃ | CH₂P(O)(OCH₃)₂ | O | H | OCH₃ | OCH₃ | N | |
| CH₂SCH₃ | CH₂P(O)(OCH₃)₂ | O | H | CH₃ | C(CH₃)(SCH₃)₂ | CH | |
| CH₂CH₃OCH₃ | CH₂P(O)(OCH₃)₂ | O | H | OCH₃ | OCH₃ | CH | |
| CH₂CH₂OCH₃ | CH₂CN | O | H | OCH₃ | OCH₃ | N | |
| CH₂CH₂OCH₃ | CH₂CN | O | H | OCH₃ | OCH₃ | CH | |
| CH₂CH₂SCH₂CH₃ | CH₂CN | O | H | OCH₃ | 1,3-dioxolan-2-yl | CH | |
| CH₂CN | CH₂CN | O | H | OCH₃ | OCH₃ | N | |
| C₂H₅ | CH₂CN | O | H | OCH₃ | OCH₃ | CH | |
| C₂H₅ | CH₂CN | O | H | OCH₃ | CH₃ | CH | |
| C₂H₅ | CH₂SCN | O | H | OCH₃ | OCH₃ | N | |
| C₂H₅ | CH₂SCN | O | H | OCH₃ | 2-methyl-1,3-oxathion-2-yl | CH | |
| COCH₃ | CH₂SCN | O | H | OCH₃ | OCH₃ | CH | |
| COCH₂CH₃ | CH₂P(O)(OCH₃)₂ | O | H | CH₃ | OCH₃ | N | |
| COC≡CCH₃ | CH₂CN | O | H | OCH₃ | CH₃ | CH | |
| COCH₂CH₂Cl | CH₂CN | O | H | CH₃ | OCH₃ | CH | |
| C(O)—cyclopropyl | CH₂CN | O | H | OCH₃ | OCH₃ | N | |
| C(O)—cyclopropyl | CH₂CN | O | H | CH₃ | OCH₃ | CH | |
| C(O)—cyclopropyl | CH₂SCN | O | H | OCH₃ | CH₃ | CH | |
| CH(OCH₃)₂ | CH₂SCN | O | H | OCH₃ | OCH₃ | N | |
| CH(OCH₃)₂ | CH₂SCN | O | H | CH₃ | OCH₃ | CH | |
| CH(OCH₂CH₃)₂ | CH₂P(O)(OCH₃)₂ | O | H | OCH₃ | OCH₃ | CH | |
| CH(OCH₂CH₃)₂ | CH₂P(O)(OCH₃)₂ | O | H | OCH₃ | CH₃ | CH | |
| 1,3-dioxyl-2-yl | CH₂CN | O | H | CH₃ | OCH₃ | CH | |
| 1,3-dioxyl-2-yl | CH₂CN | O | H | OCH₃ | CH₃ | N | |
| R₁—A | CH₂CN | O | H | CH₂CH₃ | OCH₃ | CH | |
| R₁—A | CH₂CN | O | H | OCH₃ | 1,3-oxathion-2-yl | CH | |
| R₁—A | CH₂CN | O | H | OCH₃ | OCH₃ | N | |
| R₁—A | CH₂CN | O | H | OCH₃ | OCH₃ | CH | |
| R₁—A | CH₂CN | O | H | OCH₃ | CH₃ | CH | |
| R₁—A | CH₂SCN | O | H | OCH₃ | OCH₃ | N | |
| R₁—A | CH₂SCN | O | H | CH₃ | 2-methyl-1,3-dithian-2-yl | CH | |
| R₁—A | CH₂P(O)(OCH₃)₂ | O | H | OCH₃ | OCH₃ | CH | |
| R₁—A | CH₂P(O)(OCH₃)₂ | O | H | OCH₃ | OCH₃ | N | |
| R₁—A | CH₂P(O)(OCH₃)₂ | O | H | OCH₃ | OCH₃ | CH | |
| R₁—B | CH₂CN | O | H | OCH₃ | CH₃ | CH | |
| R₁—B | CH₂CN | O | H | OCH₃ | OCH₃ | N | |
| R₁—B | CH₂CN | O | H | OCH₃ | OCH₃ | CH | |
| R₁—B | CH₂CN | O | H | OCH₃ | 4-methyl-1,3-dioxolan-2-yl | CH | |
| R₁—B | CH₂SCN | O | H | OCH₃ | OCH₃ | N | |
| R₁—B | CH₂SCN | O | H | Cl | OCH₃ | CH | |
| R₁—B | CH₂SCN | O | H | OCH₃ | OCH₃ | CH | |
| R₁—B | CH₂SCN | O | H | CH₃ | OCH₃ | N | |
| R₁—B | CH₂P(O)(OCH₃)₂ | O | H | OCH₃ | OCH₃ | CH | |
| R₁—B | CH₂P(O)(OCH₃)₂ | O | H | CH₃ | OCH₃ | CH | |
| R₁—C | CH₂CN | O | H | OCH₃ | OCH₃ | N | |
| R₁—C | CH₂CN | O | H | OCH₃ | OCH₃ | CH | |
| R₁—C | CH₂CN | O | H | OCH₃ | 4-methyl-1,3-oxathiolan-2-yl | CH | |
| R₁—C | CH₂CN | O | H | OCH₃ | CH₃ | N | |
| R₁—C | CH₂SCN | O | H | CH₃ | OCH₃ | CH | |
| R₁—C | CH₂SCN | O | H | OCH₃ | OCH₃ | CH | |
| R₁—C | CH₂SCN | O | H | OCH₃ | CH₃ | CH | |
| R₁—C | CH₂P(O)(OMe)₂ | O | H | CH₃ | OCH₃ | CH | |
| R₁—C | CH₂P(O)(OMe)₂ | O | H | OCH₃ | OCH₃ | N | |
| R₁—C | CH₂P(O)(OMe)₂ | O | H | CH₂CH₃ | OCH₃ | CH | |
| R₁—D | CH₂P(O)(OMe)₂ | O | H | OCH₃ | 2,4-dimethyl-1,3- | CH | |

TABLE I-continued

General Formula I

| R₁ | R₂ | W | R | X | Y | Z | m.p. (°C.) |
|---|---|---|---|---|---|---|---|
| | | | | | dithiolan-2-yl | | |
| R₁—D | CH₂P(O)(OMe)₂ | O | H | OCH₃ | OCH₃ | N | |
| R₁—E | CH₂P(O)(OMe)₂ | O | H | OCH₃ | OCH₃ | CH | |
| R₁—F | CH₂CN | O | H | OCH₃ | OCH₃ | CH | |
| R₁—G | CH₂CN | O | H | OCH₃ | N(OCH₃)CH₃ | CH | |
| R₁—H | CH₂CN | O | H | OCH₃ | OCH₃ | N | |
| R₁—I | CH₂CN | O | H | CH₃ | CH₃ | CH | |
| R₁—J | CH₂SCN | O | H | OCH₃ | OCH₃ | CH | |
| R₁—K | CH₂SCN | O | H | OCH₃ | OCH₃ | N | |
| R₁—L | CH₂SCN | O | H | OCH₃ | OCH₃ | CH | |
| R₁—M | CH₂SCN | O | H | OCH₃ | CH₃ | CH | |
| R₁—N | CH₂CN | O | H | OCH₃ | OCH₃ | N | |
| R₁—O | CH₂CN | O | H | OCH₃ | OCH₃ | CH | |
| R₁—P | CH₂CN | O | H | Cl | OCH₃ | CH | |
| R₁—Q | CH₂CN | O | H | OCH₃ | OCH₃ | N | |
| R₁—R | CH₂P(O)(OMe)₂ | O | H | OCH₃ | OCH₃ | CH | |
| R₁—S | CH₂P(O)(OMe)₂ | O | H | OCH₃ | OCH₃ | CH | |
| CO₂CH₂CH₃ | CH₂N₃ | O | H | OCH₃ | CH₃ | CH | |
| CO₂CH₂CH₃ | CH₂N₃ | O | H | CH₃ | CH₃ | CH | 165–170 |
| CO₂CH₂CH₃ | CH₂N₃ | O | H | Cl | OCH₃ | CH | 146–148 |
| CO₂CH₂CH₃ | CH₂N₃ | O | H | OCH₃ | OCH₃ | N | |
| CO₂CH₂CH₃ | CH₂CN | O | H | Cl | OCH₃ | CH | 104–115 |
| CO₂CH(CH₃)₂ | CH₂N₃ | O | H | OCH₃ | OCH₃ | CH | 149–150 |
| CO₂CH(CH₃)₂ | CH₂N₃ | O | H | OCH₃ | CH₃ | CH | 142–144 |
| CO₂CH(CH₃)₂ | CH₂N₃ | O | H | Cl | OCH₃ | CH | 161–162 |
| CO₂CH(CH₃)₂ | CH₂N₃ | O | H | CH₃ | CH₃ | CH | 171–173 |
| GO₂CH(CH₃)₂ | CH₂N₃ | O | H | OCH₃ | OCH₃ | N | 133–134 |
| CO₂CH(CH₃)₂ | CH₂N₃ | O | H | OCH₃ | CH₃ | N | 125–127 |
| CO₂CH(CH₃)₂ | CH₂CN | O | H | OCH₃ | OCH₃ | CH | 138–140 |
| CO₂CH(CH₃)₂ | CH₂CN | O | H | Cl | OCH₃ | CH | |
| CO₂CH(CH₃)₂ | CH₂CN | O | H | OCH₃ | CH₃ | CH | |
| CO₂CH(CH₃)₂ | CH₂CN | O | H | CH₃ | CH₃ | CH | 167–169 |
| CO₂CH(CH₃)₂ | CH₂CN | O | H | OCH₃ | OCH₃ | N | |
| CO₂CH(CH₃)₂ | CH₂CN | O | H | OCH₃ | CH₃ | N | |
| Cl | CH(CH₃)CN | O | H | OCH₃ | OCH₃ | CH | |
| OCH₃ | CHFCN | O | H | OCH₃ | CH₃ | CH | |
| CO₂CH₃ | CH(CH₂CH₃)SCN | O | H | CH₃ | CH₃ | CH | |
| NO₂ | CH(CH₃)P(O)(OCH₃)₂ | O | H | OCH₃ | OCH₃ | CH | |
| SO₂N(CH₃)₂ | CH(CH₂CH₃)P(S)(CH₃)₂ | O | H | OCH₃ | OCH₃ | N | |
| CO₂N(CH₃)₂ | CH(CH₃)N(CH₃)₂ | O | H | Cl | OCH₃ | CH | |
| OCH₃ | CH(OC(O)CH₃)₂ | O | H | OCH₃ | OCH₃ | N | |
| OCH₃ | CH(CH₂CH₃)N₃ | O | H | OCH₃ | CH₃ | CH | |
| Cl | CH(CH₃)SeCH₃ | O | H | OCH₃ | OCH₃ | CH | |
| CO₂CH₂CH₃ | CH(CH₂CH₃)N₃ | O | H | OCH₃ | OCH₃ | CH | |
| OCH₂CH₃ | CH(CH₃)N₃ | O | H | OCH₃ | OCH₃ | CH | |
| OCH₂CH₃ | CH(CH₃)N₃ | O | H | OCH₃ | CH₃ | CH | |
| OCH₂CH₃ | CH(CH₃)N₃ | O | H | Cl | OCH₃ | CH | |
| OCH₂CH₃ | CH(CH₃)N₃ | O | H | OCH₃ | OCH₃ | N - | |
| OCH₂CH₃ | CH(CH₃)N₃ | O | H | OCH₃ | CH₃ | N | |
| OCH₂CH₃ | CH(CH₃)CN | O | H | OCH₃ | OCH₃ | CH | |
| OCH₂CH₃ | CH(CH₃)CN | O | H | OCH₃ | CH₃ | CH | |
| OCH₂CH₃ | CH(CH₃)CN | O | H | OCH₃ | CH₃ | N | |
| CO₂CH₃ | CH(CH₂CH₃)NC | O | H | OCH₃ | OCH₃ | CH | |
| Cl | CH(OCH₃)₂ | O | H | OCH₃ | OCH₃ | CH | |
| NO₂ | CH(OCH₃)₂ | O | H | OCH₃ | OCH₃ | CH | |
| SO₂N(CH₃)₂ | CH(OCH₃)₂ | O | H | OCH₃ | OCH₃ | CH | |
| SO₂N(CH₃)₂ | CH(OCH₃)₂ | O | H | Cl | OCH₃ | CH | |
| OCH₃ | CH(OCH₃)₂ | O | H | OCH₃ | OCH₃ | N | |
| OCH₃ | CH(OCH₃)₂ | O | H | OCH₃ | OCH₃ | CH | |
| OCH₂CH₃ | CH(OCH₃)₂ | O | H | OCH₃ | OCH₃ | N | |
| CO₂CH₃ | CH(OCH₃)₂ | O | H | OCH₃ | OCH₃ | CH | |
| CO₂CH₃ | CH(OCH₃)₂ | O | H | OCH₃ | CH₃ | CH | |
| CO₂CH₃ | CH(OCH₃)₂ | O | H | OCH₃ | CH₃ | N | |
| CO₂CH₃ | CH(OCH₂CH₃)₂ | O | H | OCH₃ | OCH₃ | CH | |
| CO₂CH₃ | C(CH₃)(OCH₃)₂ | O | H | OCH₃ | OCH₃ | CH | |
| CO₂CH₃ | C(CH₃)(OCH₃)₂ | O | H | OCH₃ | CH₃ | CH | |
| CO₂CH₃ | C(CH₃)(OCH₃)₂ | O | H | OCH₃ | OCH₃ | N | |
| CO₂CH₃ | C(CH₃)(OCH₃)₂ | O | H | CH₃ | CH₃ | CH | |
| CO₂CH₃ | C(CH₃)(OCH₃)₂ | O | H | Cl | OCH₃ | CH | |
| OCH₃ | C(CH₃)(OCH₃)₂ | O | H | OCH₃ | OCH₃ | CH | |
| OCH₂CH₃ | C(CH₃)(OCH₃)₂ | O | H | OCH₃ | OCH₃ | CH | |
| OCH₂CH₃ | C(CH₃)(OCH₃)₂ | O | H | OCH₃ | CH₃ | CH | |
| OCH₂CH₃ | C(CH₃)(OCH₃)₂ | O | H | OCH₃ | OCH₃ | N | |
| OCH₂CH₃ | C(CH₃)(OCH₃)₂ | O | H | CH₃ | CH₃ | CH | |
| CO₂CH₃ | C(CH₂CH₃)(OCH₃)₂ | O | H | OCH₃ | OCH₃ | CH | |
| CO₂CH₃ | CH(SCH₃)₃ | O | H | OCH₃ | OCH₃ | CH | |
| CO₂CH₃ | C(CH₂CH₃)(SCH₃)₂ | O | H | OCH₃ | OCH₃ | CH | |

TABLE I-continued

General Formula I

| $R_1$ | $R_2$ | W | R | X | Y | Z | m.p. (°C.) |
|---|---|---|---|---|---|---|---|
| $CO_2CH_3$ | $CH(OCCH_3)_2$ (O=) | O | H | $OCH_3$ | $OCH_3$ | CH | |
| $OCH_3$ | $CH(OCCH_3)_2$ (O=) | O | H | $OCH_3$ | $OCH_3$ | CH | |
| $CO_2CH_3$ | $CH(CN)(OSi(CH_3)_3)$ | O | H | $OCH_3$ | $OCH_3$ | CH | |
| $CO_2CH_3$ | $CH(CN)(OSi(CH_3)_3)$ | O | H | $OCH_3$ | $CH_3$ | CH | |
| $CO_2CH_3$ | $C(CH_3)(CN)OH$ | O | H | $OCH_3$ | $OCH_3$ | CH | |
| $CO_2CH_3$ | $C(CH_2CH_3)(CN)OCH_3$ | O | H | $OCH_3$ | $OCH_3$ | CH | |
| $CO_2CH_3$ | 1,-3-dithiolan-2-yl | O | H | $OCH_3$ | $OCH_3$ | N | |
| $CO_2CH_3$ | 1,-3-dithiolan-2-yl | O | H | Cl | $OCH_3$ | CH | |
| Cl | 1,-3-dithiolan-2-yl | O | H | $OCH_3$ | $OCH_3$ | CH | |
| $CO_2CH_3$ | 1,-3-dioxolan-2-yl | O | H | $OCH_3$ | $OCH_3$ | CH | |
| $CO_2CH_3$ | 1,-3-dioxolan-2-yl | O | H | $OCH_3$ | $CH_3$ | CH | |
| $NO_2$ | 1,-3-dioxolan-2-yl | O | H | $OCH_3$ | $OCH_3$ | CH | |
| $CO_2CH_3$ | 2-methyl-1,3-dioxolan-2-yl | O | H | $OCH_3$ | $OCH_3$ | CH | |
| $CO_2CH_3$ | 1,-3-dioxolan-2-yl | O | H | $OCH_3$ | $OCH_3$ | N | |
| $CO_2CH_3$ | 1,-3-dioxolan-2-yl | O | H | $OCH_3$ | $CH_3$ | CH | |
| $CO_2CH_3$ | 1,-3-dioxolan-2-yl | O | H | Cl | $OCH_3$ | CH | |
| $SO_2N(CH_3)_2$ | 1,-3-dithian-2-yl | O | H | $OCH_3$ | $OCH_3$ | CH | |
| $CO_2CH_3$ | 2-methyl-1,3-dioxan-2-yl | O | H | $OCH_3$ | $OCH_3$ | CH | |
| $C_6H_5$ | $CH_2CN$ | O | H | $OCH_3$ | $OCH_3$ | CH | |
| Cl | CH (O=) | O | H | $OCH_3$ | $OCH_3$ | CH | |
| $NO_2$ | $CCH_3$ (O=) | O | H | $OCH_3$ | $OCH_3$ | CH | |
| $SO_2N(CH_3)_2$ | $CH_3$ (O=) | O | H | $OCH_3$ | $OCH_3$ | CH | |
| $OCH_3$ | H (O=) | O | H | $OCH_3$ | $OCH_3$ | CH | |
| $OCH_3$ | CH (O=) | O | H | $OCH_3$ | $CH_3$ | CH | |
| $OCH_3$ | $CCH_3$ (O=) | O | H | $OCH_3$ | $OCH_3$ | CH | |
| $OCH_2CH_3$ | CH (O=) | O | H | $OCH_3$ | $OCH_3$ | CH | |
| $OCH_2CH_3$ | $CCH_3$ (O=) | O | H | $OCH_3$ | $OCH_3$ | CH | 192—192 |
| $OCH_2CH_3$ | $CCH_3$ (O=) | O | H | $OCH_3$ | $CH_3$ | N | 188–190 |
| $OCH_2CH_3$ | $CCH_3$ (O=) | O | H | $CH_3$ | $CH_3$ | CH | 180–181 |
| $OCH_2CH_3$ | $CCH_3$ (O=) | O | H | $OCH_3$ | $CH_3$ | CH | 137–138 |
| $OCH_2CH_3$ | $CCH_3$ (O=) | O | H | Cl | $OCH_3$ | CH | |
| $OCH_2CH_3$ | $CCH_3$ (O=) | O | H | $OCH_3$ | $OCH_3$ | N | 135–136 |

TABLE I-continued

General Formula I

| R₁ | R₂ | W | R | X | Y | Z | m.p. (°C.) |
|---|---|---|---|---|---|---|---|
| OCH₂CH₃ | O=CCH₂CH₃ | O | H | OCH₃ | OCH₃ | CH | |
| OCH₂CH₃ | O=CCH₂CH₃ | O | H | OCH₃ | OCH₃ | N | |
| OCH₂CH₃ | O=CCH₂CH₃ | O | H | Cl | OCH₃ | CH | |
| CO₂CH₃ | O=CH | O | H | OCH₃ | OCH₃ | CH | 189–190 |
| CO₂CH₃ | O=CH | O | H | OCH₃ | CH₃ | CH | 115 |
| CO₂CH₃ | O=CH | O | H | Cl | OCH₃ | CH | 182–184 |
| CO₂CH₃ | O=CH | O | H | OCH₃ | OCH₃ | N | 174–175 |
| CO₂CH₃ | O=CH | O | H | OCH₃ | CH₃ | N | 150–154 |
| CO₂CH₃ | O=CH | O | H | CH₃ | CH₃ | CH | 145–147 |
| CO₂CH₃ | O=CCH₃ | O | H | OCH₃ | OCH₃ | CH | |
| CO₂CH₃ | O=CCH₃ | O | H | OCH₃ | CH₃ | CH | |
| CO₂CH₃ | O=CCH₃ | O | H | OCH₃ | OCH₃ | N | |
| CO₂CH₃ | O=CCH₃ | O | H | OCH₃ | CH₃ | N | |
| CO₂CH₂CH₃ | O=CCH₃ | O | H | OCH₃ | OCH₃ | CH | |
| CO₂CH₂CH₃ | O=CCH₃ | O | H | OCH₃ | CH₃ | CH | |
| CO₂CH₂CH₃ | O=CH | O | H | Cl | OCH₃ | CH | 123–124 |
| OSO₂CH₃ | O=CH | O | H | OCH₃ | CH₃ | CH | |
| SO₂CH₂CH₃ | O=CH | O | H | OCH₃ | OCH₂CH₃ | CH | |
| C(O)N(CH₂CH₃)₂ | Cl | O | H | CH₃ | CH₃ | CH | 180–183 |
| Cl | CH₂N₃ | O | H | OCH₃ | OCH₃ | CH | 150–152 |
| Cl | CH₂N₃ | O | H | OCH₃ | CH₃ | CH | 138–139 |
| Cl | CH₂N₃ | O | H | CH₃ | CH₃ | CH | 167–170 |
| Cl | CH₂N₃ | O | H | Cl | OCH₃ | CH | 145–147 |
| Cl | CH₂N₃ | O | H | OCH₃ | OCH₃ | N | 134–137 |
| Cl | CH₂N₃ | O | H | OCH₃ | CH₃ | N | oil |

TABLE I-continued

General Formula I

| R₁ | R₂ | W | R | X | Y | Z | m.p. (°C.) |
|---|---|---|---|---|---|---|---|
| CO₂CH₂CH₃ | $\overset{O}{\underset{\|}{CH}}$ | O | H | OCH₃ | OCH₃ | CH | 144-146 |
| CO₂CH₂CH₃ | $\overset{O}{\underset{\|}{CH}}$ | O | H | CH₃ | CH₃ | CH | 144-146 |
| CO₂CH₂CH₃ | $\overset{O}{\underset{\|}{CH}}$ | O | H | OCH₃ | OCH₃ | N | 146-148 |
| CO₂CH₂CH₃ | $\overset{O}{\underset{\|}{CH}}$ | O | H | OCH₃ | CH₃ | N | 142-145 |
| CO₂CH₂CH₂CH₃ | CH₂N₃ | O | H | OCH₃ | OCH₃ | CH | 128 |
| CO₂CH₂CH₂CH₃ | CH₂N₃ | O | H | OCH₃ | CH₃ | CH | 131-132 |
| CO₂CH₂CH₂CH₃ | CH₂N₃ | O | H | CH₃ | CH₃ | CH | 144-147 |
| CO₂CH₂CH₂CH₃ | CH₂N₃ | O | H | Cl | OCH₃ | CH | 156-158 |
| CO₂CH₂CH₂CH₃ | CH₂N₃ | O | H | OCH₃ | OCH₃ | N | 134-135 |
| CO₂CH₂CH₂CH₃ | CH₂N₃ | O | H | OCH₃ | CH₃ | N | oil |
| CO₂CH₂CH₂CH₃ | CH₂CN | O | H | OCH₃ | OCH₃ | CH | 130-131 |
| CO₂CH₂CH₂CH₃ | CH₂CN | O | H | OCH₃ | CH₃ | CH | 144-145 |
| CO₂CH₂CH₂CH₃ | CH₂CN | O | H | CH₃ | CH₃ | CH | 150-152 |
| CO₂CH₂CH₂CH₃ | CH₂CN | O | H | Cl | OCH₃ | CH | 178-181 |
| CO₂CH₂CH₂CH₃ | CH₂CN | O | H | OCH₃ | OCH₃ | N | oil |
| CO₂CH₂CH₂CH₃ | CH₂CN | O | H | OCH₃ | CH₃ | N | oil |
| CO₂CH₃ | CH=NOCH₃ | O | H | OCH₃ | OCH₃ | CH | 171-174 |
| CO₂CH₃ | CH=NOCH₃ | O | H | OCH₃ | CH₃ | CH | 188-190 |
| CO₂CH₃ | CH=NOCH₃ | O | H | CH₃ | CH₃ | CH | 182-185 |
| CO₂CH₃ | CH=NOCH₃ | O | H | Cl | OCH₃ | CH | 185-188 |
| CO₂CH₃ | CH=NOCH₃ | O | H | OCH₃ | OCH₃ | N | 167-169 |
| CO₂CH₃ | CH=NOCH₃ | O | H | OCH₃ | CH₃ | N | 136-138 |
| OCH₂CH₃ | C(CH₃)=NOH | O | H | OCH₃ | OCH₃ | CH | 170-171 |
| OCH₂CH₃ | C(CH₃)=NOH | O | H | OCH₃ | CH₃ | CH | 183-185 |
| OCH₂CH₃ | C(CH₃)=NOH | O | H | CH₃ | CH₃ | CH | 180-182 |
| OCH₂CH₃ | C(CH₃)=NOH | O | H | Cl | OCH₃ | CH | 115-118 |
| OCH₂CH₃ | C(CH₃)=NOH | O | H | OCH₃ | OCH₃ | N | 95-100 |
| OCH₂CH₃ | C(CH₃)=NOH | O | H | OCH₃ | CH₃ | N | 112-116 |
| OCH₂CH₃ | C(CH₃)=NOCH₃ | O | H | OCH₃ | OCH₃ | CH | 185-187 |
| OCH₂CH₃ | C(CH₃)=NOCH₃ | O | H | OCH₃ | CH₃ | CH | |
| OCH₂CH₃ | C(CH₃)=NOCH₃ | O | H | OCH₃ | OCH₃ | N | |
| OCH₂CH₃ | C(CH₃)=NOCH₃ | O | H | OCH₃ | CH₃ | N | |
| F | CH=NOH | O | H | OCH₃ | OCH₃ | CH | |
| F | CH=NOCH₃ | O | H | OCH₃ | OCH₃ | CH | |
| F | C(CH₃)=NOH | O | H | OCH₃ | OCH₃ | CH | |
| F | C(CH₃)=NOCH₃ | O | H | OCH₃ | OCH₃ | CH | |
| Cl | CH=NOH | O | H | OCH₃ | OCH₃ | CH | |
| Cl | CH=NOCH₃ | O | H | OCH₃ | OCH₃ | CH | |
| Cl | C(CH₃)=NOH | O | H | OCH₃ | OCH₃ | CH | |
| Cl | C(CH₃)=NOCH₃ | O | H | OCH₃ | OCH₃ | CH | |
| NO₂ | CH=NOH | O | H | OCH₃ | OCH₃ | CH | |
| NO₂ | CH=NOCH₃ | O | H | OCH₃ | OCH₃ | CH | |
| NO₂ | C(CH₃)=NOH | O | H | OCH₃ | OCH₃ | CH | |
| NO₂ | C(CH₃)=NOCH₃ | O | H | OCH₃ | OCH₃ | CH | |
| CH₃ | CH=NOH | O | H | OCH₃ | OCH₃ | CH | |
| CH₃ | CH=NOCH₃ | O | H | OCH₃ | OCH₃ | CH | |
| CH₃ | C(CH₃)=NOH | O | H | OCH₃ | OCH₃ | CH | |
| CH₃ | C(CH₃)=NOCH₃ | O | H | OCH₃ | OCH₃ | CH | |
| C(O)N(CH₃)₂ | CH=NOH | O | H | OCH₃ | OCH₃ | CH | |
| C(O)N(CH₃)₂ | CH=NOCH₃ | O | H | OCH₃ | OCH₃ | CH | |
| C(O)N(CH₃)₂ | C(CH₃)=NOH | O | H | OCH₃ | OCH₃ | CH | |
| C(O)N(CH₃)₂ | C(CH₃)=NOCH₃ | O | H | OCH₃ | OCH₃ | CH | |
| SO₂N(CH₃)₂ | CH=NOH | O | H | OCH₃ | OCH₃ | CH | |
| SO₂N(CH₃)₂ | CH=NOCH₃ | O | H | OCH₃ | OCH₃ | CH | |
| SO₂N(CH₃)₂ | C(CH₃)=NOH | O | H | OCH₃ | OCH₃ | CH | |
| SO₂N(CH₃)₂ | C(CH₃)=NOCH₃ | O | H | OCH₃ | OCH₃ | CH | |
| SO₂CH₃ | CH=NOH | O | H | OCH₃ | OCH₃ | CH | |
| SO₂CH₃ | CH=NOCH₃ | O | H | OCH₃ | OCH₃ | CH | |
| SO₂CH₃ | C(CH₃)=NOH | O | H | OCH₃ | OCH₃ | CH | |
| SO₂CH₃ | CH(CH₃)=NOCH₃ | O | H | OCH₃ | OCH₃ | CH | |
| OSO₂CH₃ | CH=NOH | O | H | OCH₃ | OCH₃ | CH | |
| OSO₂CH₃ | CH=NOCH₃ | O | H | OCH₃ | OCH₃ | CH | |
| OSO₂CH₃ | C(CH₃)=NOH | O | H | OCH₃ | OCH₃ | CH | |
| OSO₂CH₃ | C(CH₃)=NOCH₃ | O | H | OCH₃ | OCH₃ | CH | |
| CH₂OCH₃ | CH=NOH | O | H | OCH₃ | OCH₃ | CH | |
| CH₂OCH₃ | CH=NOCH₃ | O | H | OCH₃ | OCH₃ | CH | |
| CH₂OCH₃ | C(CH₃)=NOH | O | H | OCH₃ | OCH₃ | CH | |

TABLE I-continued

General Formula I

| R₁ | R₂ | W | R | X | Y | Z | m.p. (°C.) |
|---|---|---|---|---|---|---|---|
| CH₂OCH₃ | C(CH₃)=NOCH₃ | O | H | OCH₃ | OCH₃ | CH | |
| CH₂SCH₃ | CH=NOH | O | H | OCH₃ | OCH₃ | CH | |
| CH₂SCH₃ | CH=NOCH₃ | O | H | OCH₃ | OCH₃ | CH | |
| CH₂SCH₃ | C(CH₃)=NOH | O | H | OCH₃ | OCH₃ | CH | |
| CH₂SCH₃ | C(CH₃)=NOCH₃ | O | H | OCH₃ | OCH₃ | CH | |
| CH₂CN | CH=NOH | O | H | OCH₃ | OCH₃ | CH | |
| CH₂CN | CH=NOCH₃ | O | H | OCH₃ | OCH₃ | CH | |
| CH₂CN | C(CH₃)=NOH | O | H | OCH₃ | OCH₃ | CH | |
| CH₂CN | C(CH₃)=NOCH₃ | O | H | OCH₃ | OCH₃ | CH | |
| CH(OCH₃)₂ | CH=NOH | O | H | OCH₃ | OCH₃ | CH | |
| CH(OCH₃)₂ | CH=NOCH₃ | O | H | OCH₃ | OCH₃ | CH | |
| CH(OCH₃)₂ | C(CH₃)=NOH | O | H | OCH₃ | OCH₃ | CH | |
| CH(OCH₃)₂ | C(CH₃)=NOCH₃ | O | H | OCH₃ | OCH₃ | CH | |
| R₁—A | CH=NOH | O | H | OCH₃ | OCH₃ | CH | |
| R₁—B | CH=NOH | O | H | OCH₃ | OCH₃ | CH | |
| R₁—C | CH=NOH | O | H | OCH₃ | OCH₃ | CH | |
| R₁—D | CH=NOH | O | H | OCH₃ | OCH₃ | CH | |
| R₁—E | CH=NOH | O | H | OCH₃ | OCH₃ | CH | |
| R₁—F | CH=NOH | O | H | OCH₃ | OCH₃ | CH | |
| R₁—G | CH=NOH | O | H | OCH₃ | OCH₃ | CH | |
| R₁—H | CH=NOH | O | H | OCH₃ | OCH₃ | CH | |
| R₁—I | CH=NOH | O | H | OCH₃ | OCH₃ | CH | |
| R₁—J | CH=NOH | O | H | OCH₃ | OCH₃ | CH | |
| R₁—K | CH=NOH | O | H | OCH₃ | OCH₃ | CH | |
| R₁—L | CH=NOH | O | H | OCH₃ | OCH₃ | CH | |
| R₁—M | CH=NOH | O | H | OCH₃ | OCH₃ | CH | |
| R₁—N | CH=NOH | O | H | OCH₃ | OCH₃ | CH | |
| R₁—O | CH=NOH | O | H | OCH₃ | OCH₃ | CH | |
| R₁—P | CH=NOH | O | H | OCH₃ | OCH₃ | CH | |
| R₁—Q | CH=NOH | O | H | OCH₃ | OCH₃ | CH | |
| R₁—R | CH=NOH | O | H | OCH₃ | OCH₃ | CH | |
| R₁—S | CH=NOH | O | H | OCH₃ | OCH₃ | CH | |

TABLE II

General Formula II

| R₁ | R₂ | X₁ | Y₁ | m.p. (°C.) |
|---|---|---|---|---|
| F | CH₂CN | CH₃ | O | |
| Cl₃ | CH₂SCN | OCH₃ | O | |
| CF₃ | CH₂P(O)(OCH₂CH₃)₂ | OCH₃ | CH₂ | |
| NO₂ | CH₂CN | OCH₃ | O | |
| OCH₃ | CH₂CN | OCH₃ | O | |
| OCH₃ | CH₂SCN | OCH₃ | CH₂ | |
| OCH₂CH₃ | CH₂SCN | OCH₃ | O | |
| OCH₂CH₃ | CH₂CN | OCH₃ | CH₂ | |
| CO₂CH₃ | CH₂CN | OCF₂H | O | |
| CO₂CH₃ | CH₂CN | OCH₃ | CH₂ | |
| CO₂CH₃ | CH₂SCN | OCH₃ | O | |
| CO₂CH₃ | CH₂P(O)(OCH₃)₂ | OCH₃ | O | |
| CO₂CH₂CH₃ | CH₂P(O)(OCH₃)₂ | OCH₃ | O | |
| CO₂CH₂CH₃ | CH₂CN | OCH₃ | CH₃ | |
| CO₂N(CH₃)₂ | CH₂CN | CH₃ | O | |
| SO₂NHCH₃ | CH₂CN | OCH₃ | O | |
| SO₂N(CH₃)₂ | CH₂CN | OCH₃ | CH₂ | |
| SO₂N(CH₃)₂ | CH₂SCN | OCH₃ | O | |
| SO₂CH₃ | CH₂SCN | OCH₃ | O | |
| SO₂CH₃ | CH₂CN | OCF₂H | CH₂ | |
| SO₂CH₂CH₃ | CH₂CN | OCH₃ | O | |
| SO₂CH₂CH₃ | CH₂P(O)(OCH₃)₂ | OCH₃ | O | |
| OSO₂CH₃ | CH₂P(O)(OCH₃)₂ | OCH₃ | CH₂ | |
| OSO₂CH₃ | CH₂CN | OCH₂CH₃ | O | |
| OSO₂CH₂CH₃ | CH₂SCN | OCH₃ | O | |
| R₁—A | CH₂CN | CH₃ | O | |
| R₁—A | CH₂SCN | OCH₃ | CH₂ | |
| R₁—B | CH₂P(O)(OCH₃)₂ | OCH₃ | O | |
| R₁—C | CH₂CN | OCH₃ | O | |
| F | CH=NOH | CH₃ | O | |
| OCH₃ | CH=NOH₃ | OCH₃ | O | |
| COOCH₃ | C(CH₃)=NOH | OCF₂H | CH₂ | |
| CO₂N(CH₃)₂ | C(CH₃)=NOCH₃ | CH₃ | O | |
| SO₂N(CH₃)₂ | CH=NOH | OCH₃ | O | |
| SO₂CH₃ | CH=NOCH₃ | OCH₃ | CH₂ | |
| OSO₂CH₂CH₃ | C(CH₃)=NOH | OCF₂H | O | |
| R₁—A | C(CH₃)=NOCH₃ | CH₃ | O | |
| R₁—B | CH=NOH | CH₃ | CH₂ | |

TABLE II-continued

General Formula II

| R₁ | R₂ | X₁ | Y₁ | m.p. (°C.) |
|---|---|---|---|---|
| R₁—C | CH=NOCH₃ | OCH₃ | O | |

TABLE III

General Formula III

| R₁ | R₂ | X₁ | m.p. (°C.) |
|---|---|---|---|
| F | CH₂CN | CH₃ | |
| Cl | CH₂SCN | OCH₃ | |
| CF₃ | CH₂P(O)(OCH₂CH₃)₂ | OCH₃ | |
| NO₂ | CH₂CN | OCH₃ | |
| OCH₃ | CH₂CN | OCH₃ | |
| OCH₃ | CH₂SCN | OCH₃ | |
| OCH₂CH₃ | CH₂SCN | OCH₃ | |
| OCH₂CH₃ | CH₂CN | OCH₃ | |
| CO₂CH₃ | CH₂CN | OCF₂H | |
| CO₂CH₃ | CH₂CN | OCH₃ | |
| CO₂CH₃ | CH₂SCN | OCH₃ | |
| CO₂CH₃ | CH₂P(O)(OCH₃)₂ | OCH₃ | |
| CO₂CH₂CH₃ | CH₂P(O)(OCH₃)₂ | OCH₃ | |
| CO₂CH₂CH₃ | CH₂CN | OCH₃ | |
| CO₂N(CH₃)₂ | CH₂CN | CH₃ | |
| SO₂NHCH₃ | CH₂CN | OCH₃ | |
| SO₂N(CH₃)₂ | CH₂CN | OCH₃ | |
| SO₂N(CH₃)₂ | CH₂SCN | OCH₃ | |
| SO₂CH₃ | CH₂SCN | OCH₃ | |
| SO₂CH₃ | CH₂CN | OCF₂H | |
| SO₂CH₂CH₃ | CH₂CN | OCH₃ | |
| SO₂CH₂CH₃ | CH₂P(O)(OCH₃)₂ | OCH₃ | |
| OSO₂CH₃ | CH₂P(O)(OCH₃)₂ | OCH₃ | |
| OSO₂CH₃ | CH₂CN | OCH₂CH₃ | |
| OSO₂CH₂CH₃ | CH₂SCN | OCH₃ | |
| R₁—A | CH₂CN | CH₃ | |
| R₁—A | CH₂SCN | OCH₃ | |
| R₁—B | CH₂P(O)(OCH₃)₂ | OCH₃ | |
| R₁—C | CH₂CN | OCH₃ | |
| F | CH=NOH | CH₃ | |
| OCH₃ | CH=NOCH₃ | OCH₃ | |

TABLE III-continued

General Formula III

| R₁ | R₂ | X₁ | m.p. (°C.) |
|---|---|---|---|
| COOCH₃ | C(CH₃)=NOH | OCH₃ | |
| CO₂N(CH₃)₂ | C(CH₃)=NOCH₃ | OCF₂H | |
| SO₂N(CH₃)₂ | CH=NOH | CH₃ | |
| SO₂CH₃ | CH=NOCH₃ | OCH₃ | |
| OSO₂CH₂CH₃ | C(CH₃)=NOH | CH₃ | |
| R₁—A | C(CH₃)=NOCH₃ | OCH₃ | |
| R₁—B | CH=NOH | OCF₂H | |
| R₁—C | CH=NOCH₃ | OCH₃ | |

TABLE IV

General Formula IV

| R₁ | R₂ | X₁ | Y₃ | m.p. (°C.) |
|---|---|---|---|---|
| F | CH₂CN | CH₃ | H | |
| Cl | CH₂SCN | OCH₃ | H | |
| CF₃ | CH₂P(O)(OCH₂CH₃)₂ | OCH₃ | CH₃ | |
| NO₂ | CH₂CN | OCH₃ | H | |
| OCH₃ | CH₂CN | OCH₃ | H | |
| OCH₃ | CH₂SCN | OCH₃ | CH₃ | |
| OCH₂CH₃ | CH₂SCN | OCH₃ | H | |
| OCH₂CH₃ | CH₂CN | OCH₃ | CH₃ | |
| CO₂CH₃ | CH₂CN | OCF₂H | H | |
| CO₂CH₃ | CH₂CN | OCH₃ | CH₃ | |
| CO₂CH₃ | CH₂SCN | OCH₃ | H | |
| CO₂CH₃ | CH₂P(O)(OCH₃)₂ | OCH₃ | H | |
| CO₂CH₂CH₃ | CH₂P(O)(OCH₃)₂ | OCH₃ | H | |
| CO₂CH₂CH₃ | CH₂CN | OCH₃ | CH₃ | |
| CO₂N(CH₃)₂ | CH₂CN | CH₃ | H | |
| SO₂NHCH₃ | CH₂CN | OCH₃ | H | |
| SO N(CH₃)₂ | CH₂CN | OCH₃ | H | |
| SO₂N(CH₃)₂ | CH₂SCN | OCH₃ | H | |

TABLE IV-continued

General Formula IV

| R₁ | R₂ | X₁ | Y₃ | m.p. (°C.) |
|---|---|---|---|---|
| SO₂CH₃ | CH₂SCN | OCH₃ | H |  |
| SO₂CH₃ | CH₂CN | OCF₂H | CH₃ |  |
| SO₂CH₂CH₃ | CH₂CN | OCH₃ | H |  |
| SO₂CH₂CH₃ | CH₂P(O)(OCH₃)₂ | OCH₃ | H |  |
| OSO₂CH₃ | CH₂P(O)(OCH₃)₂ | OCH₃ | CH₃ |  |
| OSO₂CH₃ | CH₂CN | OCH₂CH₃ | H |  |
| OSO₂CH₂CH₃ | CH₂SCN | OCH₃ | H |  |
| R₁—A | CH₂CN | CH₃ | H |  |
| R₁—A | CH₂SCN | OCH₃ | CH₃ |  |
| R₁—B | CH₂P(O)(OCH₃)₂ | OCH₃ | H |  |
| R₁—C | CH₂CN | OCH₃ | H |  |
| F | CH=NOH | CH₃ | H |  |
| OCH₃ | CH=NOH₃ | CH₃ | CH₃ |  |
| COOCH₃ | C(CH₃)=NOH | OCH₃ | H |  |
| CO₂N(CH₃)₂ | C(CH₃)=NOCH₃ | OCH₃ | H |  |
| SO₂N(CH₃)₂ | CH=NOH | OCH₃ | H |  |
| SO₂CH₃ | CH=NOCH₃ | CH₃ | CH₃ |  |
| OSO₂CH₂CH₃ | C(CH₃)=NOH | CH₃ | H |  |
| R₁—A | C(CH₃)NOCH₃ | OCH₃ | H |  |
| R₁—B | CH=NOH | CH₃ | CH₃ |  |
| R₁—C | CH=NOCH₃ | OCH₃ | H |  |

TABLE V

General Formula V

| R₁ | R₂ | X₂ | Y₂ | m.p. (°C.) |
|---|---|---|---|---|
| F | CH₂CN | CH₃ | OCH₃ |  |
| Cl | CH₂SCN | CH₃ | OCH₂CH₃ |  |
| CF₃ | CH₂P(O)(OCH₂CH₃)₂ | CH₃ | OCH₃ |  |
| NO₂ | CH₂CN | CH₃ | SCH₃ |  |
| OCH₃ | CH₂CN | CH₂CH₃ | OCH₃ |  |
| OCH₃ | CH₂SCN | CH₃ | SCH₂CH₃ |  |
| OCH₂CH₃ | CH₂SCN | CH₃ | OCH₃ |  |
| OCH₂CH₃ | CH₂CN | CH₂CF₃ | OCH₃ |  |
| CO₂CH₃ | CH₂CN | CH₃ | CH₃ |  |
| CO₂CH₃ | CH₂CN | CH₃ | OCH₃ |  |
| CO₂CH₃ | CH₂SCN | CH₃ | CH₂CH₃ |  |
| CO₂CH₃ | CH₂P(O)(OCH₃)₂ | CH₂CH₃ | OCH₃ |  |
| CO₂CH₂CH₃ | CH₂P(O)(OCH₃)₂ | CH₃ | OCH₃ |  |
| CO₂CH₂CH₃ | CH₂CN | CH₃ | OCH₂CH₃ |  |
| CO₂N(CH₃)₂ | CH₂CN | CH₂CF₃ | OCH₃ |  |
| SO₂NHCH₃ | CH₂CN | CH₃ | OCH₃ |  |
| SO₂N(CH₃)₂ | CH₂CN | CH₃ | SCH₃ |  |
| SO₂N(CH₃)₂ | CH₂SCN | CH₂CH₃ | OCH₃ |  |
| SO₂CH₃ | CH₂SCN | CH₃ | OCH₃ |  |
| SO₂CH₃ | CH₂CN | CH₃ | SCH₂CH₃ |  |
| SO₂CH₂CH₃ | CH₂CN | CH₃ | OCH₃ |  |
| SO₂CH₂CH₃ | CH₂P(O)(OCH₃)₂ | CH₂CF₃ | OCH₃ |  |
| OSO₂CH₃ | CH₂P(O)(OCH₃)₂ | CH₃ | CH₃ |  |
| OSO₂CH₃ | CH₂CN | CH₃ | OCH₃ |  |
| OSO₂CH₂CH₃ | CH₂SCN | CH₂CH₃ | OCH₃ |  |
| R₁—A | CH₂CN | CH₃ | OCH₃ |  |
| R₁—A | CH₂SCN | CH₃ | CH₂CH₃ |  |
| R₁—B | CH₂P(O)(OCH₃)₂ | CH₃ | OCH₃ |  |
| R₁—C | CH₂CN | CH₃ | OCH₃ |  |
| F | CH=NOH | CH₃ | OCH₃ |  |
| OCH₃ | CH=NOHCH₃ | CH₃ | CH₃ |  |
| COOCH₃ | C(CH₃)=NOH | CH₂CH₃ | OCH₃ |  |
| CO₂N(CH₃)₂ | C(CH₃)=NOCH₃ | CH₂CF₃ | CH₃ |  |
| SO₂N(CH₃)₂ | CH=NOH | CH₃ | OCH₂CH₃ |  |
| SO₂CH₃ | CH=NOCH₃ | CH₃ | OCH₃ |  |
| OSO₂CH₂CH₃ | C(CH₃)=NOH | CH₂CF₃ | OCH₃ |  |
| R₁—A | C(CH₃)=NOCH₃ | CH₂CH₃ | CH₃ |  |
| R₁—B | CH=NOH | CH₃ | OCH₃ |  |
| R₁—C | CH=NOCH₃ | CH₃ | CH₃ |  |

TABLE VI

General Formula VI

| R₁ | R₂ | X₃ | m.p. (°C.) |
|---|---|---|---|
| F | CH₂CN | OCH₃ |  |
| Cl | CH₂SCN | OCH₃ |  |
| CF₃ | CH₂P(O)(OCH₂CH₃)₂ | OCH₃ |  |
| NO₂ | CH₂CN | CH₃ |  |
| OCH₃ | CH₂CN | OCH₃ |  |

TABLE VI-continued

General Formula VI

| $R_1$ | $R_2$ | $X_3$ | m.p. (°C.) |
|---|---|---|---|
| $OCH_3$ | $CH_2SCN$ | $CH_3$ | |
| $OCH_2CH_3$ | $CH_2SCN$ | $OCH_3$ | |
| $OCH_2CH_3$ | $CH_2CN$ | $CH_3$ | |
| $CO_2CH_3$ | $CH_2CN$ | $OCH_3$ | |
| $CO_2CH_3$ | $CH_2CN$ | $CH_3$ | |
| $CO_2CH_3$ | $CH_2SCN$ | $OCH_3$ | |
| $CO_2CH_3$ | $CH_2P(O)(OCH_3)_2$ | $CH_3$ | |
| $CO_2CH_2CH_3$ | $CH_2P(O)(OCH_3)_2$ | $OCH_3$ | |
| $CO_2CH_2CH_3$ | $CH_2CN$ | $CH_3$ | |
| $CO_2N(CH_3)_2$ | $CH_2CN$ | $OCH_3$ | |
| $SO_2NHCH_3$ | $CH_2CN$ | $CH_3$ | |
| $SO_2N(CH_3)_2$ | $CH_2CN$ | $OCH_3$ | |
| $SO_2N(CH_3)_2$ | $CH_2SCN$ | $CH_3$ | |
| $SO_2CH_3$ | $CH_2SCN$ | $OCH_3$ | |
| $SO_2CH_3$ | $CH_2CN$ | $OCH_3$ | |
| $SO_2CH_2CH_3$ | $CH_2CN$ | $CH_3$ | |
| $SO_2CH_2CH_3$ | $CH_2P(O)(OCH_3)_2$ | $OCH_3$ | |
| $OSO_2CH_3$ | $CH_2P(O)(OCH_3)_2$ | $CH_3$ | |
| $OSO_2CH_3$ | $CH_2CN$ | $OCH_3$ | |
| $OSO_2CH_2CH_3$ | $CH_2SCN$ | $OCH_3$ | |
| $R_1$—A | $CH_2CN$ | $CH_3$ | |
| $R_1$—A | $CH_2SCN$ | $OCH_3$ | |
| $R_1$—B | $CH_2P(O)(OCH_3)_2$ | $CH_3$ | |
| $R_1$—C | $CH_2CN$ | $OCH_3$ | |
| F | $CH=NOH$ | $OCH_3$ | |
| $OCH_3$ | $CH=NOCH_3$ | $OCH_3$ | |
| $COOCH_3$ | $C(CH_3)=NOH$ | $CH_3$ | |
| $CO_2N(CH_3)_2$ | $C(CH_3)=NOCH_3$ | $CH_3$ | |
| $SO_2CH_3$ | $CH=NOH$ | $OCH_3$ | |
| $OSO_2CH_2CH_3$ | $C(CH_3)=NOCH_3$ | $OCH_3$ | |
| $R_1$—A | $C(CH_3)=NOH$ | $OCH_3$ | |
| $R_1$—B | $C(CH_3)=NOCH_3$ | $CH_3$ | |
| $R_1$—C | $CH=NOH$ | $OCH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength | 90–99 | 0–10 | 0–2 |

TABLE VII

General Formula VII

| $R_1$ | $R_2$ | $X_4$ | $Y_4$ | m.p. (°C.) |
|---|---|---|---|---|
| F | $CH_2CN$ | $CH_3$ | $OCH_3$ | |
| Cl | $CH_2SCN$ | $OCH_3$ | $CH_3$ | |
| $CF_3$ | $CH_2P(O)(OCH_2CH_3)_2$ | $OCH_2CH_3$ | $OCH_3$ | |
| $NO_2$ | $CH_2CN$ | $CH_2OCH_3$ | $OCH_3$ | |
| $OCH_3$ | $CH_2CN$ | Cl | $OCH_3$ | |
| $OCH_3$ | $CH_2SCN$ | $CH_3$ | $OCH_2CH_3$ | |
| $OCH_2CH_3$ | $CH_2SCN$ | $OCH_3$ | $OCH_3$ | |
| $OCH_2CH_3$ | $CH_2CN$ | $OCH_3$ | Cl | |
| $CO_2CH_3$ | $CH_2CN$ | $CH_3$ | $OCH_3$ | |
| $CO_2CH_3$ | $CH_2CN$ | $OCH_3$ | $OCH_3$ | |
| $CO_2CH_3$ | $CH_2SCN$ | $OCH_3$ | $CH_3$ | |
| $CO_2CH_3$ | $CH_2P(O)(OCH_3)_2$ | $OCH_2CH_3$ | $OCH_3$ | |
| $CO_2CH_2CH_3$ | $CH_2P(O)(OCH_3)_2$ | $OCH_3$ | $OCH_3$ | |
| $CO_2CH_2CH_3$ | $CH_2CN$ | $OCH_3$ | $OCH_2CH_3$ | |
| $CO_2N(CH_3)_2$ | $CH_2CN$ | $CH_2OCH_3$ | $OCH_3$ | |
| $SO_2NHCH_3$ | $CH_2CN$ | $OCH_3$ | $CH_3$ | |
| $SO_2N(CH_3)_2$ | $CH_2CN$ | $OCH_3$ | $OCH_3$ | |
| $SO_2N(CH_3)_2$ | $CH_2SCN$ | Cl | $OCH_3$ | |
| $SO_2CH_3$ | $CH_2SCN$ | $OCH_3$ | $CH_3$ | |
| $SO_2CH_3$ | $CH_2CN$ | $OCH_3$ | $OCH_3$ | |
| $SO_2CH_2CH_3$ | $CH_2CN$ | $OCH_3$ | $OCH_3$ | |
| $SO_2CH_2CH_3$ | $CH_2P(O)(OCH_3)_2$ | $CH_3$ | $OCH_3$ | |
| $OSO_2CH_3$ | $CH_2P(O)(OCH_3)_2$ | $OCH_3$ | $OCH_2CH_3$ | |
| $OSO_2CH_3$ | $CH_2CN$ | $OCH_3$ | $OCH_3$ | |
| $OSO_2CH_2CH_3$ | $CH_2SCN$ | $OCH_2CH_3$ | $OCH_3$ | |
| $R_1$—A | $CH_2CN$ | $OCH_3$ | $OCH_3$ | |
| $R_1$—A | $CH_2SCN$ | $OCH_3$ | $CH_3$ | |
| $R_1$—B | $CH_2P(O)(OCH_3)_2$ | $CH_2OCH_3$ | $OCH_3$ | |
| $R_1$—C | $CH_2CN$ | $OCH_3$ | $OCH_3$ | |
| F | $CH=NOH$ | $CH_3$ | $OCH_3$ | |
| $OCH_3$ | $CH=NOCH_3$ | $OCH_3$ | $CH_3$ | |
| $COOCH_3$ | $C(CH_3)=NOH$ | $OCH_2CH_3$ | $OCH_3$ | |
| $CO_2N(CH_3)_2$ | $C(CH_3)=NOCH_3$ | $CH_2OCH_3$ | $OCH_3$ | |
| $SO_2CH_3$ | $CH=NOH_3$ | Cl | $OCH_3$ | |
| $OSO_2CH_2CH_3$ | $C(CH_3)=NOCH_3$ | $CH_3$ | $OCH_2CH_3$ | |
| $R_1$—A | $C(CH_3)=NOH$ | $OCH_3$ | $OCH_3$ | |
| $R_1$—B | $CH(CH_3)=NOCH_3$ | $OCH_3$ | Cl | |
| $R_1$—C | $CH=NOH$ | $CH_3$ | $OCH_3$ | |

| | Active | Weight Percent* | |
|---|---|---|---|
| Compositons | Ingredient | Diluent(s) | Surfactant(s) |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are somtimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1963, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York. 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 10

High Strength Concentrate 5-(cyanomethyl)-2-methoxy-N-[(4-methoxy-6-methyl-1,3,5-triazin-2-yl)aminocarbonyl]benzenesulfonamide: 99%
trimethylnonyl polyethylene glycol ether: 1%

The surfactant is sprayed upon the active ingredient in a blender and the mixture sifted through a U.S. S. No. 40 sieve (0.42 mm openings) prior to packaging. The concentrate may be formulated further for practical use.

EXAMPLE 11

Wettable Powder 5-(cyanomethyl)-N-[(4,6-dimethoxypyrimidin-2-yl)aminocarbonyl]-2-methoxybenzenesulfonamide: 65%
dodecylphenol polyethylene glycol ether: 2%
sodium ligninsulfonate: 4%
sodium silicoaluminate: 6%
montmorillonite (calcined): 23%

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 12

Aqueous Suspension 5-(cyanomethyl)-2-methoxy-N-[(4-methoxy-6-methyl-1,3,5-triazin-2-yl)aminocarbonyl]benzenesulfonamide: 50.0%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 13

Oil Suspension 5-(cyanomethyl)-2-methoxy-N-[(4-methoxy-6-methyl-1,3,5-triazin-2-yl)aminocarbonyl]benzenesulfonamide: 35%
blend of polyalcohol carboxylic esters and oil soluble petroleum sulfonates: 6%
xylene: 59%

The ingredients are combined and ground together in a sand mill to produce particles essentially all below 3 microns. The product can be used directly, extended with oils, or emulsified in water.

EXAMPLE 14

Oil Suspension 5-(cyanomethyl)-N-[(4,6-dimethoxypyrimidin-2-yl)aminocarbonyl]-2-methoxybenzenesulfonamide: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 15

Aqueous Suspension 5-(cyanomethyl)-N-[(4,6-dimethoxypyrimidin-2-yl)-aminocarbonyl]-2-methoxybenzenesulfonamide: 25%
hydrated attapulgite: 3%
crude calcium ligninsulfonate: 10%
sodium dihydrogen phosphate: 0.5%
water: 61.5%

The ingredients are ground together in a ball or roller mill until the solid particles have been reduced to diameters under 10 microns.

EXAMPLE 16

Wettable Powder 5-(cyanomethyl)-2-methoxy-N-[(4-methoxy-6-methyl-1,3,5-triazin-2-yl)aminocarbonyl]benzenesulfonamide: 40%
dioctyl sodium sulfosuccinate: 1.5%
sodium ligninsulfonate: 3%
low viscosity methyl cellulose: 1.5%
attapulgite: 54%

The ingredients are thoroughly blende, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 17

Granule wettable powder of Example 16: 15%
gypsum: 69%
potassium sulfate: 16%

The ingredients are blended in a rotating mixer and water sprayed on to accomplish granulation. When most of the material has reached the desired range of 1.0 to 0.42 cm (U.S.S. #18 to 40 sieves), the granules are removed, dried, and screened. Oversized material is crushed to produce additional material in the desired range. These granules contain % active ingredient.

EXAMPLE 18

Wettable Powder 5-(cyanomethyl)-N-[(4,6-diemthoxypyrimidin-2-yl)-aminocarbonyl]-2-methoxybenzenesulfonamide: 50%
sodium alkylnaphthalenesulfonate: 2%
low viscosity methyl cellulose: 2%
diatomaceous earth: 46%

The ingredients are blended, coarsely hammer-milled and the air milled to produce particles of active essentially all below 10 microns in diameter. The product is reblended before packaging.

EXAMPLE 19

Extruded Pellet 5-(cyanomethyl)-N-[(4,6-dimethoxypyrimidin-2-yl)aminocarbonyl]-2-methoxybenzenesulfonamide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 20

Wettable Powder 5-(cyanomethyl)-2-methoxy-N-[(4-methoxy-6-methyl-1,3,5-triazin-2-yl)aminocarbonyl]benzenesulfonamide: 80%
sodium alkylnaphthalenesulfonate: 2%
sodium ligninsulfonate: 2%
synthetic amorphous silica: 3%
kaolinite: 13%

The ingredients are blended and then ground in a hammermill to produce particles with an average particle size less than 25 microns in diameter. The material is reblended and sifted through a U.S.S. No. 50 sieve (0.3 mm opening) before being packaged.

EXAMPLE 21

High Strength Concentrate 5-(cyanomethyl)-N-[(4,6-dimethoxypyrimidin-2-yl)-aminocarbonyl]-2-methoxybenzenesulfonamide: 98.5%
silica aerogel: 0.5%
synthetic amorphous fine silica: 1.0%

The ingredients are blended and ground in a hammer mill to produce a high strength concentrate essentially all passing a U.S.S. No. 50 sieve (0.3 mm openings). This material may then be formulated in a variety of ways.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage pre-sent, etc. In general terms, the subject compounds should be applied at levels of around 0.001 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria spp.), barnyardgrass (Echinochloa crusgalli), cheatgrass (Bromus Secalinus), giant foxtail (Setaria faberii), wild oats (Avena fatua), velvetleaf (Abutilon theophrasti), morningglory (Ipomoea spp., cocklebur (Xanthium pensylvanicum), sorghum, corn, barley, soybean, sugarbeet, cotton, rice, wheat and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

B=burn;
C=chlorosis/necrosis;
D=defoliation;
E=emergence inhibition;
G=growth retardation;
H=formative effect;
U=unusual pigmentation;
X=axillary stimulation;
S=albinism; and
6Y=abscised buds or flowers.

COMPOUNDS

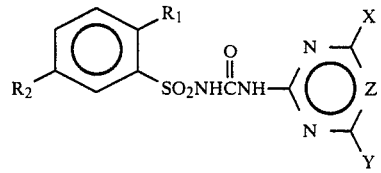

| Compound | $R_1$ | $R_2$ | X | Y | Z |
|---|---|---|---|---|---|
| 1 | $OCH_3$ | $CH_2CN$ | $CH_3$ | $OCH_3$ | CH |
| 2 | $OCH_3$ | $CH_2CN$ | $OCH_3$ | $CH_3$ | N |
| 3 | $CO_2CH_3$ | $CH_2P(O)(OCH_3)_2$ | $OCH_3$ | $OCH_3$ | CH |
| 4 | $CO_2CH_3$ | $CH_2P(O)(OCH_3)_2$ | $CH_3$ | $CH_3$ | CH |
| 5 | $CO_2CH_3$ | $CH_2P(O)(OCH_3)_2$ | $OCH_3$ | $OCH_3$ | N |
| 6 | $CO_2CH_3$ | $CH_2P(O)(OCH_3)_2$ | $OCH_3$ | $CH_3$ | N |
| 7 | $CO_2CH_3$ | $CH_2SCN$ | $OCH_3$ | $OCH_3$ | CH |
| 8 | $CO_2CH_3$ | $CH_2CN$ | $OCH_3$ | $OCH_3$ | CH |
| 9 | $CO_2CH_3$ | $CH_2CN$ | $OCH_3$ | $CH_3$ | N |
| 10 | $OCH_3$ | $CH_2N_3$ | $OCH_3$ | $OCH_3$ | CH |
| 11 | $OCH_3$ | $CH_2N_3$ | $OCH_3$ | $CH_3$ | CH |
| 12 | $OCH_3$ | $CH_2N_3$ | $CH_3$ | $CH_3$ | CH |
| 13 | $OCH_3$ | $CH_2N_3$ | $OCH_3$ | Cl | CH |
| 14 | $OCH_3$ | $CH_2N_3$ | $OCH_3$ | $OCH_3$ | N |
| 15 | $OCH_3$ | $CH_2N_3$ | $OCH_3$ | $CH_3$ | N |
| 16 | $OC_2H_5$ | $C(O)CH_3$ | $OCH_3$ | $OCH_3$ | CH |
| 17 | $OC_2H_5$ | $C(O)CH_3$ | $OCH_3$ | $CH_3$ | CH |
| 18 | $OC_2H_5$ | $C(O)CH_3$ | $CH_3$ | $CH_3$ | CH |
| 19 | $OC_2H_5$ | $C(O)CH_3$ | $OCH_3$ | $OCH_3$ | N |
| 20 | $OC_2H_5$ | $C(O)CH_3$ | $OCH_3$ | $CH_3$ | N |
| 21 | $COOCH(CH_3)_2$ | $CH_2N_3$ | $OCH_3$ | $OCH_3$ | CH |
| 22 | $COOCH(CH_3)_2$ | $CH_2N_3$ | $OCH_3$ | $CH_3$ | CH |
| 23 | $COOCH(CH_3)_2$ | $CH_2N_3$ | $CH_3$ | $CH_3$ | CH |
| 24 | $COOCH(CH_3)_2$ | $CH_2N_3$ | Cl | $OCH_3$ | CH |
| 25 | $COOCH(CH_3)_2$ | $CH_2N_3$ | $OCH_3$ | $OCH_3$ | N |
| 26 | $COOCH(CH_3)_2$ | $CH_2N_3$ | $OCH_3$ | $CH_3$ | N |
| 27 | Cl | $CH_2SCN$ | $CH_3$ | $OCH_3$ | CH |
| 28 | Cl | $CH_2N_3$ | $OCH_3$ | $OCH_3$ | CH |
| 29 | Cl | $CH_2N_3$ | $CH_3$ | $OCH_3$ | CH |
| 30 | Cl | $CH_2N_3$ | $CH_3$ | $CH_3$ | CH |
| 31 | Cl | $CH_2N_3$ | Cl | $OCH_3$ | CH |
| 32 | Cl | $CH_2N_3$ | $OCH_3$ | $OCH_3$ | N |
| 33 | Cl | $CH_2N_3$ | $OCH_3$ | $CH_3$ | N |
| 34 | $SO_2CH_3$ | $C(O)H$ | $OCH_3$ | $OCH_3$ | CH |
| 35 | $SO_2CH_3$ | $CH_2N_3$ | $OCH_3$ | $OCH_3$ | CH |
| 36 | $SO_2CH_2CH_2CH_3$ | $CH_2N_3$ | $OCH_3$ | $OCH_3$ | CH |

-continued
COMPOUNDS

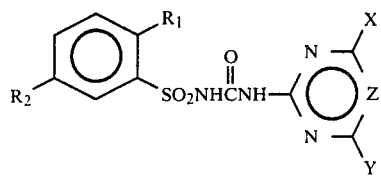

| Compound | R₁ | R₂ | X | Y | Z |
|---|---|---|---|---|---|
| 37 | SO₂CH₂CH₂CH₃ | CH₂N₃ | CH₃ | OCH₃ | CH |
| 38 | SO₂CH₂CH₂CH₃ | CH₂N₃ | OCH₃ | CH₃ | N |
| 39 | COOCH₃ | CH₂CN | OCH₃ | CH₃ | CH |
| 40 | COOCH₃ | CH₂CN | CH₃ | CH₃ | CH |
| 41 | COOCH₃ | CH₂CN | Cl | OCH₃ | CH |
| 42 | COOCH₃ | CH₂CN | OCH₃ | OCH₃ | N |
| 43 | COOCH₂CH₃ | C(O)H | OCH₃ | OCH₃ | CH |
| 44 | COOCH₂CH₃ | C(O)H | CH₃ | CH₃ | CH |
| 45 | COOCH₂CH₃ | C(O)H | Cl | OCH₃ | CH |
| 46 | COOCH₂CH₃ | C(O)H | OCH₃ | CH₃ | N |
| 47 | COOCH(CH₃)₂ | CH₂CN | OCH₃ | OCH₃ | CH |
| 48 | COOCH(CH₃)₂ | CH₂CN | CH₃ | CH₃ | CH |
| 49 | COOCH₃ | C(O)H | OCH₃ | OCH₃ | CH |
| 50 | COOCH₃ | C(O)H | OCH₃ | CH₃ | CH |
| 51 | COOCH₃ | C(O)H | CH₃ | CH₃ | CH |
| 52 | COOCH₃ | C(O)H | Cl | OCH₃ | CH |
| 53 | COOCH₃ | C(O)H | OCH₃ | CH₃ | N |
| 54 | COOCH₂CH₂CH₃ | CH₂N₃ | OCH₃ | OCH₃ | CH |
| 55 | COOCH₂CH₂CH₃ | CH₂N₃ | OCH₃ | CH₃ | CH |
| 56 | COOCH₂CH₂CH₃ | CH₂N₃ | CH₃ | CH₃ | CH |
| 57 | COOCH₂CH₂CH₃ | CH₂N₃ | Cl | OCH₃ | CH |
| 58 | COOCH₂CH₂CH₃ | CH₂N₃ | OCH₃ | OCH₃ | N |
| 59 | COOCH₂CH₂CH₃ | CH₂N₃ | OCH₃ | CH₃ | N |
| 60 | COOCH₂CH₂CH₃ | CH₂CN | OCH₃ | OCH₃ | CH |
| 61 | COOCH₂CH₂CH₃ | CH₂CN | OCH₃ | CH₃ | CH |
| 62 | COOCH₂CH₂CH₃ | CH₂CN | CH₃ | CH₃ | CH |
| 63 | COOCH₂CH₂CH₃ | CH₂CN | Cl | OCH₃ | CH |
| 64 | COOCH₂CH₂CH₃ | CH₂CN | OCH₃ | OCH₃ | N |
| 65 | COOCH₂CH₂CH₃ | CH₂CN | OCH₃ | CH₃ | N |
| 66 | OCH₂CH₂ | C(CH₃)=NOH | OCH₃ | OCH₃ | CH |
| 67 | OCH₂CH₃ | C(CH₃)=NOH | OCH₃ | CH₃ | CH |
| 68 | OCH₂CH₃ | C(CH₃)=NOH | Cl | OCH₃ | CH |
| 69 | OCH₂CH₃ | C(CH₃)=NOH | OCH₃ | OCH₃ | N |
| 70 | OCH₂CH₃ | C(CH₃)=NOH | OCH₃ | CH₃ | N |
| 71 | OCH₂CH₃ | C(CH₃)=NOCH₃ | OCH₃ | OCH₃ | CH |
| 72 | COOCH₃ | CH=NOCH₃ | OCH₃ | OCH₃ | CH |
| 73 | COOCH₃ | CH=NOCH₃ | OCH₃ | CH₃ | CH |
| 74 | COOCH₃ | CH=NOCH₃ | CH₃ | CH₃ | CH |
| 75 | COOCH₃ | CH=NOCH₃ | Cl | OCH₃ | CH |
| 76 | COOCH₃ | CH=NOCH₃ | OCH₃ | OCH₃ | N |
| 77 | COOCH₃ | CH=NOCH₃ | OCH₃ | CH₃ | N |

TABLE A

| Rate kg/ha | Compound 1 0.05 | Compound 2 0.05 | Compound 3 0.05 | Compound 4 0.05 | Compound 5 0.05 | Compound 6 0.05 | Compound 7 0.05 | Compound 8 0.05 | Compound 9 0.05 | Compound 10 0.05 | Compound 11 0.05 | Compound 12 0.05 |
|---|---|---|---|---|---|---|---|---|---|---|---|---|
| | | | | | POST-EMERGENCE | | | | | | | |
| Morningglory | 10C | 10C | 3C,9G | 2C,3H | 2C,2G | 10C | 10C | 10C | 4G | 3C,8H | | 0 |
| Cocklebur | 9C | 10C | 2C,7G | 2G | 2G | 9C | 10C | 10C | 7G | 7H | | 2H |
| Velvetleaf | 9C | 10C | 3C,7H | 2H | 2G | 10C | 10C | 10C | 4C,9G | 3C,8H | | 3G |
| Nutsedge | 2C,8G | 4C,9G | 5G | 0 | 0 | 9G | 5C,9G | 5C,9G | 4C,9G | 2C,9G | | 0 |
| Crabgrass | 2C,9G | 3C,7G | 3G | 0 | 1H | 8G | 2C,8G | 2C,8G | 2C,5G | 5G | | 0 |
| Barnyardgrass | 3C,9H | 6C,9H | 4C,9H | 0 | 2H | 4C,9G | 9C | 9C | 3C,8H | 3C,9H | | 0 |
| Cheatgrass | 9G | 6G | 5C,9G | 0 | 0 | 6C,9G | 4C,9G | 6C,9G | 2C,8G | 9G | | 0 |
| Wild Oats | 3C,9G | 3C,9G | 5C,9G | 1H | 0 | 4C,9G | 6C,9G | 9C | 3C,5G | 3C,9H | | 0 |
| Wheat | 8G | 7G | 8G | 0 | 2H | 4C,9G | 9C | 9C | 9G | 9G | | 0 |
| Corn | 5C,9H | 4U,9C | 5C,9G | 2H | 2H | 4U,9G | 7U,9C | 7U,9C | 3C,9H | 9G | | 2C,7H |
| Soybean | 5C,9G | 9C | 4C,9G | 1H | 3H | 5C,9G | 5C,9G | 9C | 5C,9G | 4C,9G | | 3C,8G |
| Rice | 5C,9G | 6C,9G | 5C,9G | 2G | 5G | 5C,9G | 9C | 9C | 2C,9G | 5C,9G | | 6G |
| Sorghum | 4C,9H | 5C,9H | 4C,9G | 0 | 5G | 4C,9G | 9C | 9C | 3C,9H | 9H | | 6G |
| Sugar beet | 9C | 9C | 5C,8H | 1H | 3H | 3C,9H | 9C | 9C | 9C | 3C,8G | | 2H |
| Cotton | 9C | 9C | 4C,7H | 0 | 0 | 3C,9H | 9C | 9C | 2C,9G | 3C,9G | | 2C,2G |
| Giant Foxtail | | | | | | | | | | | | |
| Barley | | | | | | | | | | | | |
| | | | | | PRE-EMERGENCE | | | | | | | |
| Morningglory | 9G | 9G | 8G | 5G | 2G | 9G | 9G | 4C,9G | 9G | 8G | | 0 |
| Cocklebur | 8H | 9H | 5G | 0 | 0 | 10H | 9H | 3C,9H | 8G | 8H | | 8H |
| Velvetleaf | 9G | 9C | — | 0 | 0 | 9C | 9G | 4C,9G | 8G | 4C,9G | | 3G |
| Nutsedge | 3C,8G | 4C,8G | 0 | 4G | 2G | 4C,9G | 10E | 10E | 4G | 5G | | 0 |
| Crabgrass | 0 | 2C,8G | 7G | 2G | 0 | 4C,8G | 3C,7G | 3C,7G | 3G | 4G | | 0 |
| Barnyardgrass | 4C,9G | 3C,8G | 2H | 4G | 0 | 4C,9G | 5C,9H | 5C,9H | 3C,8H | 9H | | 0 |
| Cheatgrass | 8G | 4C,8G | 2C,5G | 2G | 0 | 4C,8G | 4C,8G | 4C,8G | 8H | 3C,9H | | 0 |
| Wild Oats | 3C,8G | 4C,8G | 3C,6G | 2G | 0 | 3C,8G | 5C,9G | 5C,9G | 3C,8G | 3C,9G | | 0 |
| Wheat | 3C,9G | 6G | 5G | 4G | 0 | 5G | 10E | 10E | 7G | 9G | | 0 |
| Corn | 3C,9G | 4G | 4G | 2G | 2G | 8G | 8G | 8G | 3C,7G | 2C,7G | | 2C,2H |
| Soybean | 8H | 3C,5H | 3G | 0 | 4H | 2G | 2G | 2G | 3C,5H | 3C,5H | | 0 |
| Rice | 3C,9H | 4C,8H | 2C | 2G | 2G | 9H | 9H | 9H | 2C,8G | 4C,8H | | 0 |
| Sorghum | 10E | 4C,9H | 3C,5G | 0 | 0 | 2C,9G | 8H | 8H | 3C,9H | 8H | | 2C,9G |
| Sugar beet | 7G | 10C | 4C,8H | 2G | — | 10C | 5C,9H | 5C,9H | 9C | 10E | | 0 |
| Cotton | 8G | 2C,8G | 8G | — | — | 9C | 4C,9G | 4C,9G | 10C | 4C,9G | | 8G |
| Giant Foxtail | | | | | | | | | | 9G | | 3G |
| Barley | | | | | | | | | | | | |

| Rate kg/ha | Compound 13 0.05 | Compound 14 0.05 | Compound 15 0.4 | Compound 16 0.05 | Compound 17 0.05 | Compound 18 0.05 | Compound 19 0.05 | Compound 20 0.05 | Cmpd. 21 0.05 | Cmpd. 22 0.05 | Cmpd. 23 0.05 | Cmpd. 24 0.05 | Cmpd. 25 0.05 | Cmpd. 26 0.05 |
|---|---|---|---|---|---|---|---|---|---|---|---|---|---|---|
| | | | | | | POST-EMERGENCE | | | | | | | | |
| Morningglory | 2C,4G | 3C,9G | 4C,8H | 1C,1H | 3G | 1H | 3G | 0 | 10C | 10C | 9C | 9C | 9C | 10C |
| Cocklebur | 5G | 5C,9G | 9H | 3C,9H | 5C,9H | 6G | 4C,9G | 0 | 10C | 9C | 10C | 9C | 10C | 10C |
| Velvetleaf | 2C,4G | 2C,6H | 4C,8H | 5C,9G | 4C,9G | 6H | 2C,7G | 0 | 10C | 4C,9G | 9C | 5C,9G | 5C,9G | 10C |
| Nutsedge | 2C,4G | 0 | 0 | 4C,9G | 3C,6G | 0 | 5G | 5C,9G | 5C,9G | 0 | 4C,9G | 2C,8G | 5C,9G | 5C,9G |
| Crabgrass | 0 | 2G | 5C,9G | 3G | 3C,4G | 0 | 4G | 4G | 0 | 3G | 0 | 3C,8H | 2G | 0 |
| Barnyardgrass | 0 | 5G | 4C,9G | 3C,9H | 3C,9H | 1C,2H | 3C,8H | 3C,8H | 10C | 3C,7H | 3C,8H | 3C,8H | 3C,8H | 4C,9H |
| Cheatgrass | 0 | 5G | 6C,9H | 2G | 4G | 0 | 0 | 0 | 5C,9G | 9G | 2G | 2G | 7G | 2C,9G |
| Wild Oats | 2C,3H | 3C,8G | 3C,9G | 3C,9H | 3C,9H | 0 | 0 | 4G | 2C,5G | 9G | 9G | 0 | 3G | 9C |
| Wheat | 0 | 3C,9G | 2G | 4G | 2G | 0 | 0 | 3C,8H | 4C,9G | 10C | 10C | 2C,5G | 4G | 9C |
| Corn | 0 | 2C,9H | 3C,9G | 2G | 0 | 3C,7H | 4C,9G | 9C | 9C | 9C | 9C | 9C | 10C |

TABLE A-continued

| | Cmpd. 27 0.05 | Cmpd. 28 0.05 | Cmpd. 29 0.05 | Cmpd. 30 0.05 | Cmpd. 31 0.05 | Cmpd. 32 0.05 | Cmpd. 33 0.05 | Cmpd. 34 0.05 | Cmpd. 35 0.05 | Cmpd. 36 0.05 | Cmpd. 37 0.05 | Cmpd. 38 0.05 | Cmpd. 39 0.05 | Cmpd. 40 0.05 | Cmpd. 41 0.05 | Cmpd. 42 0.05 | Cmpd. 43 0.05 |
|---|---|---|---|---|---|---|---|---|---|---|---|---|---|---|---|---|---|
| Soybean | 3H | 5C,9G | 5C,9G | 5C,9G | 2C,7G | 3C,7G | 5C,9G | 2H | 3H,5G | 3C,9G | 4C,9G | 9C | 9C | 3C,9G | 3H,4G | 5C,9G | 10C |
| Rice | 5G | 2C,8G | 5C,9G | 5C,9G | 4C,9G | 4C,9G | 5G | 5G | 5C,9G | 9C | 9C | 9C | 4C,9G | 9C | 4C,9G | 9C | 9C |
| Sorghum | 2C,5G | 3C,8H | 3C,9H | 3C,9H | 5C,9G | 4C,9G | 3C,8G | 2C,5G | 4C,9G | 9C | 9C | 9C | 2C,9H | 9C | 9H | 3C,9H | 3C,9H |
| Sugar beet | 3C,5G | 4C,9G | 9C | 9C | 3C,6G | 4G | 4G | 2G | 3C,6H | 4C,9G | 5G | 9C | 9C | 10C | 5C,9G | 5C,9G | 10C |
| Cotton | 3C,7G | 2C,5G | 4C,8G | 9C | 5C,9G | 9C | 9C | 4G | 3C,5G | 4C,9G | 0 | 3C,6G | 5C,9G | 4C,9G | 10C | 10C | 10C |
| Giant Foxtail | | | | | | | | | | 3C,6G | 3C,8H | 8G | 9G | 9C | 1H | 4G | 4C,9G |
| Barley | | | | | | | | | | 8G | | | | | 2G | | 7G |

PRE-EMERGENCE

| | | | | | | | | | | | | | | | | | |
|---|---|---|---|---|---|---|---|---|---|---|---|---|---|---|---|---|---|
| Morningglory | 8G | 7H | 7G | 9G | 8G | 10C | 9G | 2H | 8G | 10C | 9G | 9G | 9H | 7H | 9G | 8G | 9G |
| Cocklebur | — | 9H | 7H | 8H | 9H | 10C | 8H | 7H | 8H | 9C | 8G | 9H | 9H | 9H | 9H | — | — |
| Velvetleaf | 5G | 4G | 5H | 5C,9G | 8G | 2C,5G | 10C | 4G | 7G | 9C | 5G | 10C | 8G | 8G | 8G | 6G | 4C,9G |
| Nutsedge | 5G | 0 | 4G | 7G | 2C,7G | 5G | 9C | 0 | 0 | 4C,9G | 0 | 9G | 9G | 9G | 0 | 8G | 10E |
| Crabgrass | 2G | 0 | 0 | 5G | 0 | 4G | 8G | 0 | 0 | 3G | 3C,7G | 0 | 8G | 2G | 0 | 4G | 3G |
| Barnyardgrass | 0 | 1C | 2C,5G | 3C,9H | 3C,9H | 3C,9H | 4C,8G | 2C | 5H | 4C,9G | 9G | 4C,9H | 4C,9G | 4C,8H | 2C,5G | 3C,6G | 3C,8H |
| Cheatgrass | 5H | 2G | 6G | 3C,8H | 0 | 0 | 9C | 0 | 0 | 8G | 3C,8H | 3C,9H | 9G | 9G | 4G | 6G | 9H |
| Wild Oats | 0 | 2C | 2C,8G | 5C,9G | 3C,6G | 5G | 4C,8G | 2C | 0 | 2G | 2G | 7G | 3C,7G | 7G | 0 | 2G | 2C,8G |
| Wheat | 0 | 6G | 6G | 2C,9G | 3C,8G | 3G | 9C,9G | 0 | 5H | 3G | 3G | 9H | 9G | 8G | 0 | 4G | 3C,9H |
| Corn | 5G | 2C,6G | 3C,9H | 3C,9H | 9G | 3C,9H | 5C,9G | 3C,6G | 3C,6G | 9G | 9G | 3C,7G | 9H | 5C,9G | 7G | 3C,9G | 3C,9G |
| Soybean | 2C,2G | 6H | 3C,6H | 9H | 3G | 4C,9G | 4C,9G | 1C | 1C | 2H | 4C,9G | 2C,7H | 3C,8H | 4C,6H | 3C,7G | 2C,6G | 3C,7H |
| Rice | 2C | 8G | 2C,8H | 3C,4G | 9G | 4C,9G | 6C,9G | 2C,5G | 2C,6G | 3C,9G | 4C,9G | 3C,8G | 2C,8G | 3C,9H | 4C,8H | 8G | 9H |
| Sorghum | 2C,4G | 2C,7H | 2C,8H | 10E | 4C,8H | 3C,8H | 5C,9G | 5G | 3C,9H | 5C,9G | 2C,7G | 4C,9H | 9H | 5C,9G | 9G | 3C,8G | 3C,9H |
| Sugar beet | 6G | 10C | 3C,9H | 5C,9G | 4C,8H | 4C,8H | 9C | 9G | 3C,9H | 4C,9G | 4C,9H | 4C,8H | 9G | 4C,9G | 9G | 5C,9G | 5C,9G |
| Cotton | 6G | 4C,9G | 4C,9G | 9C | 4C,9G | 4C,9G | 5C,9G | 5G | 3C,9G | 4G | 2G | 2G | 9G | 9G | 8G | 8G | 9G |
| Giant Foxtail | 0 | 3C,7G | 0 | 9G | 7G | 8G | 9C | 5G | 3C,7G | 9G | 4C,9G | 3C,7G | 3C,6G | 4C,8G | 2C,2G | 2C,5G | 3C,5G |
| Barley | 0 | 2G | 7G | | | | | | | | | 9G | | | 7G | 8G | 9G |

POSTEMERGENCE

| | | | | | | | | | | | | | | | | | |
|---|---|---|---|---|---|---|---|---|---|---|---|---|---|---|---|---|---|
| Morningglory | 3C,7H | 10C | 0 | 3G | 4C,9H | 10C | 10C | 10C | 8G | 10C | 5C,9G | 3C,8G | 10C | 10C | 10C | 10C | 10C |
| Cocklebur | 0 | 8H | 4C,9H | 4C,9H | 10C | 10C | 10C | 10C | 8H | 9C | 4C,9H | 4C,9G | 10C | 10C | 10C | 10C | 10C |
| Velvetleaf | 0 | 10C | 8G | 0 | 2C,5G | 4C,8G | 10C | 10C | 7G | 9C | 5C,9G | 4C,9H | 10C | 10C | 9C | 6G | 3C,8G |
| Nutsedge | 6C,9G | 4C,8G | 0 | 0 | 5G | 2G | 9C | 5C,9G | 0 | 4C,9G | 5G | 2G | 9C | 5C,9G | 4C,8G | 9C | 2G |
| Crabgrass | 0 | 0 | 0 | 4H | 3C,9H | 2G | 10C | 8G | 5H | 4C,9G | 3C,8H | 2C,5H | 9C | 2C,9G | 4C,9G | 3C,7G | 2G |
| Barnyardgrass | 5H | 4C,9H | 0 | 0 | 0 | 4C,9H | 10C | 9C | 0 | 8G | 2G | 3C,9H | 9C | 2C,9G | 5C,9G | 2C,9G | 1C,5G |
| Cheatgrass | 0 | 7G | 0 | 0 | 0 | 0 | 5G | 4C,9G | 0 | 0 | 3G | 9H | 9C | 10C | 9G | 10C | 0 |
| Wild Oats | 5H | 2G | 0 | 0 | 3C,9H | 5G | 3G | 6C,9G | 3C,6G | 0 | 3G | 7G | 9H | 2C,9G | 0 | 9C | 0 |
| Wheat | 0 | 3C,8H | 7G | 2G | 4C,9H | 4C,9G | 5C,9G | 5C,9G | 1C | 3C,9G | 9G | 3C,3C,8H | 3C,8H | 5C,9G | 7G | 10C | 4C,9G |
| Corn | 5H | 4C,9G | 5G | 2G | 3C,9H | 4C,9G | 9C | 9C | 2C,6G | 5C,9G | 4C,9H | 2C,7H | 3C,8H | 4C,6H | 0 | 9C | 2C,6G |
| Soybean | 3H | 3C,9G | 6C,9G | 9H | 4C,8H | 5C,9G | 6C,9G | 9C | 3C,4G | 4C,9G | 4C,8H | 3C,8H | 9H | 5C,9G | 3C,7G | 2C,6G | 4C,9G |
| Rice | 0 | 10C | 5G | 10E | 4C,9G | 10C | 9C | 5C,9G | 3C,9H | 5C,9G | 2C,7G | 3C,8H | 3C,8H | 4C,9G | 4C,8H | 8G | 3C,9G |
| Sorghum | 3G | 4C,9G | 9C | 5C,9G | 4C,9G | 4C,9G | 10C | 9C | 3C,9H | 4C,9G | 4C,7H | 4C,9G | 9H | 5C,9G | 9G | 3C,8G | 2C,4G |
| Cotton | 4C,6G | 3C,7G | 0 | 9C | 2C,4G | 10C | 10C | 10C | 3C,8H | 4C,9G | 4C,9H | 4C,8H | 10C | 10C | 10C | 9C | 9C |
| Giant Foxtail | 0 | 2C | 0 | 4C,8G | 9C | 6G | 5C,9G | 5C,9G | 3C,7G | 4G | 2G | 2G | 10C | 5C,9G | 4C,9G | 3C,8G | 1C,6G |
| Barley | 0 | 5G | 0 | 0 | 2C,2G | 0 | 9C | 9C | 7G | 9G | 4C,9G | 0 | 9C | 9G | 9G | 8G | 6G |

PREEMERGENCE

| | | | | | | | | | | | | | | | | | |
|---|---|---|---|---|---|---|---|---|---|---|---|---|---|---|---|---|---|
| Morningglory | 5G | 7G | 5G | 7G | 8G | 10C | 10C | 10C | 8G | 1H | 3G | 7H | 10E | 9H | 9G | 9G | 7G |
| Cocklebur | 8G | 8H | 9H | 9H | 9H | — | — | 9H | 8H | 3H | 9H | 7H | 9H | 9C | 9H | 8H | 9H |
| Velvetleaf | 8G | 9G | 9G | 9G | 9C | 6G | 8G | 8G | 7G | 5G | 7H | 7G | 10E | 9C | 10C | 8G | 2C,4G |
| Nutsedge | 0 | 10E | 5G | 10E | 10C | 10E | 9G | 9G | 0 | 3G | 0 | 0 | 10C | 10C | 10E | 10E | 9G |
| Crabgrass | 0 | 3G | 5G | 2G | 3C,7G | 2C,7G | 4C,9H | 3G | 3C,9H | 0 | 0 | 0 | 5C,9G | 5C,9G | 3G | 2C,5G | 9H |
| Barnyardgrass | 0 | 4C,8H | 2G | 2G | 3C,7G | 2C,8H | | | | 7G | 7H | 2C | 5C,9H | 9H | 3C,9H | 8H | 9H |

TABLE A-continued

| | Cmpd. 44 | Cmpd. 45 | Cmpd. 46 | Cmpd. 47 | Cmpd. 48 | Cmpd. 49 | Cmpd. 50 | Cmpd. 51 | Cmpd. 52 | Cmpd. 53 | Cmpd. 54 | Cmpd. 55 | Cmpd. 56 | Cmpd. 57 | Cmpd. 58 | Cmpd. 59 | Cmpd. 60 |
|---|---|---|---|---|---|---|---|---|---|---|---|---|---|---|---|---|---|
| Cheatgrass | 0 | 5G | 3C,7G | 0 | 0 | 4G | 0 | 9H | 9H | 3G | 6G | 0 | 10E | 10E | 8G | 7G | 4G |
| Wild Oats | 0 | 2G | . | 4G | 0 | 5G | 2G | 2C,8G | 3C,8G | 0 | 2G | 0 | 6C,9H | 5C,9H | 6C,9H | 4C,9H | 5G |
| Wheat | 0 | 0 | 5G | 0 | 0 | 0 | 0 | 9H | 10H | 0 | 3G | 0 | 10E | 10E | 4C,9H | 4C,9H | 4G |
| Corn | 2C,3G | 7G | 3C,8H | 3G | 2C,6G | 2C,7G | 2C,5G | 2C,5G | 5C,9H | 3C,7G | 2C,6G | 6G | 5C,9H | 9H | 9H | 4C,8H | 2C,7H |
| Soybean | 0 | 2C,5H | 3C,8H | 1C | 0 | 3C,5H | 3C,3H | 7H | 3C,7G | 2H | 3C,7H | 2C | 10E | 10E | 9H | 10E | 2C,7H |
| Rice | 4G | 2C,6H | 4C,9H | 3G | 3G | 9H | 7G | 10E | 10E | 8H | 3C,7H | 2C,5G | 10E | 10E | 10E | 10E | 4C,9H |
| Sorghum | 0 | 2C,4H | 3C,5G | 5G | 5G | 5G | 3C,3H | 5C,9H | 10H | 3C,7G | 4C,9H | 2C,5G | 10H | 10E | 5C,9H | 5C,9H | 4C,8H |
| Sugar beet | 8G | 10C | 9C | 8G | 9G | 10C | 8G | 9G | 8G | 7H | 5H | 5G | 9C | 5C,9H | 5C,9G | 4C,9G | 2C,9H |
| Cotton | 3G | 7G | 7G | 7G | 8G | 7G | 5G | 9G | 9G | 2G | 0 | 6G | 9C | 9C | 9G | 9G | 2C,4G |
| Giant Foxtail | 0 | 4C,6G | 4C,7G | 5G | 4G | 8G | 6G | 4C,9H | 4C,9H | 2G | 3G | 1C | 4C,9H | 10C | 3C,9H | 3C,8G | 2C,4G |
| Barley | 2G | 7G | 9G | 3G | 2C,8G | 2C,8G | 2G | 9G | 9G | 9G | 3C,9H | 3G | 9C | 5C,9H | 3C,9H | 4C,9H | 7G |
| Rate kg/ha | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |

POSTEMERGENCE

| | Cmpd. 61 | Cmpd. 62 | Cmpd. 63 | Cmpd. 64 | Cmpd. 65 | Cmpd. 67 | Cmpd. 68 | Cmpd. 69 | Cmpd. 70 | Cmpd. 71 | Cmpd. 72 | Cmpd. 73 | Cmpd. 74 | Cmpd. 75 | Cmpd. 76 | Cmpd. 77 |
|---|---|---|---|---|---|---|---|---|---|---|---|---|---|---|---|---|
| Morningglory | 5C,9H | 2C,5G | 5C,8H | 9G | 8G | 10C | 9C | 10C | 3C,8H | 0 | 10C | 6C,9H | 3G | 10C | 10C | 10C |
| Cocklebur | 2C,8H | 2C,5H | 4C,9H | 9H | 8H | 10C | 4C,9H | 9H | 3C,8H | 1H | 10C | 2C,3H | 8H | 10C | 5H | 10C |
| Velvetleaf | 2H,5G | 0 | 2G | 3C,7G | 3C,8G | 10C | 3C,6G | 2H | 2C,3H | 1C,5G | 10C | 10C | 5G | 9C | 9C | 10C |
| Nutsedge | 2C,8G | 3C,8G | 2C,8H | 5G | 3C,9G | 5C,9G | 4G | 4G | 2C,3H | 7G | 3C,9G | 2C,7G | 0 | 9G | 9G | 4C,9G |
| Crabgrass | 0 | 0 | 0 | 0 | 2C,9G | 4C,9G | 3G | 3G | 2G | 2G | 3G | 0 | 2G | 9G | 4G | 4G |
| Barnyardgrass | 4C,9H | 2G | 1C,3G | 9H | 9C | 2C,7G | 2C,9H | 9H | 5G | 3C,7H | 4C,8G | 3G | 1C,7G | 5C,9H | 5C,9H | 5C,9H |
| Cheatgrass | 3G | 8H | 9C | 8G | 4C,9H | 9C | 6G | 4G | 2G | 2G | 3C,9G | 1C,7G | 6G | 2C,6H | 2C,7G | 9G |
| Wild Oats | 2G | 2G | 2C | 6G | 4C,9G | 6G | 8G | 3G | 8G | 0 | 2C,5G | 8G | 6G | 2C,6G | 9G | 3C,5G |
| Wheat | 0 | 0 | 0 | 7G | 2C,5G | 4G | 5G | 0 | 7G | 8G | 9G | 7G | 3G | 0 | 2G | 6G |
| Corn | 3C,9G | 2C,4H | 9G | 3C,9H | 2C,6G | 2C,8G | 9H | 0 | 8G | 3C,5G | 3C,5G | 3C,9H | 2G | 2G | 3C,7H | 2U,9G |
| Soybean | 2C,7H | 1C,1H | 2H | 7H | 6G | 5C,9G | 2C,3G | 0 | 3G | 3C,9G | 2C,3G | 2C,8G | 5G | 3C,7H | 5C,9G | 9C |
| Rice | 3C,9G | 2G | 5C,9G | 3C,7H | 5C,9G | 9H | 5C,9H | 9H | 8G | 3C,7H | 3C,7H | 2C,9G | 3C,9G | 5C,9G | 9G | 4C,9G |
| Sorghum | 3C,9G | 8G | 2C,8G | 9H | 9C | 9G | 9H | 4H | 3C | 2C,7H | 3C,7H | 2C,9G | 5C,9G | 3C,9G | 3C,9G | 4C,9G |
| Sugar beet | 2C,6G | 0 | 3C,7H | 9H | 9G | 5C,9H | 9H | 9G | 3C | 4C,8G | 2C,4G | 4C | 10C | 9C | 4C,8G | 9C |
| Cotton | 3C,8G | 3C,8G | 2C,6G | 3C,7G | 9G | 2C,4G | 3G | 7G | 3C,7H | 4C | 0 | 3G | 5G | 9G | 2G | 10C |
| Giant Foxtail | 2C,9G | 0 | 2C,5G | 8G | 8G | 2C,4G | 2G | 3G | 2G | 2G | 2C,4G | 2G | 5G | 7G | 6G | 3C,6G |
| Barley | 6G | 7G | 0 | 7G | 9G | 3G | 4G | 2G | 5G | 5G | 7G | 4G | 3G | 5G | 5G | 9G |
| Rate kg/ha | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |

PREEMERGENCE

TABLE A-continued

POSTEMERGENCE

| | | | | | | | | | | | | | | | | |
|---|---|---|---|---|---|---|---|---|---|---|---|---|---|---|---|---|
| Morningglory | 10C | 10C | 10C | 10C | 10C | 2C,5G | 2C,6G | 2H | 1H | 2C,4G | 4C,9H | 10C | 9C | 10C | 10C | 10C |
| Cocklebur | 10C | 10C | 10C | 10C | 10C | 3C,9H | 2C,6G | 2H | — | 5H | 3C,9H | 10C | 10C | 10C | 10C | 10C |
| Velvetleaf | 10C | 9C | 3C,8G | 9C | 9C | 2C,9G | 2C,5H | 1H | 2C,7H | 2C,5G | 9C | 10C | 10C | 9C | 2C,8G | 10C |
| Nutsedge | 4C,9G | 3C,9G | 3G | 2C,8G | 2C,8G | 3C,9G | 2C,5G | 4G | 5H | 0 | 2C,8G | 5C,9G | 3C,8G | 6C,9G | 6C,9G | 9G |
| Crabgrass | 3G | 5G | 2G | 0 | 0 | 5G | 0 | 0 | 0 | 0 | 5G | 7G | 3C,8H | 0 | 3G | 6G |
| Barnyardgrass | 9C | 9C | 4C,9H | 3C,8G | 3C,8G | 3C,9H | 9H | 7H | 0 | 6H | 2C,7G | 9C | 9C | 9C | 9H | 9C |
| Cheatgrass | 4C,9G | 3C,9G | 2C,4G | 2C,5G | 8G | 4G | 6G | 0 | 7H | 0 | 2C,8G | 9C | 9C | 9C | 9C | 5C,9G |
| Wild Oats | 2C,7G | 5C,9G | 2G | 2C,7G | 2C,9G | 5G | 2C,7G | 0 | 0 | 2C,3G | 2C,8G | 3C,8G | 9G | 9G | 2C,5G | 9C |
| Wheat | 3C,9G | 3C,9G | 4G | 2G | 3G | 2G | 5G | 0 | 2G | 0 | 6G | 2C,9G | 5C,9G | 9G | 3G | 4C,9G |
| Corn | 9C | 2U,9G | 3C,7G | 3C,3H | 2C,7G | 3C,9H | 2C,9H | 0 | 4G | 0 | 3C,9H | 4U,9G | 2U,9G | 3C,9H | 3C,8H | 2C,8G |
| Soybean | 9C | 9C | 3C,3H | 4C,9G | 4C,9G | 5H | 3C,7H | 1H | 2C,5G | 3C,3H | 4C,9H | 9C | 9C | 5C,9G | 9C | 9C |
| Rice | 5C,9G | 5C,9G | 9G | 2C,9G | 2C,9G | 2C,7G | 3C,7G | 2G | 3C,7H | 8G | 2C,6G | 9C | 9C | 9C | 4C,9G | 5C,9G |
| Sorghum | 5C,9G | 4C,9G | 4C,9G | 2C,9G | 5C,9G | 3C,9G | 3C,8H | 5G | 3C,9H | 3C,9H | 2C,8G | 9C | 9C | 5C,9G | 4C,9G | 9C |
| Sugar beet | 9C | 9C | 4C,8H | 3C,9H | 9C | 3C,6G | 3C,8G | 3G | 3C,9H | 3C,7H | 2C,8G | 10C | 10C | 9C | 10C | 5C,9G |
| Cotton | 10C | 10C | 9C | 9C | 9C | 7G | 3C,8G | 2G | 4G | 2C | 6G | 10C | 9C | 10C | 4C,9G | 4C,9G |
| Giant Foxtail | 3C,8G | 3C,8G | 4G | 4G | 2C,7G | 2C,6G | 2C,6G | 2G | 2G | 2G | 6G | 9C | 6C,9G | 6C,9H | 4C,9G | 4C,9G |
| Barley | 9H | 9H | 3C,6G | 0 | 2C,6G | 8G | 7G | 0 | 3G | 0 | 3C,8G | 7G | 4C,9G | 4C,9H | 4C,9G | 3C,9G |

PREEMERGENCE

| | | | | | | | | | | | | | | | | |
|---|---|---|---|---|---|---|---|---|---|---|---|---|---|---|---|---|
| Morningglory | 4C,8G | 5H | 8G | 2C,8G | 2C,8G | 0 | 0 | 0 | 3G | 0 | 2G | 9G | 9G | 8G | 9G | 9G |
| Cocklebur | 7H | 6H | 2C,4H | 3C,7H | 6H | 2H | 0 | — | — | 0 | 5H | — | 9H | 3C,5H | 9H | 9H |
| Velvetleaf | 7H | 3C,8H | 7G | 5G | 4G | 0 | 0 | 0 | 3G | 0 | 0 | 9C | 5C,9G | 5H | 4C,8H | 4C,8H |
| Nutsedge | 8G | 8G | 5G | 8G | 2C,8G | 0 | 0 | 3G | 0 | 0 | 7H | 10E | 10E | 9G | 5G | 4G |
| Crabgrass | 3G | 0 | 0 | 0 | 0 | 0 | 5G | 0 | 3G | 3G | 2C,6H | 3G | 2G | 0 | 0 | 0 |
| Barnyardgrass | 9H | 7G | 8H | 7H | 7H | 0 | 7G | 9H | 3G | 3G | 2C,6H | 9H | 9H | 9H | 8H | 8H |
| Cheatgrass | 5C,9G | 8G | 5G | 2G | 6H | 0 | 2G | 0 | 3G | 0 | 0 | 9H | 9H | 9H | 9H | 9H |
| Wild Oats | 4C,8G | 3C,8H | 2G | 2C,3G | 3C,8G | 0 | 2G | 0 | 4G | 0 | 2C,6H | 3C,9G | 8G | 3C,6G | 3C,9H | 4C,9G |
| Wheat | 4C,9H | 9G | 3G | 0 | 0 | 2G | 0 | 0 | 0 | 2C,6H | 0 | 3C,9H | 8G | 5G | 9H | 4C,9H |
| Corn | 3C,9H | 3C,9H | 3C,4G | 2C,5G | 3C,6G | 0 | 2G | 0 | 2G | 0 | 2G | 3C,9G | 8G | 3C,9H | 7G | 2C,9G |
| Soybean | 4C,7H | 7G | 0 | 3C,7H | 4C,8H | 2G | 2C,7G | 2G | 0 | 3G | 0 | 7H | 9G | 7H | 3C,8H | 9H |
| Rice | 5C,9H | 9H | 7H | 9H | 10H | 4G | 1H | 0 | 4G | 0 | 3C,7G | 3C,9H | 7H | 3C,9H | 10E | 10E |
| Sorghum | 9H | 9H | 9H | 3C,8H | 9H | 5G | 3G | 4G | 4G | 5G | 2C,9H | 9H | 9H | 9H | 9H | 10H |
| Sugar beet | 9C | 3C,7G | 8G | 3C,8G | 3C,9G | 3G | 8G | 4G | 0 | 6G | 6G | 4C,9G | 9G | 8G | 4C,8G | 4C,8G |
| Cotton | 3C,8H | 2C,7G | 9G | 2C,5G | 2C,8G | 0 | 2G | 0 | 0 | 5G | 0 | 7G | 7G | 9G | 9G | 9G |
| Giant Foxtail | 6G | 5G | 4G | 0 | 0 | 0 | 5G | 4G | 10H | — | 5H | 5G | 7G | 3C,6G | 5G | 5G |
| Barley | 9G | 8G | 0 | 2G | 2G | 0 | 7G | 5G | 3G | 4G | 0 | 9G | 9G | 7G | 9G | 9G |

What is claimed is:

1. A compound of the formula:

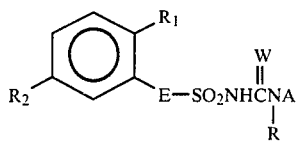

wherein

E is CH$_2$ or a single bond;
W is O or S;
R is H or CH$_3$;
R$_1$ is F, Cl, Br, NO$_2$, C$_1$-C$_4$ alkyl, C$_2$-C$_4$ alkenyl, C$_2$-C$_4$ haloalkenyl, C$_2$-C$_4$ alkynyl, C$_1$-C$_4$ haloalkyl, C$_1$-C$_4$ alkoxy, OCH$_2$CH$_2$OCH$_3$, C$_1$-C$_4$ haloalkoxy, C$_3$-C$_4$ alkenyloxy, C$_2$-C$_4$ haloalkenyloxy, C$_3$-C$_4$ alkynyloxy, CO$_2$R$_3$, CONR$_4$R$_5$, SO$_2$NR$_4$R$_5$, SO$_2$N(OCH$_3$)CH$_3$, S(O)$_n$R$_6$, OSO$_2$R$_7$, C$_1$-C$_2$ alkyl substituted with C$_1$-C$_2$ alkoxy, OH or C$_1$-C$_2$ alkylthio,

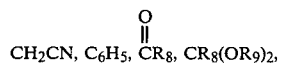

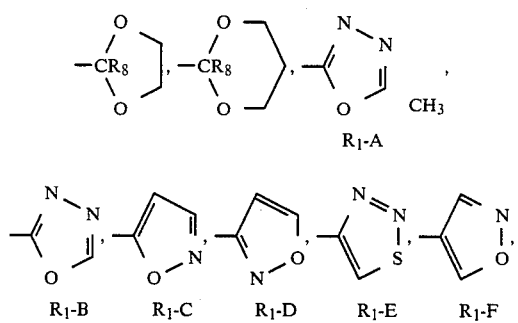

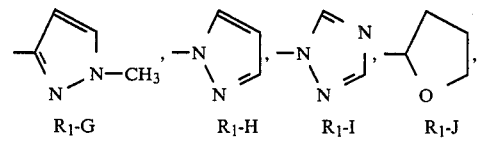

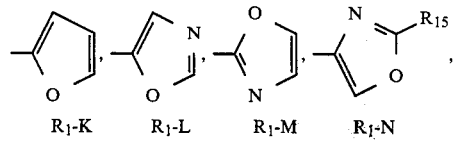

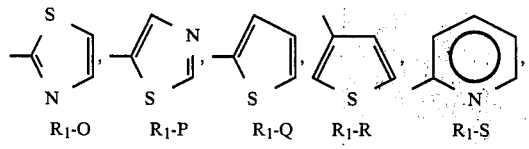

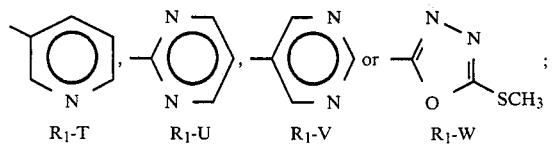

R$_2$ is

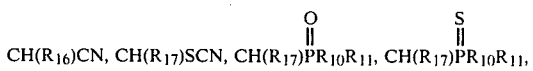

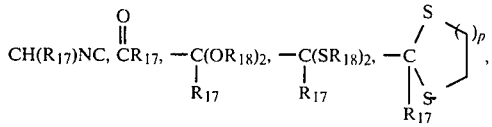

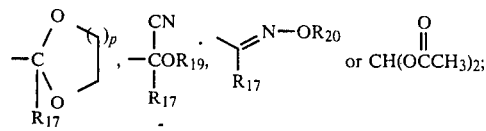

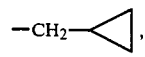 or CH(OCCH$_3$)$_2$;

R$_3$ is C$_1$-C$_4$ alkyl, C$_3$-C$_4$ alkenyl, C$_3$-C$_4$ alkynyl,

—CH$_2$—◁,

CH$_2$CH$_2$Cl, CH$_2$CH$_2$F, or C$_1$-C$_2$ alkyl substituted with OCH$_3$ or SCH$_3$;
R$_4$ is C$_1$-C$_3$ alkyl;
R$_5$ is H or C$_1$-C$_3$ alkyl;
R$_4$ and R$_5$ may be taken together to form (CH$_2$)$_3$ or (CH$_2$)$_4$;
R$_6$ is C$_1$-C$_3$ alkyl, CH$_2$CH=CH$_2$ or CH$_2$C≡CH;
R$_7$ is C$_1$-C$_3$ alkyl or N(CH$_3$)$_2$;
R$_8$ is H, C$_1$-C$_4$ alkyl, C$_3$-C$_4$ alkenyl, C$_3$-C$_4$ alkynyl, CH$_2$CH$_2$Cl, CH$_2$CH$_2$F, C$_1$-C$_2$ alkyl substituted with OCH$_3$ or SCH$_3$ and C$_3$-C$_6$ cycloalkyl;
R$_9$ is C$_1$-C$_2$ alkyl;
R$_{10}$ and R$_{11}$ are independently C$_1$-C$_2$ alkyl, C$_1$-C$_2$ alkoxy, C$_1$-C$_2$ alkylthio, NHCH$_3$ or N(CH$_3$)$_2$;
R$_{12}$ and R$_{13}$ are independently H or C$_1$-C$_2$ alkyl;
R$_{14}$ is C$_1$-C$_3$ alkyl;
R$_{15}$ is H or CH$_3$;
R$_{16}$ is H, C$_1$-C$_2$ alkyl or F;
R$_{17}$ is H or C$_1$-C$_2$ alkyl;
R$_{18}$ is C$_1$-C$_2$ alkyl;
R$_{19}$ is H, Si(CH$_3$)$_3$ or C$_1$-C$_2$ alkyl;
R$_{20}$ is H or C$_1$-C$_2$ alkyl;
p is 1 or 2;
n is 0, 1, or 2;
A is

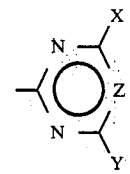

X is H, C$_1$-C$_4$ alkyl, C$_1$-C$_4$ alkoxy, C$_1$-C$_4$ haloalkoxy, C$_1$-C$_4$ haloalkyl, C$_1$-C$_4$ haloalkylthio, C$_1$-C$_4$ alkylthio, halogen, C$_2$-C$_5$ alkoxyalkyl, C$_2$-C$_5$ alkoxyalkoxy, amino, C$_1$-C$_3$ alkylamino or di(C$_1$-C$_3$ alkyl)amino;

Y is H, C$_1$-C$_4$ alkyl, C$_1$-C$_4$ alkoxy, C$_1$-C$_4$ haloalkoxy, C$_1$-C$_4$ haloalkylthio, C$_1$-C$_4$ alkylthio, C$_2$-C$_5$ alkoxyalkyl, C$_2$-C$_5$ alkoxyalkoxy, amino, C$_1$-C$_3$ alkylamino, di(C$_1$-C$_3$ alkyl)amino, C$_3$-C$_4$ alkenyloxy, C$_3$-C$_4$ alkynyloxy, C$_2$-C$_5$ alkylthioalkyl, C$_2$-C$_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido, cyano,

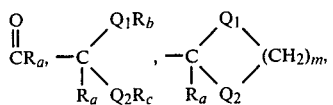

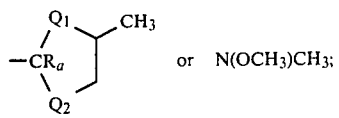 or $N(OCH_3)CH_3$;

m is 2 or 3;
$Q_1$ and $Q_2$ are independently O or S;
$R_a$ is H or $C_1$–$C_3$ alkyl;
$R_b$ and $R_c$ are independently $C_1$–$C_3$ alkyl;
Z is CH, $CCH_3$, $CC_2H_5$, CCl or CBr;
and their agriculturally suitable salts; provided that
(1) when X is halogen, then Z is CH and Y is $OCH_3$, $OC_2H_5$, $NH_2$, $NHCH_3$, $N(CH_3)_2$, $OCF_2H$ or $N(OCH_3)CH_3$;
(2) when X or Y is $C_1$ haloalkoxy, then Z is CH;
(3) when W is S, then R is H, Z is CH and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$,

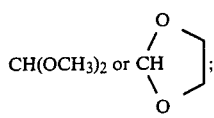

(4) when the total number of carbon atoms of X and Y is greater than four, then the combined number of carbons of $R_1$ and $R_2$ is less than or equal to six;
(5) when $R_2$ is $C(O)R_{17}$, then $R_1$ is other than $C_1$–$C_4$ haloalkyl or $C_2$ alkyl substituted with $C_1$–$C_2$ alkoxy or $C_1$–$C_2$ alkylthio, and Y is other than cyclopropyl;
(6) when Y is $C_2$–$C_5$ alkylthioalkyl, $C_2$–$C_5$ alkylsulfinylalkyl or $C_2$–$C_5$ alkylsulfonylalkyl, then $R_2$ is other than $CH(R_{17})NO_2$.

2. A compound of claim 1 where
W is O; and
R is H.

3. A compound of claim 2 where
E is a single bond;
X is $C_1$–$C_2$ alkyl, $C_1$–$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

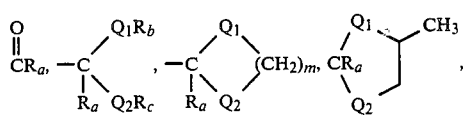

$OCF_2H$, $SCF_2H$, cyclopropyl, $C\equiv CH$ or $C\equiv CCH_3$;
Z is CH.

4. A compound of claim 3 where $R_2$ is $CH_2CN$, $CH_2N_3$,

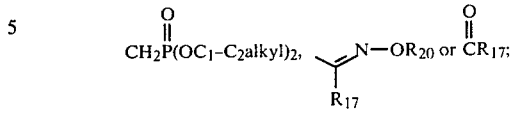

5. A compound of claim 4 where $R_1$ is F, Cl, Br, $NO_2$, $C_1$–$C_3$ alkyl, $C_1$–$C_2$ alkyl subsituted with 1–3F of Cl or 1Br, $C_2$–$C_3$ alkenyl, $C_2$–$C_3$ alkenyl substituted with 1–3F or Cl, $C_1$–$C_2$ alkoxy, $C_1$–$C_2$ alkoxy subsituted with 1–3F or Cl or 1-Br, allyloxy, propargyloxy, OC(Cl)=CHCl, $CO_2CH_3$, $CO_2C_2H_5$, $CO_2CH_2CH=CH_2$, $CO_2CH_2CH_2Cl$, $CO_2CH_2CH_2OCH_3$, $CONH(C_1-C_2\ alkyl)$, $CONCH_3(C_1-C_2\ alkyl$, $SO_2N(OCH_3)CH_3$, $SO_2NH(C_1-C_2\ alkyl)$, $SO_2N(C_1-C_2\ alkyl)_2$, $S(O)_nC_1-C_3\ alkyl$, $OSO_2C_1-C_3\ alkyl$, $C_1-C_2$ alkyl substituted with $OCH_3$ or $SCH_3$, $C_6H_5$ and $R_1$-A, $R_1$-B, $R_1$-C, $R_1$-D, $R_1$-E, $R_1$-F, $R_1$-G, $R_1$-H, $R_1$-I, $R_1$-J, $R_1$-K, $R_1$-L, $R_1$-M, $R_1$-N, $R_1$-O, $R_1$-P, $R_1$-Q, $R_1$-R, $R_1$-S, $R_1$-T, $R_1$-U, $R_1$-V or $R_1$-W.

6. A compound of claim 5 where
X is $CH_3$, $OCH_3$, $OCH_2CH_3$, Cl, $OCF_2H$ or $OCH_2CF_3$; and
Y is $CH_3$, $OCH_3$, $C_2H_5$, $CH_2OCH_3$, $NHCH_3$ or $CH(OCH_3)_2$.

7. A compound of claim 6 where $R_1$ is F, Cl, Br, $NO_2$, $CH_3$, $CF_3$ $C_1$–$C_2$ alkoxy, allyloxy, OC(Cl)=CHCl, $CO_2CH_3$, $CO_2C_2H_5$, $CO_2NHCH_3$, $CO_2N(CH_3)_2$, $SO_2NHCH_3$ $SO_2N(CH_3)_2$, $SO_2CH_3$, $SO_2C_2H_5$, $OSO_2CH_3$, $OSO_2C_2H_5$, $R_1$-A, $R_1$-B or $R_1$-C.

8. The compound of claim 1 which is 4-(cyanomethyl)-2-[[4,6-dimethoxypyrimidin-2-yl)aminocarbonyl]aminosulfonyl]benzoic acid, methyl ester.

9. A composition suitable for controlling the growth of undesired vegetation which comprises an effective amount of a compound of claim 1 and at least one of the following: surfactant, solid or liquid diluent.

10. A composition suitable for controlling the growth of undesired vegetation which comprises an effective amount of a compound of claim 2 and at least one of the following: surfactant, solid or liquid diluent.

11. A composition suitable for controlling the growth of undesired vegetation which comprises an effective amount of a compound of claim 3 and at least one of the following: surfactant, solid or liquid diluent.

12. A composition suitable for controlling the growth of undesired vegetation which comprises an effective amount of a compound of claim 4 and at least one of the following: surfactant, solid or liquid diluent.

13. A composition suitable for controlling the growth of undesired vegetation which comprises an effective amount of a compound of claim 5 and at least one of the following: surfactant, solid or liquid diluent.

14. A composition suitable for controlling the growth of undesired vegetation which comprises an effective amount of a compound of claim 6 and at least one of the following: surfactant, solid or liquid diluent.

15. A composition suitable for controlling the growth of undesired vegetation which comprises an effective amount of a compound of claim 7 and at least one of the following: surfactant, solid or liquid diluent.

16. A composition suitable for controlling the growth of undesired vegetation which comprises an effective amount of the compound of claim 8 and at least one of the following: surfactant, solid or liquid diluent.

17. A method for controlling the growth of undesired vegetation which comprises applying to the locus to be protected an effective amount of a compound of claim 1.

18. A method for controlling the growth of undesired vegetation which comprises applying to the locus to be protected an effective amount of a compound of claim 2.

19. A method for controlling the growth of undesired vegetation which comprises applying to the locus to be protected an effective amount of a compound of claim 3.

20. A method for controlling the growth of undesired vegetation which comprises applying to the locus to be protected an effective amount of a compound of claim 4.

21. A method for controlling the growth of undesired vegetation which comprises applying to the locus to be protected an effective amount of a compound of claim 5.

22. A method for controlling the growth of undesired vegetation which comprises applying to the locus to be protected an effective amount of a compound of claim 6.

23. A method for controlling the growth of undesired vegetation which comprises applying to the locus to be protected an effective amount of a compound of claim 7.

24. A method for controlling the growth of undesired vegetation which comprises applying to the locus to be protected an effective amount of the compound of claim 8.

* * * * *

UNITED STATES PATENT AND TRADEMARK OFFICE
CERTIFICATE OF CORRECTION

PATENT NO. : B1 4,678,498

DATED : January 24, 1989

INVENTOR(S) : Steven P. Artz

It is certified that error appears in the above-identified patent and that said Letters Patent is hereby corrected as shown below:

The title page should be deleted to appear as per attached title page.

Signed and Sealed this

Thirteenth Day of June, 1989

Attest:

*Attesting Officer*

DONALD J. QUIGG

*Commissioner of Patents and Trademarks*

REEXAMINATION CERTIFICATE (1005th)
United States Patent [19]
Artz

[11] B1 4,678,498

[45] Certificate Issued  Jan. 24, 1989

[54] HERBICIDAL SULFONAMIDES

[75] Inventor: Steven P. Artz, Kennett Square, Pa.

[73] Assignee: E. I. Du Pont de Nemours and Company, Wilmington, Del.

Reexamination Request:
No. 90/001,562, Jun. 24, 1988

Reexamination Certificate for:
Patent No.: 4,678,498
Issued: Jul. 7, 1987
Appl. No.: 860,229
Filed: May 12, 1986

Related U.S. Application Data

[63] Continuation-in-part of Ser. No. 743,955, Jun. 12, 1985, abandoned.

[51] Int. Cl.$^4$ .................... A01N 43/54; C07D 236/69; C07D 401/12; C07D 413/12
[52] U.S. Cl. .................... 71/87; 71/86; 71/90; 71/92; 71/93; 544/243; 544/296; 544/321; 544/324; 544/323; 544/331; 544/332; 544/229; 544/211; 544/212; 544/206; 544/207; 544/208; 544/209
[58] Field of Search .................... 71/92, 90, 86, 87; 544/243, 296, 321, 324, 323, 331, 332, 229

[56] References Cited
U.S. PATENT DOCUMENTS
4,310,346  1/1982 Levitt et al. .................... 71/92

FOREIGN PATENT DOCUMENTS
84/2722 10/1984 South Africa .

*Primary Examiner*—John M. Ford

[57] ABSTRACT

Novel compounds of Formula I are useful as herbicides and plant growth regulants.

REEXAMINATION CERTIFICATE (1005th)
United States Patent [19]
Artz

[11] B1 4,678,498
[45] Certificate Issued  Jan. 24, 1989

[54] HERBICIDAL SULFONAMIDES

[75] Inventor: Steven P. Artz, Kennett Square, Pa.

[73] Assignee: E. I. Du Pont de Nemours and Company, Wilmington, Del.

Reexamination Request:
No. 90/001,562, Jun. 24, 1988

Reexamination Certificate for:
Patent No.: 4,678,498
Issued: Jul. 7, 1987
Appl. No.: 860,229
Filed: May 12, 1986

Related U.S. Application Data

[63] Continuation-in-part of Ser. No. 743,955, Jun. 12, 1985, abandoned.

[51] Int. Cl.⁴ .................. A01N 43/54; C07D 236/69; C07D 401/12; C07D 413/12
[52] U.S. Cl. ........................... 71/87; 71/86; 71/90; 71/92; 71/93; 544/243; 544/296; 544/321; 544/324; 544/323; 544/331; 544/332; 544/229; 544/211; 544/212; 544/206; 544/207; 544/208; 544/209
[58] Field of Search ................. 71/92, 90, 86, 87; 544/243, 296, 321, 324, 323, 331, 332, 229

[56] References Cited
U.S. PATENT DOCUMENTS
4,310,346  1/1982  Levitt et al. ........................ 71/92

FOREIGN PATENT DOCUMENTS
84/2722  10/1984  South Africa .

Primary Examiner—John M. Ford

[57] ABSTRACT

Novel compounds of Formula I are useful as herbicides and plant growth regulants.

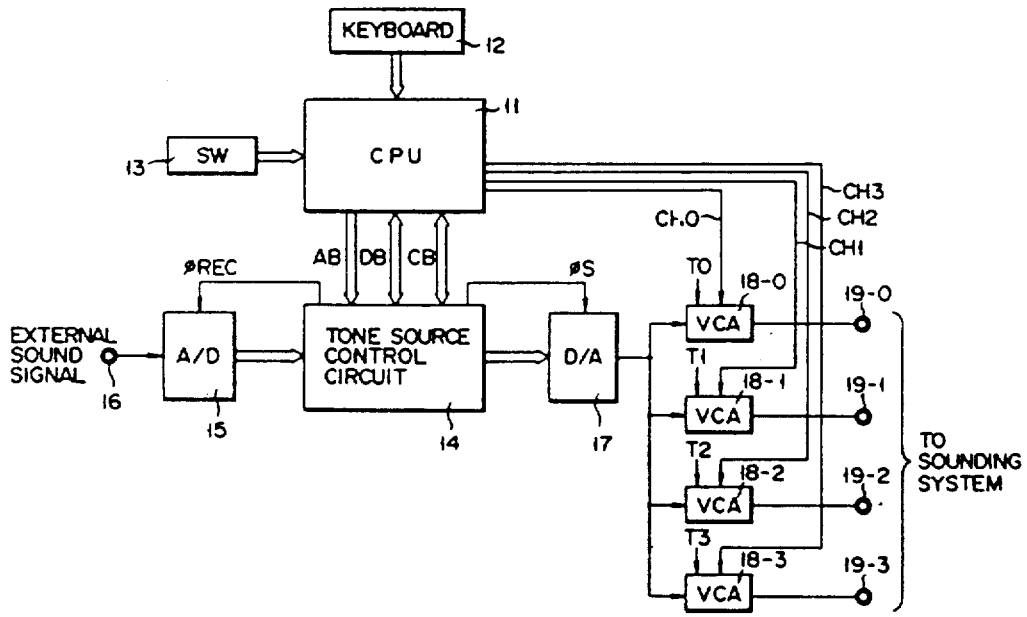

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-24, dependent on an amended claim, are determined to be patentable.

1. A compound of the formula:

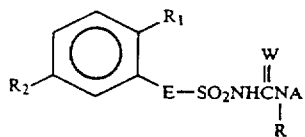

wherein
E is $CH_2$ or a single bond;
W is O or S;
R is H or $CH_3$;
$R_1$ is F, Cl, Br, $NO_2$, $C_1$-$C_4$ alkyl, $C_2$-$C_4$ alkenyl, $C_2$-$C_4$ haloalkenyl, $C_2$-$C_4$ alkynyl, $C_1$-$C_4$ haloalkyl, $C_1$-$C_4$ alkoxy, $OCH_2CH_2OCH_3$, $C_1$-$C_4$ haloalkoxy, $C_3$-$C_4$ alkenyloxy, $C_2$-$C_4$ haloalkenyloxy, $C_3$-$C_4$ alkynyloxy, $CO_2R_3$, $CONR_4R_5$, $SO_2NR_4R_5$, $SO_2N(OCH_3)CH_3$, $S(O)_nR_6$, $OSO_2R_7$, $C_1$-$C_2$ alkyl substituted with $C_1$-$C_2$ alkoxy, OH or $C_1$-$C_2$ alkylthio,

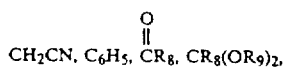

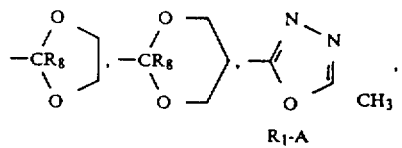

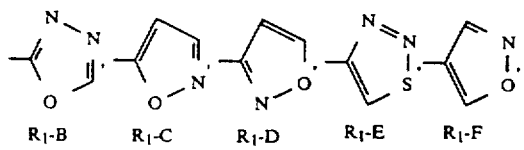

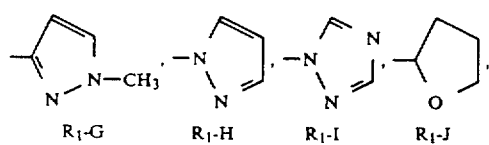

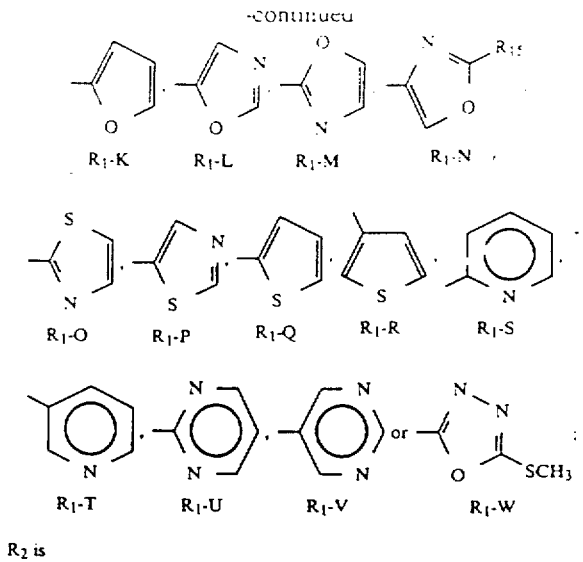

$R_2$ is

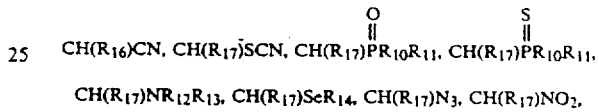

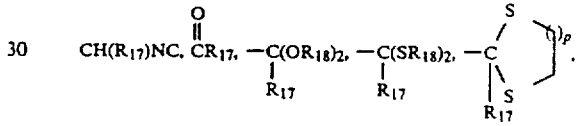

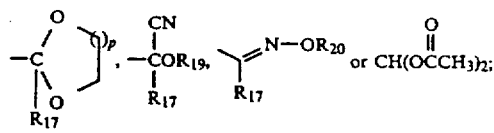

$R_3$ is $C_1$-$C_4$ alkyl, $C_3$-$C_4$ alkenyl, $C_3$-$C_4$ alkynyl,

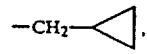

$CH_2CH_2Cl$, $CH_2CH_2F$, or $C_1$-$C_2$ alkyl substituted with $OCH_3$ or $SCH_3$;
$R_4$ is $C_1$-$C_3$ alkyl;
$R_5$ is H or $C_1$-$C_3$ alkyl;
$R_4$ and $R_5$ may be taken together to form $(CH_2)_3$ or $(CH_2)_4$;
$R_6$ is $C_1$-$C_3$ alkyl, $CH_2CH=CH_2$ or $CH_2C\equiv CH$;
$R_7$ is $C_1$-$C_3$ alkyl or $N(CH_3)_2$;
$R_8$ is H, $C_1$-$C_4$ alkyl, $C_3$-$C_4$ alkenyl, $C_3$-$C_4$ alkylnyl, $CH_2CH_2Cl$, $CH_2CH_2F$, $C_1$-$C_2$ alkyl substituted with $OCH_3$ or $SCH_3$ and $C_3$-$C_6$ cycloalkyl;
$R_9$ is $C_1$-$C_2$ alkyl;
$R_{10}$ and $R_{11}$ are independently $C_1$-$C_2$ alkyl, $C_1$-$C_2$ alkoxy, $C_1$-$C_2$ alkylthio, $NHCH_3$ or $N(CH_3)_2$;
$R_{12}$ and $R_{13}$ are independently H or $C_1$-$C_2$ alkyl;
$R_{14}$ is $C_1$-$C_3$ alkyl;
$R_{15}$ is H or $CH_3$;
$R_{16}$ is H, $C_1$-$C_2$ alkyl or F;
$R_{17}$ is H or $C_1$-$C_2$ alkyl;
$R_{18}$ is $C_1$-$C_2$ alkyl;
$R_{19}$ is H, $Si(CH_3)_3$ or $C_1$-$C_2$ alkyl;
$R_{20}$ is H or $C_1$-$C_2$ alkyl;
p is 1 or 2;

n is 0, 1, or 2;

A is

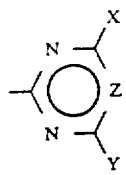

A-1

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido, cyano,

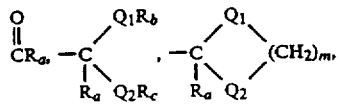

-continued

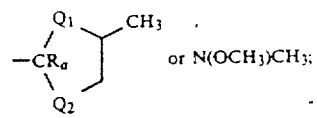 or $N(OCH_3)CH_3$;

m is 2 or 3;

$Q_1$ and $Q_2$ are independently O or S;

$R_4$ is H or $C_1$–$C_3$ alkyl;

$R_b$ and $R_c$ are independently $C_1$–$C_3$ alkyl;

Z is CH, $CCH_3$, $CC_2H_5$, CCl or CBr;

and their agriculturally salts; provided that (1) when X is halogen, then Z is CH and Y is $OCH_3$, $OC_2H_5$, $NH_2$, $NHCH_3$, $N(CH_3)_2$, $OCF_2H$ or $N(OCH_3)CH_3$;

(2) when X or Y is $C_1$ haloalkoxy, then Z is CH;

(3) when W is S, then R is H, Z is CH and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$,

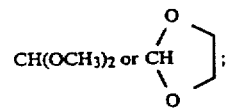

(4) when the total number of carbon atoms of X and Y is greater than four, then the combined number of carbons of $R_1$ and $R_2$ is less than or equal to six;

(5) when $R_2$ is $C(O)R_{17}$, then $R_1$ is other than $C_1$–$C_4$ haloalkyl or $C_2$ alkyl substituted with $C_1$–$C_2$ alkoxy, OH or $C_1$–$C_2$ alkylthio, and Y is other than cyclopropyl;

(6) when Y is $C_2$–$C_5$ alkylthioalkyl, $C_2$–$C_5$ alkylsulfinylalkyl or $C_2$–$C_5$ alkylsulfonylalkyl, then $R_2$ is other than $CH(R_{17})NO_2$ (7) *when $R_2$ is $C(O)R_{17}$ then $R_1$ is other than $SO_2NR_4R_5$ and $SO_2N(OCH_3)CH_3$.*

* * * * *